US009220721B2

(12) United States Patent
Aguirre et al.

(10) Patent No.: US 9,220,721 B2
(45) Date of Patent: Dec. 29, 2015

(54) METHODS FOR HEART REGENERATION

(71) Applicant: The Salk Institute for Biological Studies, La Jolla, CA (US)

(72) Inventors: Aitor Aguirre, La Jolla, CA (US); Ignacio Sancho-Martinez, San Diego, CA (US); Juan Carlos Izpisua-Belmonte, La Jolla, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 14/052,538

(22) Filed: Oct. 11, 2013

(65) Prior Publication Data
US 2014/0221463 A1 Aug. 7, 2014

Related U.S. Application Data

(60) Provisional application No. 61/712,701, filed on Oct. 11, 2012.

(51) Int. Cl.
| | |
|---|---|
| C12N 15/11 | (2006.01) |
| A61K 31/7088 | (2006.01) |
| A61K 31/7105 | (2006.01) |
| A61K 31/713 | (2006.01) |

(52) U.S. Cl.
CPC .......... *A61K 31/7088* (2013.01); *A61K 31/713* (2013.01); *A61K 31/7105* (2013.01); *C12N 15/111* (2013.01); *C12N 2310/113* (2013.01); *C12N 2310/141* (2013.01); *C12N 2320/30* (2013.01)

(58) Field of Classification Search
None
See application file for complete search history.

(56) References Cited

U.S. PATENT DOCUMENTS

| | | | |
|---|---|---|---|
| 2007/0104688 A1* | 5/2007 | Rossi et al. | 424/93.2 |
| 2009/0306181 A1* | 12/2009 | Ikeda et al. | 514/44 A |
| 2010/0267804 A1 | 10/2010 | Port et al. | |
| 2012/0328686 A1 | 12/2012 | Grundmann et al. | |

OTHER PUBLICATIONS

Aguirre, et al. "Reprogramming toward heart regeneration: stem cells and beyond." *Cell Stem Cell* 12, No. 3 (2013): 275-284.
Brandenburger, et al. "Organotypic slice culture from human adult ventricular myocardium." *Cardiovascular Research* 93, No. 1 (2012): 50-59.
Collins, et al. "An ACF1—ISWI chromatin-remodeling complex is required for DNA replication through heterochromatin." *Nature Genetics* 32, No. 4 (2002): 627-632.
Eulalio, et al. "Functional screening identifies miRNAs inducing cardiac regeneration." *Nature* 492, No. 7429 (2012): 376-381.
Gurtan, et al. "The role of miRNAs in regulating gene expression networks." *Journal of Molecular Biology* 425, No. 19 (2013): 3582-3600.
Jopling, et al. "Zebrafish heart regeneration occurs by cardiomyocyte dedifferentiation and proliferation." *Nature* 464, No. 7288 (2010): 606-609.
Knapp, et al. "Regeneration and reprogramming." *Current Opinion in Genetics & Development* 22, No. 5 (2012): 485-493.
Laflamme, et al. "Heart regeneration." *Nature* 473, No. 7347 (2011): 326-335.
Mueller, et al. "The miR-99 family regulates the DNA damage response through its target SNF2H." *Oncogene* 32, No. 9 (2013): 1164-1172.
Paige, et al. "A temporal chromatin signature in human embryonic stem cells identifies regulators of cardiac development." *Cell* 151, No. 1 (2012): 221-232.
Poss, et al. "Heart regeneration in zebrafish." *Science* 298, No. 5601 (2002): 2188-2190.
Qian, et al. "In vivo reprogramming of murine cardiac fibroblasts into induced cardiomyocytes." *Nature* 485, No. 7400 (2012): 593-598.
Roush, et al. "The let-7 family of microRNAs." *Trends in Cell Biology* 18, No. 10 (2008): 505-516.
Seifert, et al. "Skin shedding and tissue regeneration in African spiny mice (Acomys)." *Nature* 489, No. 7417 (2012): 561-565.
Senyo, et al. "Mammalian heart renewal by pre-existing cardiomyocytes." *Nature* 493, No. 7432 (2013): 433-436 (published on-line Dec. 5, 2012).
Song, et al. "Heart repair by reprogramming non-myocytes with cardiac transcription factors." *Nature* 485, No. 7400 (2012): 599-604.
Zhang, et al. "In vivo cardiac reprogramming contributes to zebrafish heart regeneration." *Nature* 498, No. 7455 (2013): 497-501.

* cited by examiner

*Primary Examiner* — Tracy Vivlemore
*Assistant Examiner* — Kate Poliakova
(74) *Attorney, Agent, or Firm* — Klarquist Sparkman, LLP

(57) ABSTRACT

Methods for heart regeneration are provided. The invention provided herein includes methods of modulating proliferation of cardiomyocytes using small molecules and micro RNAs. In embodiments, the methods provided may be used to increase proliferation or cardiomyocytes. Further provided are methods to be used for the treatment of myocardial infarction.

15 Claims, 25 Drawing Sheets

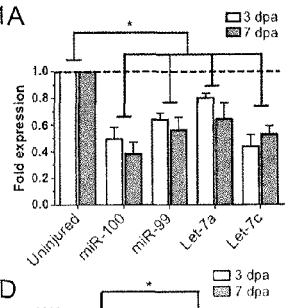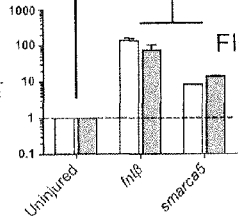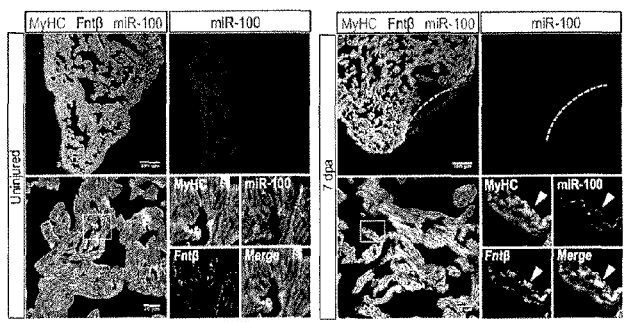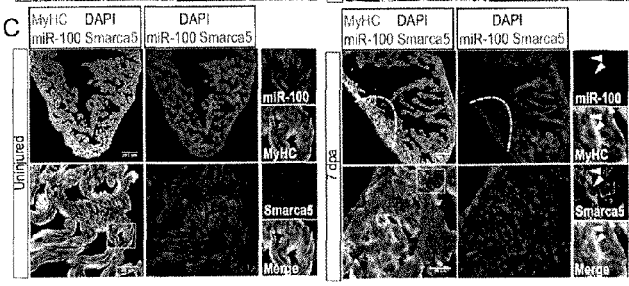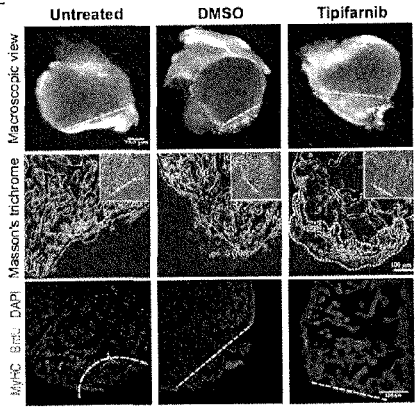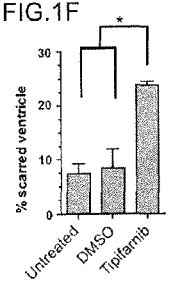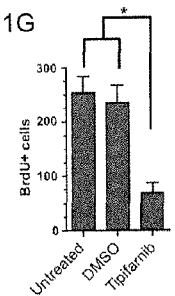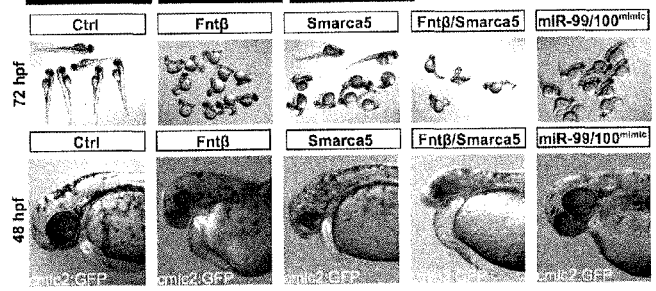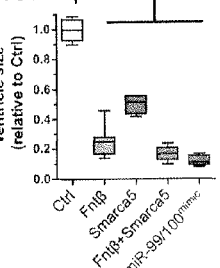

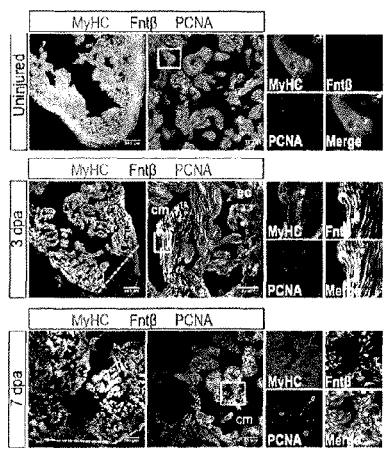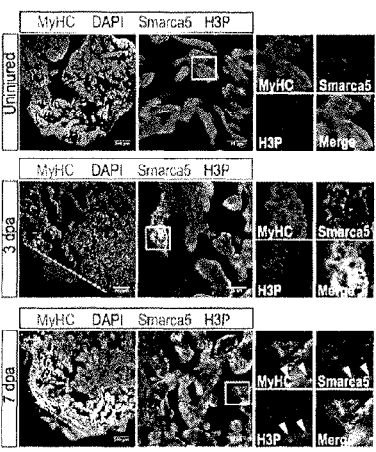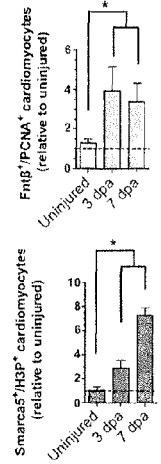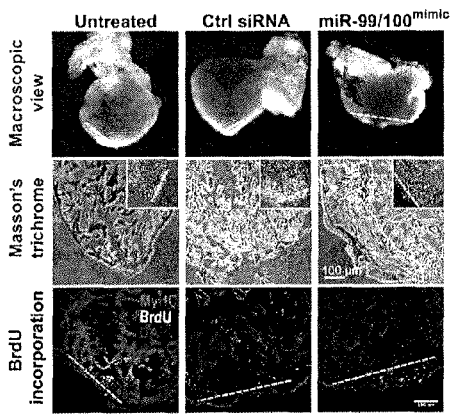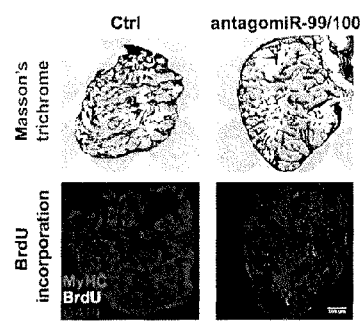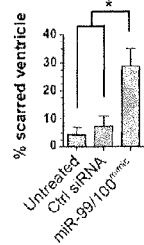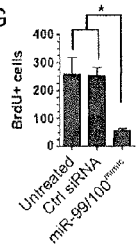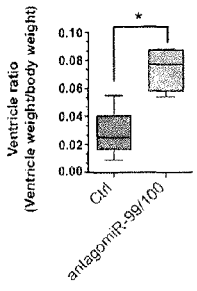

FIG.4A 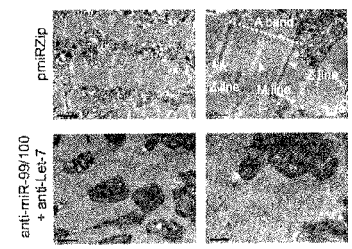   FIG.4B 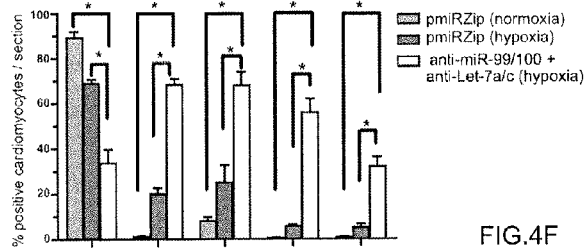
FIG.4C 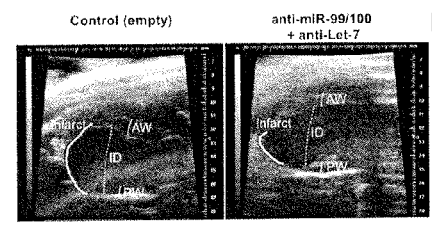   FIG.4D 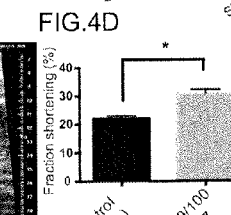   FIG.4E 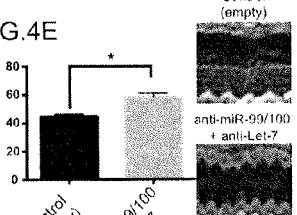   FIG.4F
FIG.4G 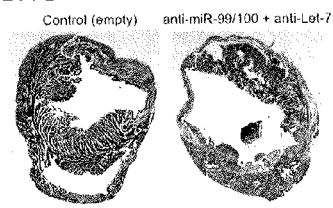 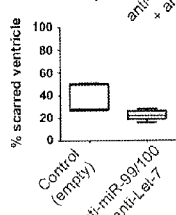
FIG.4H 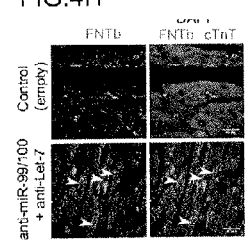   FIG.4I   FIG.4J 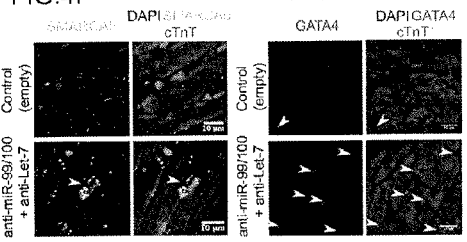 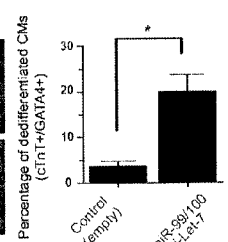
FIG.4K 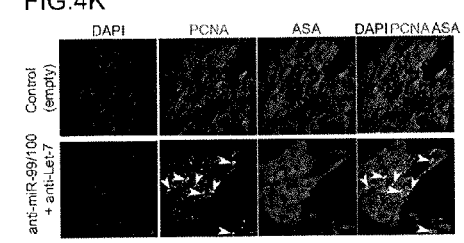   FIG.4L 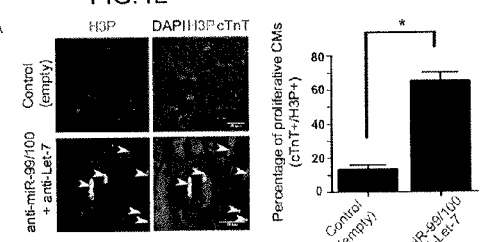 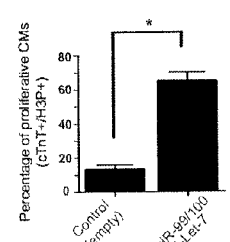

FIG.5A
FIG.5B
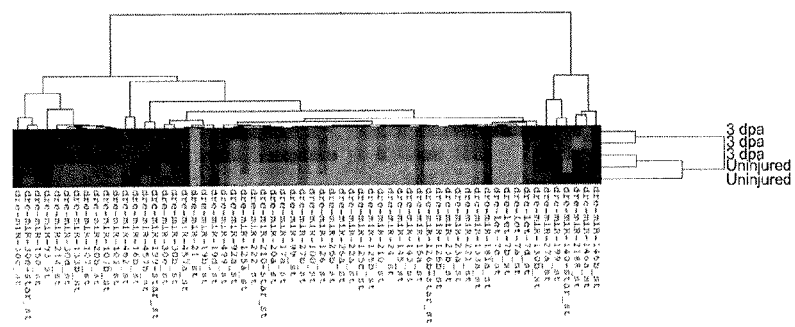
- Chromatin remodeling
- Kinase activity
- Phosphatase activity
- Transcriptional regulation
- Limb morphogenesis
- Others
FIG.5C
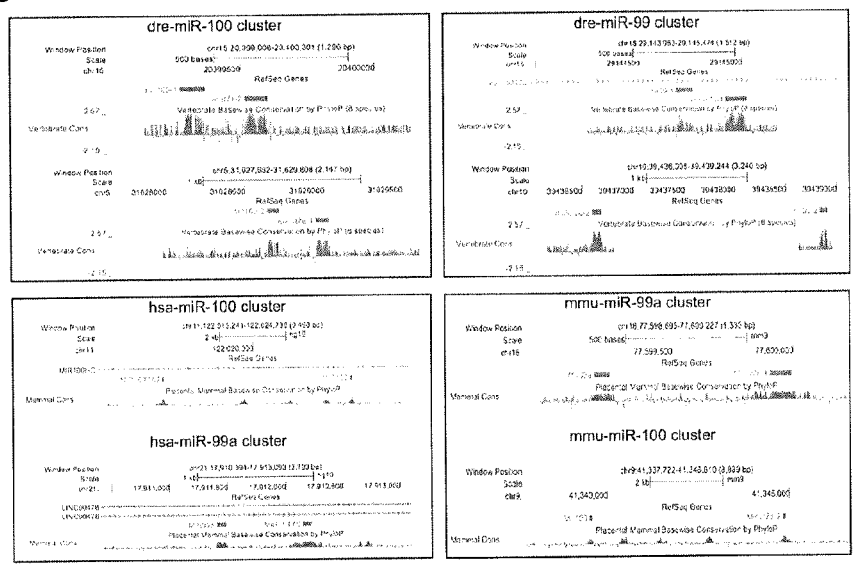

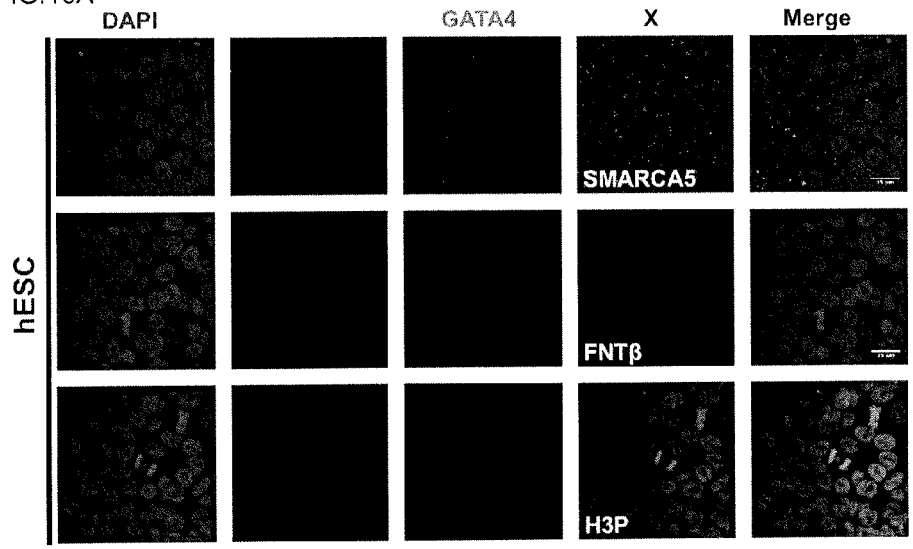
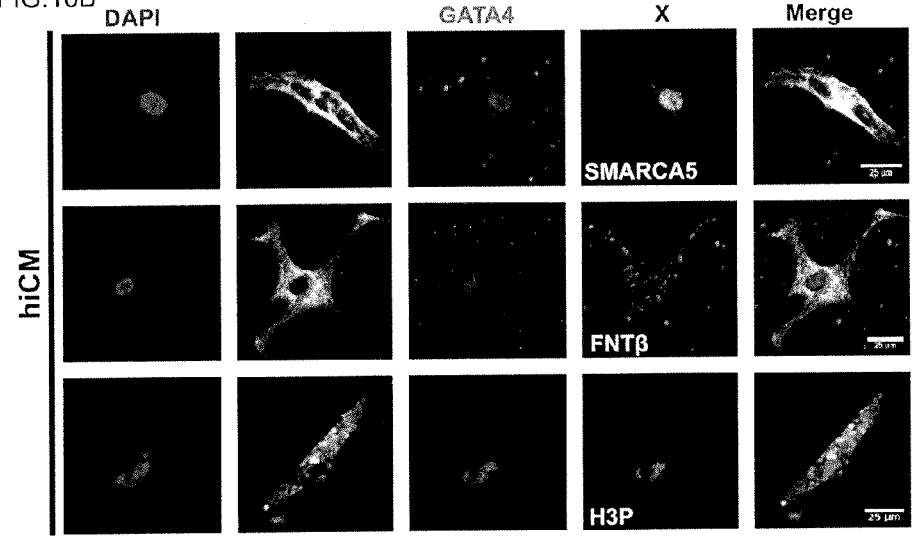

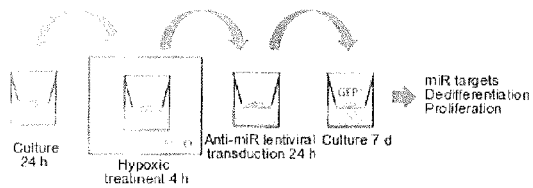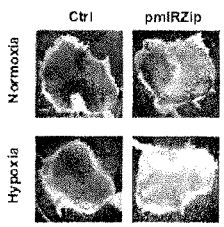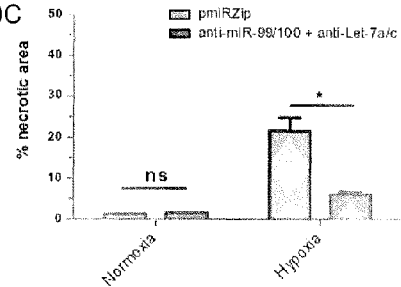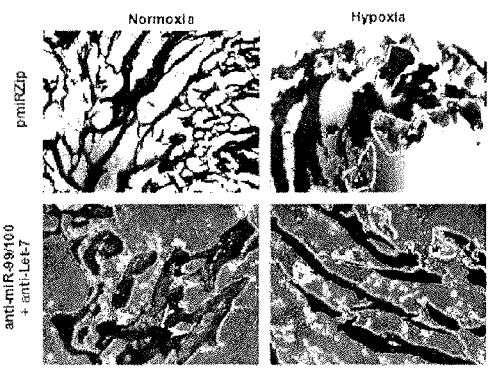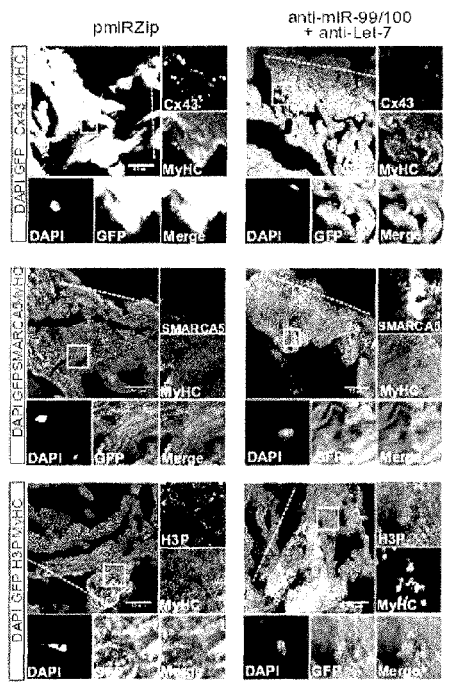

Animal 1

Animal 2

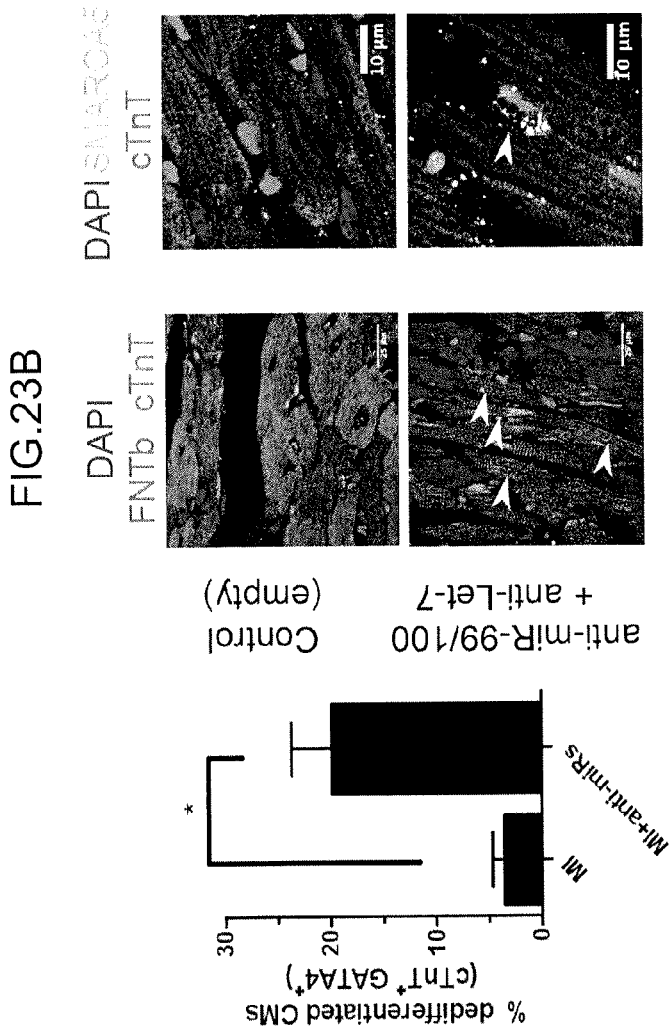
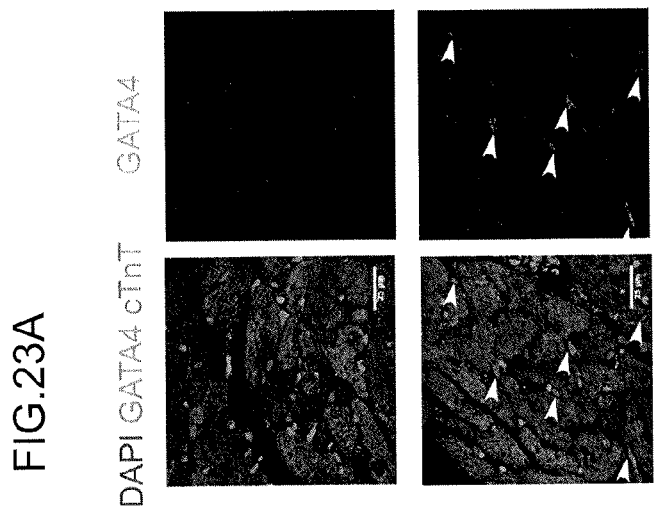
FIG. 23A
FIG. 23B

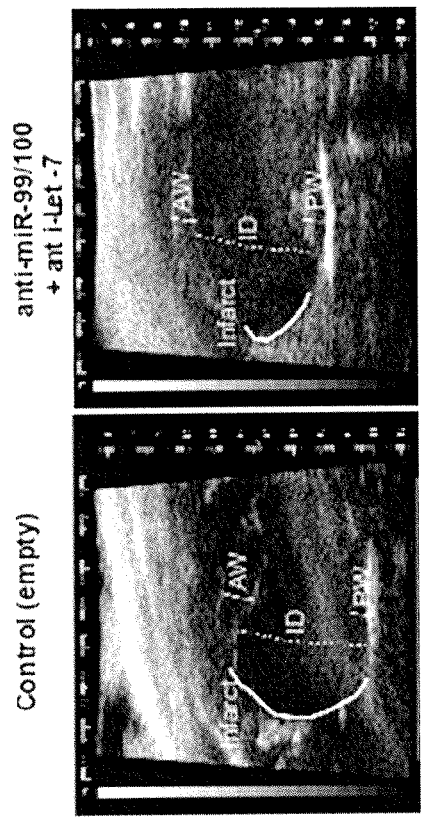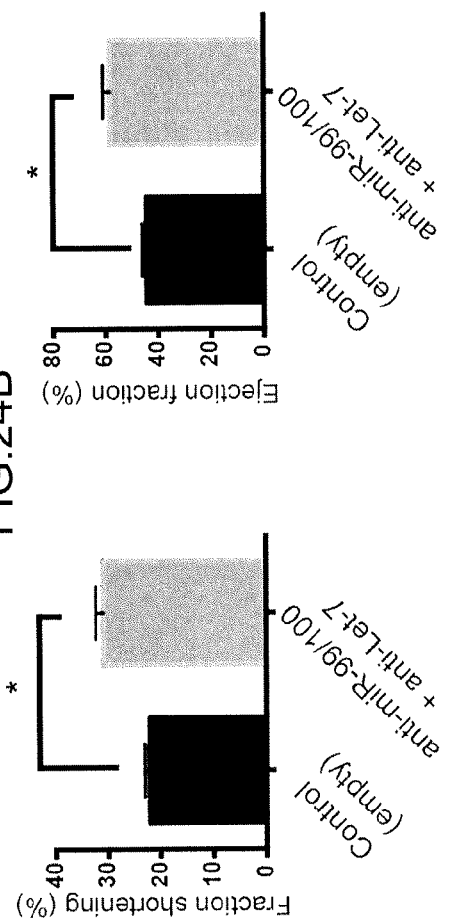
FIG. 24A
FIG. 24B
18 days post-infarction

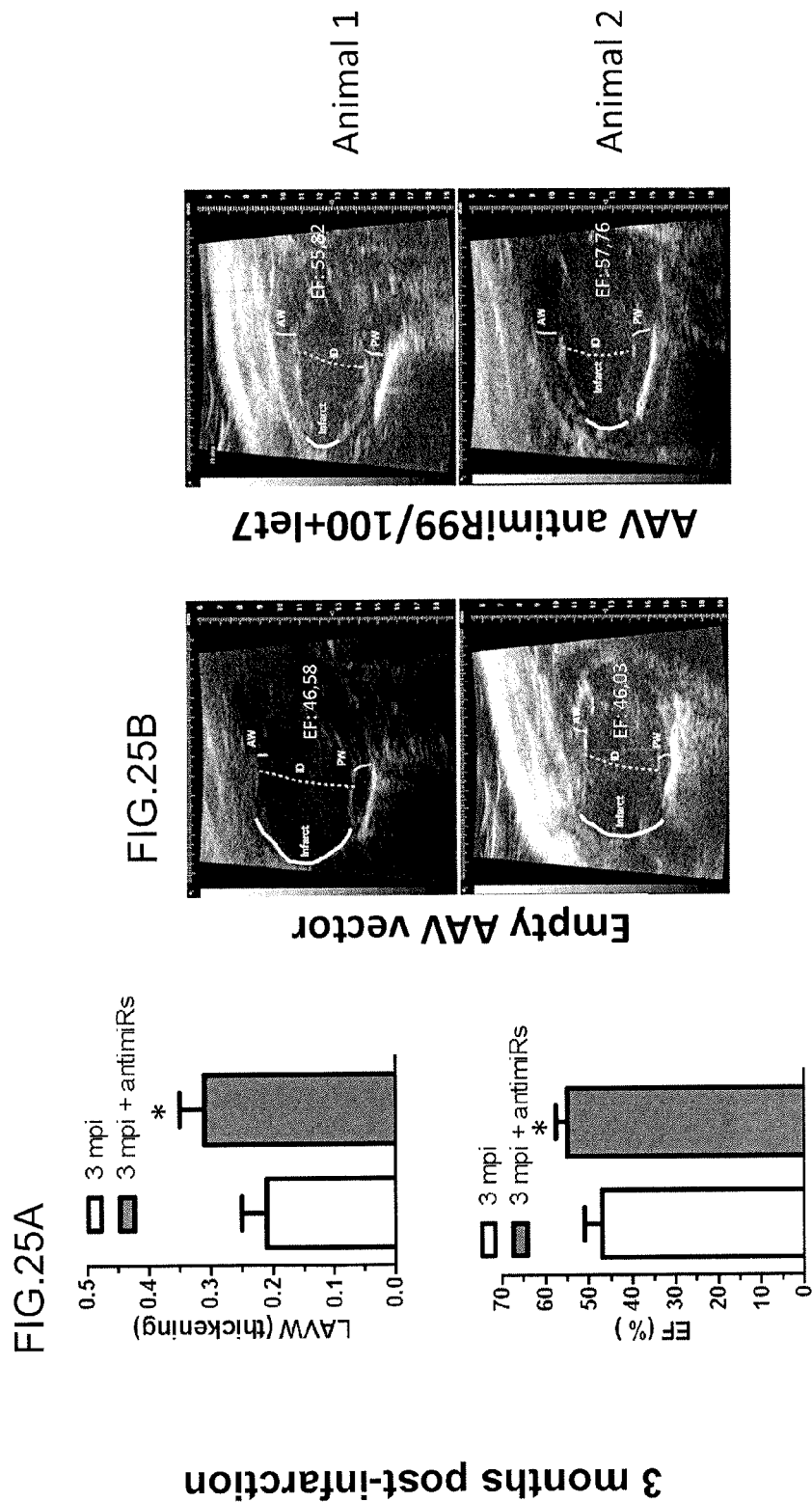

METHODS FOR HEART REGENERATION

CROSS-REFERENCES TO RELATED APPLICATIONS

This application claims the benefit of U.S. Provisional Appl. No. 61/712,701, filed Oct. 11, 2012, the contents of which are incorporated herein by reference and for all purposes.

STATEMENT OF GOVERNMENT SUPPORT

This invention was made with government support under grant U01 HL107442-04 awarded by The National Heart, Lung and Blood Institute; the government has certain rights in the invention.

REFERENCE TO A "SEQUENCE LISTING," A TABLE, OR A COMPUTER PROGRAM LISTING APPENDIX SUBMITTED AS AN ASCII TEXT FILE

The Sequence Listing is submitted as an ASCII text file [9496002SequenceListing.txt,Jun. 8, 2015, 7.45 MB], which is incorporated by reference herein.

BACKGROUND OF THE INVENTION

Heart failure remains one of the leading causes of mortality in the developed world. Whereas the mammalian heart is endowed with certain regenerative potential, endogenous cardiomyocyte proliferation is insufficient for functional heart repair upon injury. Interestingly, non-mammalian vertebrates, such as the zebrafish, can regenerate the damaged heart by inducing cardiomyocyte dedifferentiation and proliferation. By screening regenerating zebrafish hearts Applicants identified miR-99/100 down-regulation as a key process driving cardiomyocyte dedifferentiation. Experimental down-regulation of miR-99/100 in primary adult murine and human cardiomyocytes led to an increase in the number of proliferating cardiomyocytes. AAV-mediated in vivo down-regulation of miR-99/100 after acute myocardial injury in mice induced mature cardiomyocyte proliferation, diminished infarct size and improved heart function. Applicants' study unveils conserved regenerative mechanisms between zebrafish and mammalian cardiomyocytes and represents a proof-of-concept on the suitability of activating pro-regenerative responses for healing the diseased mammalian heart.

BRIEF SUMMARY OF THE INVENTION

In one aspect, a method of modulating proliferation of a cardiomyocyte is provided. The method includes (i) transfecting a cardiomyocyte with a nucleic acid encoding a micro RNA modulator, thereby forming a transfected cardiomyocyte; and (ii) allowing the transfected cardiomyocyte to divide, thereby modulating proliferation of the cardiomyocyte.

In another aspect, a method of modulating proliferation of a cardiomyocyte is provided. The method includes (i) contacting a cardiomyocyte with a small molecule, thereby forming a treated cardiomyocyte; and (ii) allowing the treated cardiomyocyte to divide, thereby modulating proliferation of the cardiomyocyte.

In another aspect, a method of treating myocardial infarction in a subject in need thereof is provided. The method includes administering to the subject a therapeutically effective amount of a nucleic acid encoding a micro RNA modulator, wherein the RNA modulator increases cardiomyocyte proliferation thereby treating the myocardial infarction.

In another aspect, a method of treating myocardial infarction in a subject in need thereof is provided. The method includes administering to the subject a therapeutically effective amount of a nucleic acid encoding an antagonist of a mir 99 micro RNA and a nucleic acid encoding an antagonist of a let-7a micro RNA, thereby treating the myocardial infarction.

In another aspect, a method of treating myocardial infarction in a subject in need thereof is provided. The method includes administering to the subject a therapeutically effective amount of a small molecule, wherein the small molecule increases cardiomyocyte proliferation thereby treating the myocardial infarction.

BRIEF DESCRIPTION OF THE DRAWINGS

FIGS. 1A-J. miR-99/100 and Let-7a/c are involved in the early cardiac regenerative response in the zebrafish. (FIG. 1A) Amputated hearts were allowed to regenerate for 3 and 7 days, and then analyzed by real time RT-PCR for microRNA candidates miR-99/100 and Let-7a/c (n=8). (FIGS. 1B, C) FISH/double immunofluorescence was used to determine cardiomyocyte specific expression of microRNA-100 (n=5, see also FIG. 6) and its downstream targets fntβ (FIG. 1B) and smarca5 (FIG. 1C) in uninjured (left panel) and 7 dpa conditions (right panel). Cardiomyocytes in regenerating hearts exhibited remarkable low levels of both miRs, and inversely correlating high levels of Fntβ and Smarca5. (FIG. 1D) Gene expression fold change of fntβ and smarca5 in amputated hearts (n=8). (FIG. 1E) Chemical inhibition of fnt activity with Tipifarnib dramatically reduced cardiomyocyte proliferation and heart regeneration in amputated fish, leading to scarring as determined by Masson's Trichromic (FIG. 1F) staining and BrDU incorporation (FIG. 1G) (n=6). (FIGS. 1H, I, J) Knock-down of fntβ and/or smarca5 in embryos resulted in abnormally small animals and reduced ventricle size in cmlc2:GFP animals. The same phenotype was observed upon injection of miR-99/100 mimics (n>50). Dashed line: amputation plane. Boxed area: magnified field. Arrowheads: cells of interest.

FIGS. 2A-J. Heart regeneration in the fish is controlled by miR-99/100 and Let-7a/c. (FIG. 2A,B) Dedifferentiating cardiomyocytes express high levels of Fntβ (from top to bottom, uninjured, 3 dpa and 7 dpa, panel FIG. 2A) and Smarca5 (from top to bottom, uninjured, 3 dpa and 7 dpa, panel FIG. 2B) with a 3.5-fold and 7-fold protein increment at 7 dpa, respectively, (see histogram in FIGS. 2C, D; n=5). (FIGS. 2E, F, G) Exogenous intra-cardiac administration of miR-99/100 mimics led to defective cardiac regeneration, scarring and reduced cardiomyocyte proliferation (n=6). (FIG. 2H) miR-99/100 inhibitors exerted the opposite effect in uninjured adult animals, inducing significant cardiac hyperplasia (FIG. 2I) and increased ventricle size (FIG. 2J; n=6). Dashed line: amputation plane. Boxed area: magnified area. Ec: endocardial cells; cm: cardiomyocytes. Arrowheads: cells of interest.

(FIGS. 3B, D) Dynamics of cardiomyocyte progenitor marker and Fntβ/Smarca5 expression during murine (FIG. 3B) and human (FIG. 3D) cardiac maturation. Both Fntβ and Smarca5 are up-regulated at cardiac progenitor stages, and strongly repressed in adult hearts (n=6). (FIGS. 3E, F) Cultured adult murine cardiomyocytes transduced with anti-miR-99/100+anti-Let-7 reverted to a dedifferentiated-like state, re-expressing GATA4 and dissembling the cytoskeleton (see also FIG. 17; n=3). (FIGS. 3G, H) Transduction with anti-miRs was sufficient to efficiently drive adult cardiomyocytes to a proliferative state (FIG. 3G), with beating functionality (FIG. 3H) (n=3).

FIGS. 4A-L. MicroRNA silencing is sufficient to induce heart regeneration in a murine model of myocardial infarction. (FIGS. 4A, B) Organotypic cultures of adult heart tissue were employed to study the effects of microRNA-99/100 and Let-7a/c silencing. (FIG. 4A) After 7 days of treatment, myocardial tissue became disorganized, with a loss of sarcomeric structures as determined by electron microscopy analysis (n=6). (FIG. 4B) Furthermore, re-expression of dedifferentiation markers was detected by immunofluorescence evaluation/quantification, as well as cardiomyocyte proliferation and FNTβ and SMARCA5 expression in normoxic and hypoxic conditions (n=6). (FIG. 4C) Representative pictures of echocardiography performed in control (left panel) and treated animals (right panel) at 18 days post-myocardial infarction (MI). In vivo silencing of miR-99/100 and Let-7 led to significant improvements in fractional shortening (FIGS. 4D, F) and ejection fraction (FIGS. 4E, F) at 18 days post-MI (n=5). (FIG. 4G) Left panel, reduced infarct size in miR-99/100 and Let-7 treated animals is confirmed by Masson's trichromic staining; (FIG. 4G) Right panel, quantification of scar size by Masson's thrichromic staining (FIG. 4G; n=5). (FIGS. 4H-J) Recovery was accompanied by cardiomyocyte-specific expression of FNTβ (FIG. 4H) and SMARCA5 (FIG. 4I), as well as GATA4 re-expression (FIG. 4J, right panel shows quantification of this data) as determined by immunofluorescence analyses (n=5). (FIGS. 4K, L, panel on the right shows quantification of this data) Regeneration was mediated by a dramatic increase in proliferating cardiomyocytes as determined by PCNA (FIG. 4K) and H3P (FIG. 4L) stainings (n=5). Arrowheads: cells of interest.

FIGS. 5A-C. miR-99/100 and Let-7a/c are located in same genomic cluster and their functions and protein targets are conserved across vertebrates. (FIG. 5A) Microarray analysis identified a subset of differentially regulated microRNAs during early stages of regeneration in the zebrafish heart (n=4). Interestingly, most of them were consistently down-regulated. (FIG. 5B) Bioinformatic analysis of the most relevant signaling pathways targeted by miR-99/100 and Let-7a/c. (FIG. 5C) Genomic organization and conservation of miR-99/100 and Let-7a/c clusters in vertebrates (upper left: zebrafish miR-100 cluster; upper right: zebrafish miR-99 cluster; lower left: human miR-99/100 clusters; lower right: murine miR-99/100 clusters).

(FIGS. 6A-D) FISH/immunofluorescence analyses on zebrafish heart sections from uninjured and amputated animals at 3 and/or 7 dpa. (FIGS. 6A, B) FISH/immunofluorescence analysis of miR-100 and Fntβ/Smarca5 expression (see also FIG. 1; n=8). (FIGS. 6C, D) FISH/immunofluorescent analysis of miR-99 and Fntβ/Smarca5 expression during regeneration (upper row, miR-99 effects on Fntb expression at uninjured (left), 3 dpa (center) and 7 dpa (right) conditions; lower row, miR-99 effects on Smarca5 expression at uninjured (left), 3 dpa (center) and 7 dpa (right) conditions). (n=8). Dashed line: amputation plane. Boxed area: magnified in inset.

(FIG.7A) For the Fntb 3'UTR, miR-100 (query) is SEQ ID NO: 1131, miR99 (query) is SEQ ID NO: 1132, and the reference sequences (Ref) are nucleotides 154-175 of SEQ ID NO: 1118 and 155-175 of SEQ ID NO: 1118, respectively. For the Smarca5 3' UTR, miR-100 (query) is SEQ ID NO: 1131, miR-99 (query) is SEQ ID NO: 1132, and the reference sequences (Ref) are nucleotides 51-74 of SEQ ID NO: 1119 and 52-74 of SEQ ID NO: 1119, respectively. For Let-7a, the query is SEQ ID NO: 1136 and the reference sequence (Ref) is nucleotides 210 to 231 of SEQ ID NO: 1119. Miranda-based binding predictions of miR-99/100 to zebrafish Fntb (upper panel) and Smarca5 (lower panel) 3' UTRs. (FIG.7B) Luciferase assay to determine biochemical binding of miR-99/100 to the predicted targets Fntb and Smarca5 for zebrafish (upper and middle rows) and human (lower row) 3'UTRs. Fish and human UTRs were subcloned in the pGL3 vector and subjected to microRNA mimic knockdown in vitro. pGL3: empty vector; AS-UTR: antisense-UTR (negative control); UTR: 3'untranslated region.

(FIG. 9A) Expression of miR-99/100 is very low during the first stages of development and dramatically increases at 3 dpf in zebrafish (n=10). (FIG. 9B) fntβ and smarca5 expression inversely correlate with miR-99/100 in developing embryos (n=10). (FIGS. 9C, D) Both Fntβ and Smarca5 are present at high levels in developing hearts (n=10). V: ventricle; A: atrium; Eb: erythroblasts.

(FIGS. 10A, B) Immunofluorescent stainings for proliferating cardiomyocytes at 30 dpa, when regeneration in the zebrafish heart is mostly complete (n=3). Fntβ and Smarca5 presence in the myocardium returned to pre-amputation levels at 30 dpa, when regeneration is mostly completed. (FIG. 10C) Strategy for the scarring experiments to identify the improtance in regeneration of miR-99/100. (FIG. 10D) Successful heart delivery of antagomiRs was evaluated by injection of a matched-size Cy5-labelled oligonucleotide against GFP in cmlc2:GFP animals (n=3). Dashed line: amputation plane. Boxed area: magnified section.

(FIGS. 11A, B) At 3 and 7 dpa, a significant fraction of farnesylated proteins was detected in dedifferentiating cardiomyocytes as determined by immunofluorecence (n=5). Boxed area: magnified section.

(FIGS. 13A,B) The chromatin remodeling agents Cbx5 (FIG. 13A) and Cbx3a (FIG. 13B), which act in concert with Smarca5, were found in the nucleus of dedifferentiating cardiomyocytes indicating a wave of chromatin remodeling. The following is shown in the histograms of FIG. 13A and FIG. 13B from left to right: First panel (bottom and top histogram): DAPI stain, second panel (bottom and top histogram): MyHC stain; third panel (bottom and top histogram): PCNA stain; forth panel (bottom and top histogram):Cbx5 stain; fifth panel (bottom and top histogram): merge of histograms of panels one, two three and four.(n=4). Arrowheads: cells of interest.

(FIGS. 15A-C) Identical patterns of expression were found for miR-99/100 and Let-7a/c, as well as Fntβ and Smarca5, to those observed in the developing zebrafish (FIG. 15A: embryonic day 11; FIG. 15B: postnatal day 2; FIG. 15C: adult) (n=6). (FIG. 15D) Quantification showing the number of double positive cells for miR-99/100 (FIG. 15D upper left), Let-7a/c (FIG. 15D upper right), Fntβ (FIG. 15D lower left) and Smarca5 (FIG. 15D lower right) (n=6).

FIGS. 16A-B. Human ESC-derived, proliferation-competent immature cardiomyocytes (hiCM) possessed the same phenotype observed in fish and mouse dedifferentiated cardiomyocytes. (FIG. 16A) Immunofluorescence for the indicated proteins in human embryonic stem cells (FIG. 16A, Images are individual panels of the merged figure shown at in the last column). (FIG. 16B) hiCMs showed expression of GATA4, SMARCA5 and FNTβ, which was progressively lost with decreased proliferative capacity (n=3). The following is shown in the histograms of FIG. 16A and FIG. 16B from left to right: Histograms show immunostaining with DAPI (first panel), MyHC (second panel), GATA4 (third panel), SMARCA5 (forth panel top), FNTbeta (forth panel middle), of H3P (forth panel bottom) and a merged histogram (fifth panel).

(FIG. 17A, Images represent individual panels of the merged image shown in the last column) Untreated adult murine cardiomyocytes spontaneously disorganized sarcomeric structures in vitro, but did not dedifferentiate or express FNTβ, SMARCA5, GATA4 or proliferative markers. However, upon lentiviral transduction with anti-Let-7 alone (FIG. 17B, Images represent individual panels of the merged image shown in the last column) or both anti-Let-7and anti-miR-99/100 (FIG. 17C, Images represent individual panels of the merged image shown in the last column) they re-expressed all those markers (n=3). (FIG. 17D) Functional beating properties were preserved in dedifferentiated cardiomyocytes, suggesting a degree of spontaneous redifferentiation, except for anti-Let-7 treatment. (FIGS. 17E, F) Cardiomyocyte dedifferentiation was evaluated by simultaneously measuring GATA4 and sarcomeric myosin expression and organization in cultured cardiomyocytes (n=3).

(FIG. 18A) Human Fibroblasts (left panel) or endothelial cells (right panel) expressed basal levels of FNTβ, SMARCA5 and negligible levels of miR-99/100 and Let-7a/c (data not shown), and were insensitive to miR silencing (FIGS. 18A, B, C), indicating specificity of the treatment in a heart setting. (FIG. 18C) Images used for quantification of data shown in A and B (Images represent individual panels of the merged image shown in the last column) (n=3).

FIGS. 20A-E. Hypoxic injury in organotypic culture leads to increased dedifferentiation. (FIG. 20A) Schematic of hypoxia experiments. (FIG. 20B) Efficient lentiviral delivery was achieved in ex vivo conditions for all anti-miRs. (FIGS. 20C, D) Histomorphometric evaluation of the damaged myocardium in normoxic and hypoxic conditions by employing Masson's trichrome staining (n=4). (FIG. 20E) The dedifferentiation response was characterized by GATA4, Cx43, H3P, Fntβ and Smarca5 stainings (From top to bottom, Cx43, SMARCA5, H3P) (n=4). Dashed line: adjacent necrotic patch. Boxed area: magnified section. Dashed lines: necrotic tissue.

(FIG. 21A) At 18 dpi (days post infarction) mice treated with antimiR's exhibit a significant improvement in ejection fraction and fractional shortening, as well as reduction in scar size. (FIG. 21B) At 3 mpi (months post infarction) the improvements are still present (left panels, echocardiographic quantification; right panel, representative images), with further reduction of scar size and significant enlargement of the LAVW, indicative of replenishment of the myocardial mass.

FIGS. 23A-B. In vivo dedifferentiation by anti-miR delivery. (FIG. 23A): left panel, GATA4 immunofluorescence; right panel, quantification of the data shown (FIG. 23B): histogram showing percentage of dedifferentiated CMs; (FIG. 23C): SMARCA5 immunofluorescence.

FIGS. 24A-B. Anti-miR99/100/let-7 delivery enhances functional recovery after infarction. Echocardiography measurements in infarcted animals treated with control vs. anti-miR treatment indicate significant regeneration after treatment (FIG. 24A). Quantification of those animals shows statistically significant functional recovery, both in farction shortening (left panel) as well as ejection fraction (right panel).

FIGS. 25A-B. Anti-miR99/100/let-7 delivery enhances functional recovery after infarction. Heart function improvement by anti-miR treatment is sustained over long periods of time (ejection fraction) and seems to involve regeneration of the myocardial mass (LAWV thickening, immunohistological analysis shown in FIG. 25A). Ultrasound analysis shown in FIG. 25B (abbreviations AW; anterior wall; ID: internal diameter; reflects heart dilation; PW: posterior wall).

DETAILED DESCRIPTION OF THE INVENTION

Definitions

Figure 3A:
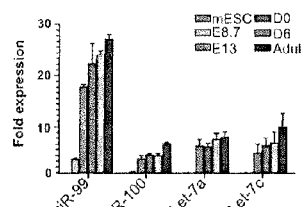
FIGS. 3A-H. Adult mammalian cardiomyocytes can be directed to a proliferative state by forced silencing of the miR-99/100 cluster. Expression patterns of the miR-99/100 cluster during development in murine (FIG. 3A) and human cardiomyocytes (FIG. 3C) were determined by qRT-PCR (n=6).
Figure 3B:
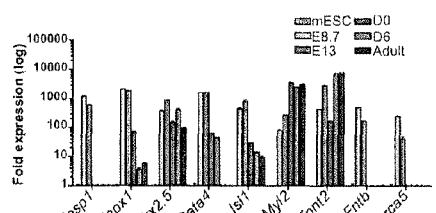
Figure 3C:
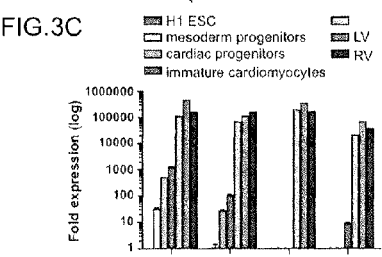
Figure 3D:
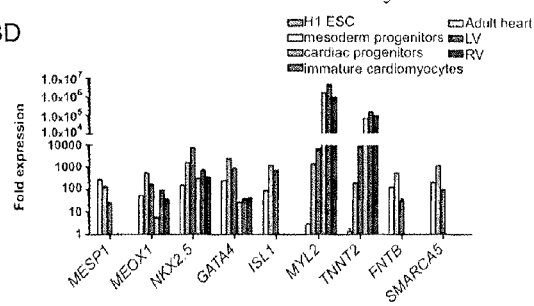
Figure 3E:
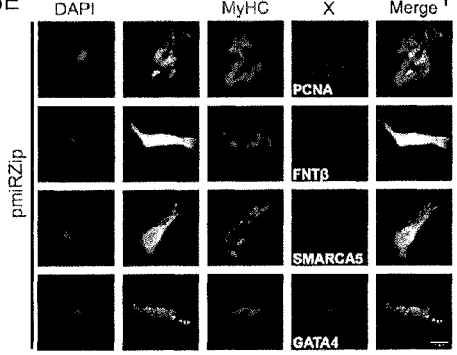
Figure 3F:
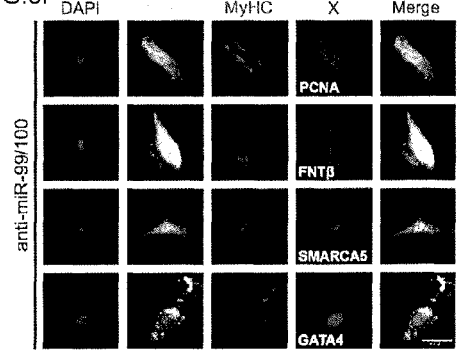

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, and 2-O-methyl ribonucleotides.

A "miRNA" or "microRNA" as provided herein refers to a nucleic acid that forms a double stranded RNA, which double stranded RNA has the ability to reduce or inhibit expression of a gene or target gene when expressed in the same cell as the gene or target gene. The complementary portions of the nucleic acid that hybridize to form the double stranded molecule typically have substantial or complete identity. In one embodiment, a microRNA refers to a nucleic acid that has substantial or complete identity to a target gene and forms a double stranded miRNA. In embodiments, the miRNA inhibits gene expression by interacting with a complementary cellular mRNA thereby interfering with the expression of the complementary mRNA. Typically, the nucleic acid is at least about 15-50 nucleotides in length (e.g., each complementary sequence of the double stranded miRNA is 15-50 nucleotides in length, and the double stranded miRNA is about 15-50 base pairs in length). In other embodiments, the length is 20-30 base nucleotides, preferably about 20-25 or about 24-29 nucleotides in length, e.g., 20, 21, 22, 23, 24, 25, 26, 27, 28, 29, or 30 nucleotides in length.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "protein", "peptide", and "polypeptide" are used interchangeably to denote an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

The terms "identical" or percent "identity," in the context of two or more nucleic acids or proteins, refer to two or more sequences or subsequences that are the same or have a specified percentage of nucleotides or amino acids that are the same (i.e., about 60% identity, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See e.g., the NCBI web site at ncbi.nlm.nih.gov/BLAST. Such sequences are then said to be "substantially identical." This definition also refers to, or may be applied to, the compliment of a test sequence. The definition also includes sequences that have deletions and/or additions, as well as those that have substitutions. Identity typically exists over a region that is at least about 50 amino acids or nucleotides in length, or over a region that is 50-100 amino acids or nucleotides in length, or over the entire length of a given sequence.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, *Molecular Cloning: A Laboratory Manual*, 18.1-18.88).

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid or protein indicates that the nucleic acid or protein comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "exogenous" refers to a molecule or substance (e.g., nucleic acid or protein) that originates from outside a given cell or organism. Conversely, the term "endogenous" refers to a molecule or substance that is native to, or originates within, a given cell or organism.

A "vector" is a nucleic acid that is capable of transporting another nucleic acid into a cell. A vector is capable of directing expression of a protein or proteins encoded by one or more genes carried by the vector when it is present in the appropriate environment.

A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

A "cell culture" is an in vitro population of cells residing outside of an organism. The cell culture can be established from primary cells isolated from a cell bank or animal, or secondary cells that are derived from one of these sources and immortalized for long-term in vitro cultures.

The terms "culture," "culturing," "grow," "growing," "maintain," "maintaining," "expand," "expanding," etc., when referring to cell culture itself or the process of culturing, can be used interchangeably to mean that a cell is maintained outside the body (e.g., ex vivo) under conditions suitable for survival. Cultured cells are allowed to survive, and culturing can result in cell growth, differentiation, or division. The term does not imply that all cells in the culture survive or grow or divide, as some may naturally senesce, etc. Cells are typically cultured in media, which can be changed during the course of the culture.

The terms "media" and "culture solution" refer to the cell culture milieu. Media is typically an isotonic solution, and can be liquid, gelatinous, or semi-solid, e.g., to provide a matrix for cell adhesion or support. Media, as used herein, can include the components for nutritional, chemical, and structural support necessary for culturing a cell.

The term "derived from," when referring to cells or a biological sample, indicates that the cell or sample was obtained from the stated source at some point in time. For example, a cell derived from an individual can represent a primary cell obtained directly from the individual (i.e., unmodified), or can be modified, e.g., by introduction of a recombinant vector, by culturing under particular conditions, or immortalization. In some cases, a cell derived from a given source will undergo cell division and/or differentiation such that the original cell is no longer exists, but the continuing cells will be understood to derive from the same source.

The term "transfection" or "transfecting" is defined as a process of introducing a nucleic acid molecule to a cell using non-viral or viral-based methods. The nucleic acid molecule can be a sequence encoding complete proteins or functional portions thereof. Typically, a nucleic acid vector, comprising the elements necessary for protein expression (e.g., a promoter, transcription start site, etc.). Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. For viral-based methods, any useful viral vector can be used in the methods described herein. Examples of viral vectors include, but are not limited to retroviral, adenoviral, lentiviral and adeno-associated viral vectors. In some aspects, the nucleic acid molecules are introduced into a cell using a retroviral vector following standard procedures well known in the art.

Expression of a transfected gene can occur transiently or stably in a host cell. During "transient expression" the transfected nucleic acid is not integrated into the host cell genome, and is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into to the host genome. During transposon-mediated insertion, the gene is positioned in a predictable manner between two transposon linker sequences that allow insertion into the host genome as well as subsequent excision.

The terms "inhibitor," "repressor" or "antagonist" or "downregulator" interchangeably refer to a substance that results in a detectably lower expression or activity level as compared to a control. The inhibited expression or activity can be 10%, 20%, 30%, 40%, 50%, 60%, 70%, 80%, 90% or less than that in a control. In certain instances, the inhibition is 1.5-fold, 2-fold, 3-fold, 4-fold, 5-fold, 10-fold, or more in comparison to a control.

The terms "therapy," "treatment," and "amelioration" refer to any reduction in the severity of symptoms, e.g., of a neurodegenerative disorder or neuronal injury. As used herein, the terms "treat" and "prevent" are not intended to be absolute terms. Treatment can refer to any delay in onset, amelioration of symptoms, improvement in patient survival, increase in survival time or rate, etc. The effect of treatment can be compared to an individual or pool of individuals not receiving the treatment, or to the same patient prior to treatment or at a different time during treatment. In some aspects, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The term "therapeutically effective amount," as used herein, refers to that amount of the therapeutic agent sufficient to ameliorate a given disorder or symptoms. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

"Subject," "patient," "individual in need of treatment" and like terms are used interchangeably and refer to, except where indicated, mammals such as humans and non-human primates, as well as rabbits, rats, mice, goats, pigs, and other mammalian species. The term does not necessarily indicate that the subject has been diagnosed with a particular disease, but typically refers to an individual under medical supervision.

Methods of Modulating Cardiomyocyte Proliferation

Provided herein are methods of modulating proliferation of a cardiomyocyte using micro RNA modulators. A micro RNA modulator as used herein refers to an agent capable of modulating the level of expression of a micro RNA (e.g. let-7a, mir 100). In some embodiments, the micro RNA modulator is encoded by a nucleic acid. In other embodiments, the micro RNA modulator is a small molecule (e.g. a chemical compound, synthetic micro RNA molecule). In some embodiments, the micro RNA modulator decreases the level of expression of a micro RNA compared to the level of expression in the absence of the micro RNA modulator. Where the micro RNA modulator decreases the level of expression of a micro RNA relative to the absence of the modulator, the micro RNA modulator is an antagonist of said micro RNA. In other embodiments, the micro RNA modulator increases the level expression of a micro RNA compared to the level of expression in the absence of the micro RNA modulator. Where the micro RNA modulator increases the level of expression of a micro RNA relative to the absence of the modulator, the micro RNA modulator is an agonist of the micro RNA.

In one aspect, a method of modulating proliferation of a cardiomyocyte is provided. The method includes (i) transfecting a cardiomyocyte with a nucleic acid encoding a micro RNA modulator, thereby forming a transfected cardiomyocyte; and (ii) allowing the transfected cardiomyocyte to divide, thereby modulating proliferation of the cardiomyocyte. In some embodiments, the nucleic acid is a lentiviral vector. In embodiments, the nucleic acid includes a nucleic acid sequence as set forth in SEQ ID NO:1124 or SEQ ID NO:1125. In some embodiments, the nucleic acid is a lentiviral vector. In embodiments, the nucleic acid includes a nucleic acid sequence as set forth in SEQ ID NO:1124 and SEQ ID NO:1125. In embodiments, the nucleic acid includes a nucleic acid sequence as set forth in SEQ ID NO:1124. In embodiments, the nucleic acid includes a nucleic acid sequence as set forth in SEQ ID NO:1125. In embodiments, the nucleic acid has the sequence as set forth in SEQ ID NO:1124 or SEQ ID NO:1125. In embodiments, the nucleic acid has the sequence as set forth in SEQ ID NO:1124. In embodiments, the nucleic acid has the sequence as set forth in SEQ ID NO:1125.

In other embodiments, the micro RNA modulator is an antagonist of a mir 99 micro RNA, a let-7a micro RNA, a mir 100 micro RNA, a mir 4458 micro RNA, a mir 4500 micro RNA or a mir 89 micro RNA. In some embodiments, the proliferation of the cardiomyocyte is increased compared to a control cardiomyocyte lacking the nucleic acid encoding said RNA modulator. In some embodiments, the micro RNA modulator is an agonist of a mir 99 micro RNA, a let-7a micro RNA, a mir 100 micro RNA, a mir 4458 micro RNA, a mir 4500 micro RNA or a mir 89 micro RNA.

In another aspect, a method of modulating proliferation of a cardiomyocyte is provided. The method includes (i) contacting a cardiomyocyte with a small molecule, thereby forming a treated cardiomyocyte; and (ii) allowing the treated cardiomyocyte to divide, thereby modulating proliferation of the cardiomyocyte. In some embodiments, the proliferation of the cardiomyocyte is increased compared to a control cardiomyocyte lacking the small molecule. In some further embodiment, the small molecule modulates expression of a mir 99 micro RNA-regulated protein, a let-7a micro RNA-regulated protein, a mir 100 micro RNA-regulated protein, a mir 4458 micro RNA-regulated protein, a mir 4500 micro RNA-regulated protein or a mir 89 micro RNA-regulated protein. In other embodiments, the small molecule is a chemical compound. In some embodiments, the small molecule is a synthetic micro RNA molecule. In embodiments, the synthetic micro RNA molecule includes a nucleic acid sequence as set forth in SEQ ID NO:1124 or SEQ ID NO:1125. In embodiments, the synthetic micro RNA molecule includes a nucleic acid sequence as set forth in SEQ ID NO:1124 and SEQ ID NO:1125. In embodiments, the synthetic micro RNA molecule includes a nucleic acid sequence as set forth in SEQ ID NO:1124. In embodiments, the synthetic micro RNA molecule includes a nucleic acid sequence as set forth in SEQ ID NO:1125. In embodiments, the synthetic micro RNA molecule has a nucleic acid sequence as set forth in SEQ ID NO:1124. In embodiments, the synthetic micro RNA molecule has a nucleic acid sequence as set forth in SEQ ID NO:1125.

In other embodiments, the proliferation of the cardiomyocyte is increased compared to a control cardiomyocyte lacking the synthetic micro RNA molecule. In some embodiments, the synthetic micro RNA molecule is an antagonist of a mir 99 micro RNA, a let-7a micro RNA, a mir 100 micro RNA, a mir 4458 micro RNA, a mir 4500 micro RNA or a mir 89 micro RNA. In other embodiments, the synthetic micro RNA molecule is an agonist of a mir 99 micro RNA, a let-7a micro RNA, a mir 100 micro RNA, a mir 4458 micro RNA, a mir 4500 micro RNA or a mir 89 micro RNA.

In another aspect, a method of treating myocardial infarction in a subject in need thereof is provided. The method includes administering to the subject a therapeutically effective amount of a nucleic acid encoding a micro RNA modulator, wherein the RNA modulator increases cardiomyocyte proliferation thereby treating the myocardial infarction. In some embodiments, the micro RNA modulator is an antagonist of a mir 99 micro RNA, a let-7a micro RNA, a mir 100 micro RNA, a mir 4458 micro RNA, a mir 4500 micro RNA or a mir 89 micro RNA. In embodiments, the micro RNA modulator is an antagonist of a mir 99 micro RNA and an antagonist of a let-7a micro RNA. In embodiments, the nucleic acid includes a nucleic acid sequence as set forth in SEQ ID NO:1124 or SEQ ID NO:1125. In embodiments, the nucleic acid includes a nucleic acid sequence as set forth in SEQ ID NO:1124. In embodiments, the nucleic acid includes a nucleic acid sequence as set forth in SEQ ID NO:1125. In embodiments, the nucleic acid includes a nucleic acid sequence as set forth in SEQ ID NO:1124 and SEQ ID NO:1125.

In embodiments, the method includes administering to the subject a therapeutically effective amount of a first nucleic acid and a second nucleic acid, wherein the first nucleic acid encodes an antagonist of a mir 99 micro RNA and the second nucleic acid encodes an antagonist of a let-7a micro RNA. In embodiments, the administering to the subject a therapeutically effective amount of a nucleic acid includes administering a first nucleic acid and a second nucleic acid, wherein the first nucleic acid encodes an antagonist of a mir 99 micro RNA and the second nucleic acid encodes an antagonist of a let-7a micro RNA.

In another aspect, a method of treating myocardial infarction in a subject in need thereof is provided. The method includes administering to the subject a therapeutically effective amount of a nucleic acid encoding an antagonist of a mir 99 micro RNA and a nucleic acid encoding an antagonist of a let-7a micro RNA, thereby treating the myocardial infarction.

In another aspect, a method of treating myocardial infarction in a subject in need thereof is provided. The method includes administering to the subject a therapeutically effective amount of a small molecule, wherein the small molecule increases cardiomyocyte proliferation thereby treating the myocardial infarction. In some embodiments, the small molecule modulates expression of a mir 99 micro RNA-regulated protein, a let-7a micro RNA-regulated protein, a mir 100 micro RNA-regulated protein, a mir 4458 micro RNA-regulated protein, a mir 4500 micro RNA-regulated protein or a mir 89 micro RNA-regulated protein. In embodiments, the small molecule modulates expression of a mir 99 micro RNA-regulated protein and a let-7a micro RNA-regulated protein. In some other embodiments, the small molecule is a chemical compound. In other embodiments, the small molecule is a synthetic micro RNA molecule. In embodiments, the synthetic micro RNA molecule includes a nucleic acid sequence as set forth by SEQ ID NO:1124 or SEQ ID NO:1125. In embodiments, the synthetic micro RNA molecule includes a nucleic acid sequence as set forth by SEQ ID NO:1124 and SEQ ID NO:1125. In embodiments, the synthetic micro RNA molecule includes a nucleic acid sequence as set forth by SEQ ID NO:1124. In embodiments, the synthetic micro RNA molecule includes a nucleic acid sequence as set forth by SEQ ID NO:1125. In some embodiments, the synthetic micro RNA molecule is an antagonist of a mir 99 micro RNA, a let-7a micro RNA, a mir 100 micro RNA, a mir 4458 micro RNA, a mir 4500 micro RNA or a mir 89 micro RNA.

EXAMPLES

Heart failure remains one of the leading causes of mortality in the developed world. Whereas the mammalian heart is endowed with certain regenerative potential, endogenous cardiomyocyte proliferation is insufficient for functional heart repair upon injury. Interestingly, non-mammalian vertebrates, such as the zebrafish, can regenerate the damaged heart by inducing cardiomyocyte dedifferentiation and proliferation. By screening regenerating zebrafish hearts Applicants identified miR-99/100 down-regulation as a key process driving cardiomyocyte dedifferentiation. Experimental down-regulation of miR-99/100 in primary adult murine and human cardiomyocytes led to an increase in the number of proliferating cardiomyocytes. AAV-mediated in vivo down-regulation of miR-99/100 after acute myocardial injury in mice induced mature cardiomyocyte proliferation, diminished infarct size and improved heart function. Applicants' study unveils conserved regenerative mechanisms between zebrafish and mammalian cardiomyocytes and represents a proof-of-concept on the suitability of activating pro-regenerative responses for healing the diseased mammalian heart.

Cardiovascular disease remains the leading cause of mortality in the developed world. Attempts at developing curative strategies have mainly focused on the activation of endogenous cardiac progenitor cells and the transplantation of in vitro-derived cardiomyocytes (A. Aguirre et al., *Cell Stem Cell* 12, 275-284 (2013); S. R. Braam et al., *Trends in pharmacological sciences* 30, 536-45 (2009)). More recently, in vivo reprogramming strategies have emerged as potential treatments for heart failure (L. Qian et al., *Nature* (2012), doi:10.1038/nature11044; K. Song et al., *Nature* 485, 599-604 (2012) A. Eulalio et al., *Nature* (2012), doi:10.1038/nature11739). Along this line, a recent report by Porrello et al. has highlighted a remarkable regenerative capacity in neonatal murine hearts upon injury (E. R. Porrello et al., *Science* (New York, N.Y.) 331, 1078-80 (2011)). Although adult mammalian cardiomyocytes retain a certain ability to proliferate (S. E. Senyo et al., *Nature*, 2-6 (2012)), endogenous regenerative responses during adulthood are largely insufficient for replenishing the lost cardiac tissue. Noticeably, heart repair can be induced upon manipulation of miRNA pathways identified as drivers of cardiomyocyte proliferation in neonatal murine models (A. Eulalio et al., *Nature* (2012), doi:10.1038/nature11739L; E. R. Porrello et al., *Circulation research* 109, 670-9 (2011)). This may suggest that the mechanisms underlying heart regeneration at birth are still present, yet dormant and/or repressed, in adult murine hearts. Other vertebrates, such as the zebrafish, are able, throughout their entire lifetime, to activate endogenous regenerative responses that lead to complete cardiomyocyte-mediated heart regeneration similar to that observed in neonatal mice (R. Zhang et al., *Nature* (2013), doi:10.1038/nature12322; K. D. Poss et al., *Science* (New York, N.Y.) 298, 2188-90 (2002); A. Raya et al., *Proceedings of the National Academy of Sciences of the United States of America* 100 Suppl, 11889-95 (2003); C. Jopling et al., *Nature* 464, 606-9 (2010); K. Kikuchi et al., *Nature* 464, 601-5 (2010)). Together, these observations led us to hypothesize on the existence of conserved pro-regenerative pathways between zebrafish and mammals (A. W. Seifert et al., *Nature* 489, 561-5 (2012)), and if present, whether they could be altered to drive terminally differentiated mammalian cardiomyocytes to a regeneration-competent state.

Figure 7A:
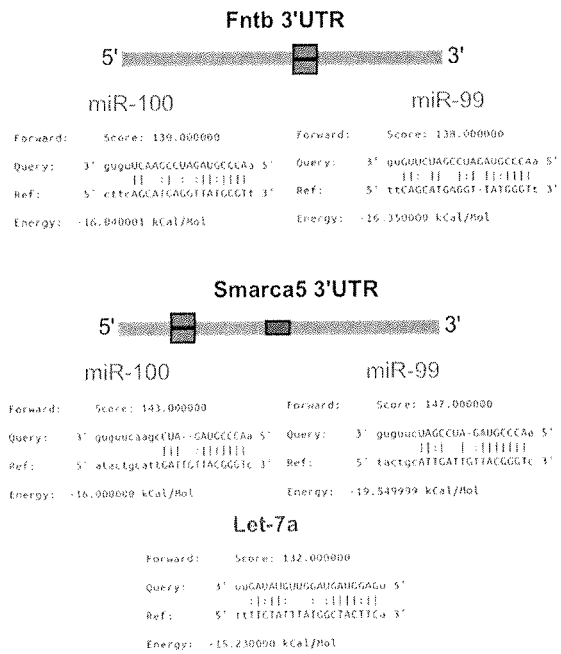
FIGs. 7A and 7B. Relevant protein targets of interest in heart regeneration regulated by miR-99/100 and Let-7a/c.
Figure 7B:
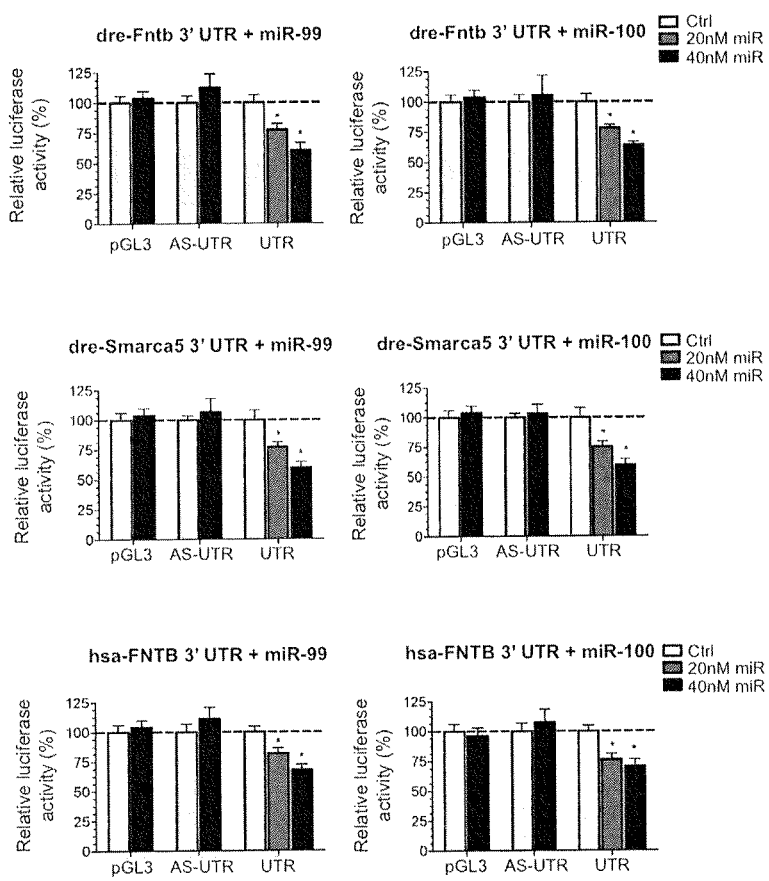
Figure 8A:
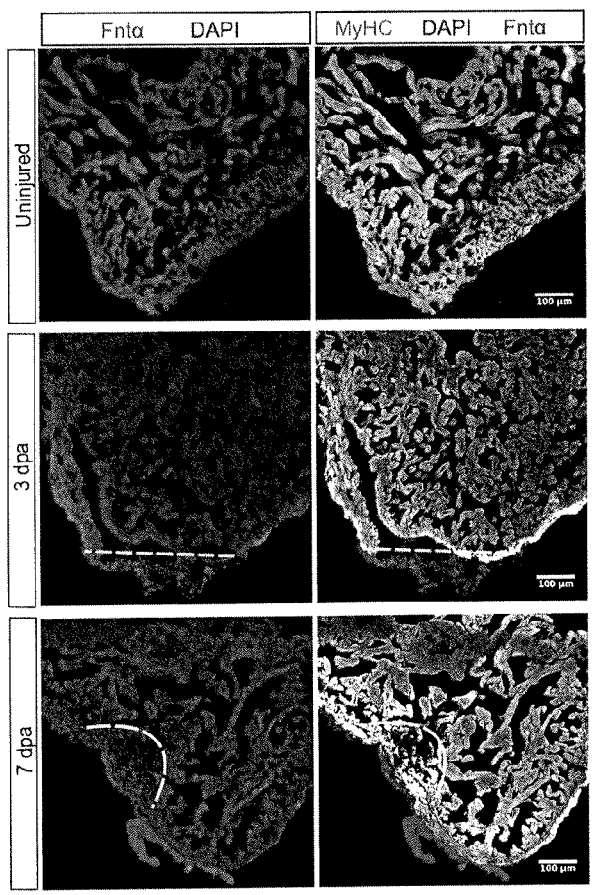
FIGS. 8A-B. Fntα, the structural subunit of Fnt, was constitutively expressed in cardiomyocytes regardless of regeneration conditions. Fntα expression was determined by immunofluorescence (FIG. 8A) and qRT-PCR (FIG. 8B, n=4). Dashed line: amputation plane. Boxed area: magnified section.
Figure 8B:
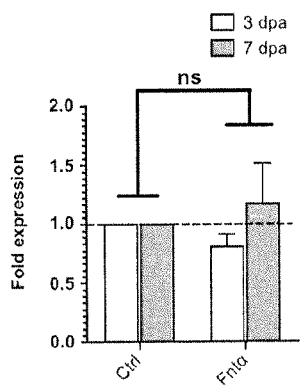
Figure 9A:
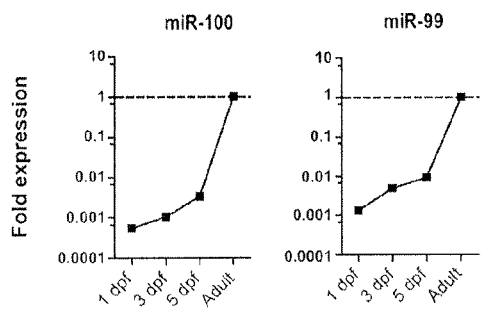
FIGS. 9A-D. MiR-99/100 plays a role in heart development.
Figure 9B:
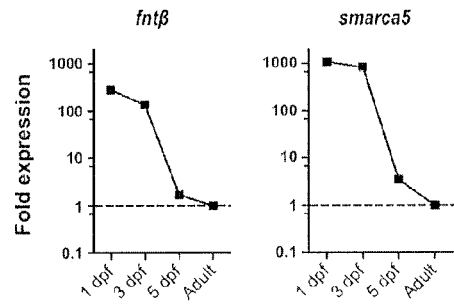
Figure 9C:
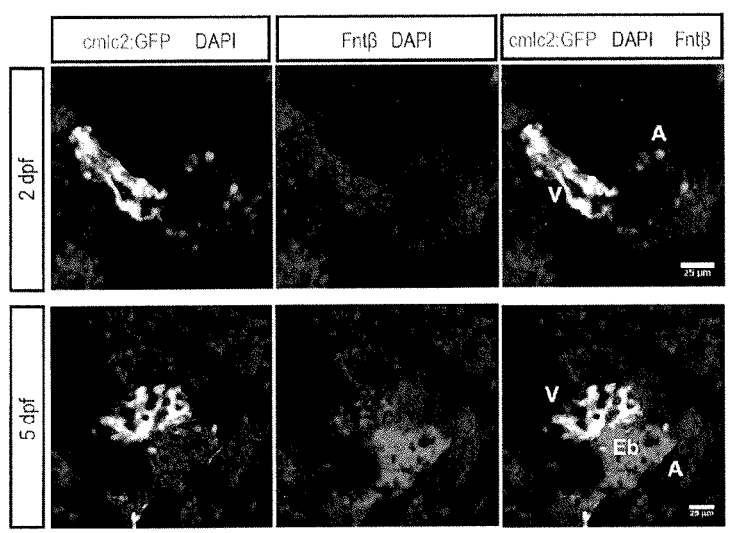
Figure 9D:
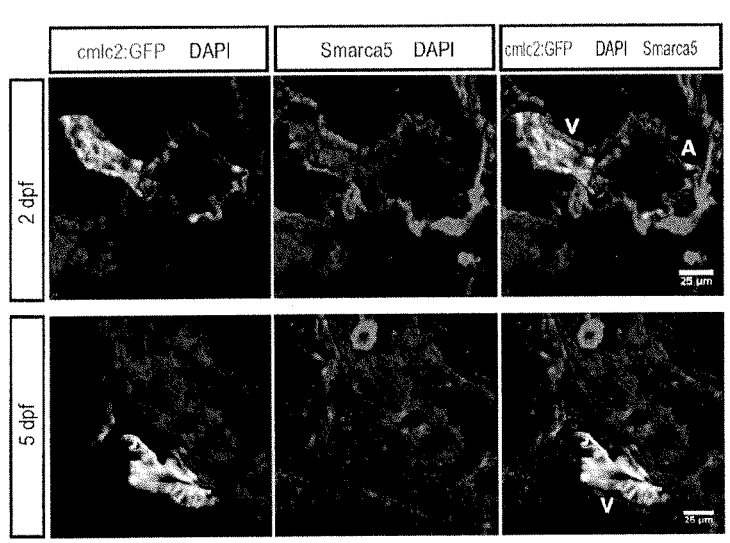
Figure 10A:
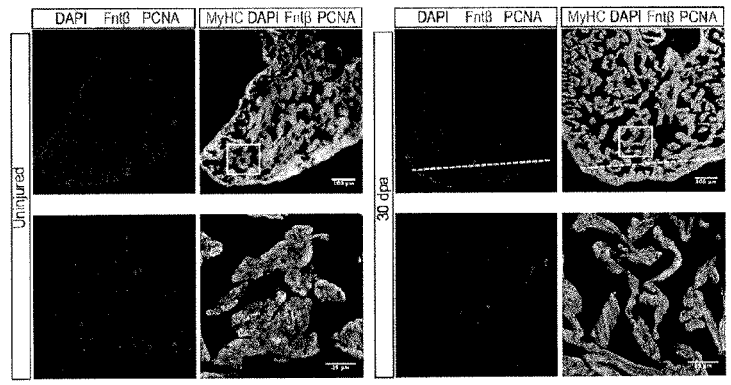
FIGS. 10A-D. Targets of miR-99/100 and Let-7a/c return to basal levels of expression after cardiomyocytes come back to their quiescent state.
Figure 10B:
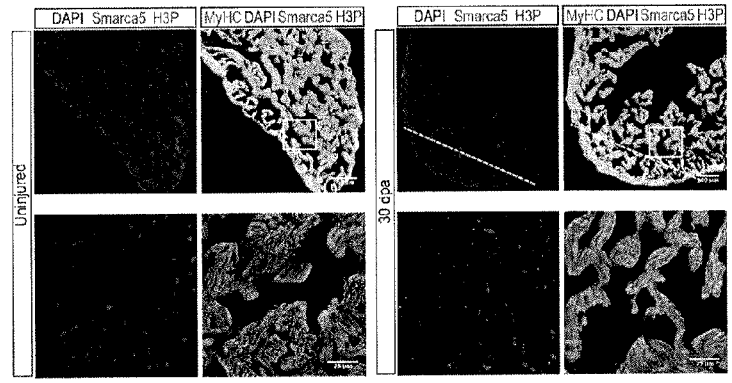
Figure 10C:
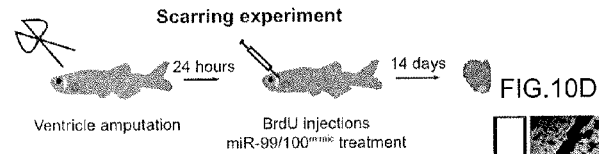
Figure 10D:
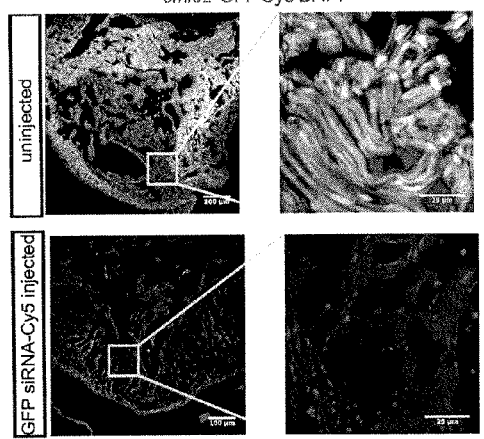

To first elucidate the presence of conserved regulatory pathways underlying regeneration Applicants decided to focus on microRNAs promoting cardiomyocyte dedifferentiation in the zebrafish. Expression of 90 microRNAs was significantly changed 3 days post amputation (dpa) of the ventricular apex (FIG. 5A). Bioinformatic analysis of signaling pathways and GO processes indicated significant enrichment in proliferation pathways, as well as processes related to chromatin remodeling (S. L. Paige et al., *Cell* 151, 221-32 (2012)), morphogenesis and kinase activity (FIG. 5B). Interestingly, two well-defined down-regulated microRNA clusters (miR-99/Let-7a and miR-100/Let-7c) were highly conserved in sequence and genomic organization across different vertebrates (FIG. 5C). Putative protein targets were also shared between zebrafish and mammals (Table S1 and Table S2). Further expression analysis demonstrated a significant down-regulation of miR-99/100 and Let-7a/c during the early regenerative stages (3-7 dpa) (FIG. 1A) in agreement with previous reports (C. Jopling et al., *Nature* 464, 606-9 (2010)). Noticeably, miR-99/100 and Let-7a/c expression (data not shown) was high and confined to cardiomyocytes in uninjured hearts, and almost undetectable upon injury (FIG. 1, B and C and FIG. 6). microRNA target prediction highlighted two proteins specifically expressed in the regenerating zebrafish heart, Fntβ (beta subunit of farnesyl-transferase) and Smarca5 (SWI/SNF-related matrix associated actin-dependent regulator of chromatin subfamily a, member 5) (FIG. 1, B to D and FIG. 6). Binding experiments confirmed miRNA targeting of the 3'UTRs in both human and zebrafish Fntβ and Smarca5 (a C. Mueller et al., 2H., *Oncogene*, 1-9 (2012)) (FIG. 7). Accompanying Fntβ up-regulation, the structural subunit of fnt (Fntα) was also expressed during heart regeneration (FIG. 8). Chemical inhibition of fnt with the specific antagonist tipifarnib significantly impaired heart regeneration by decreasing the number of proliferating cardiomyocytes (FIG. 1, E to G). Taken together, these data suggest that targets downstream of miR-99/100 play a functional role during heart regeneration.

Figure 11A:
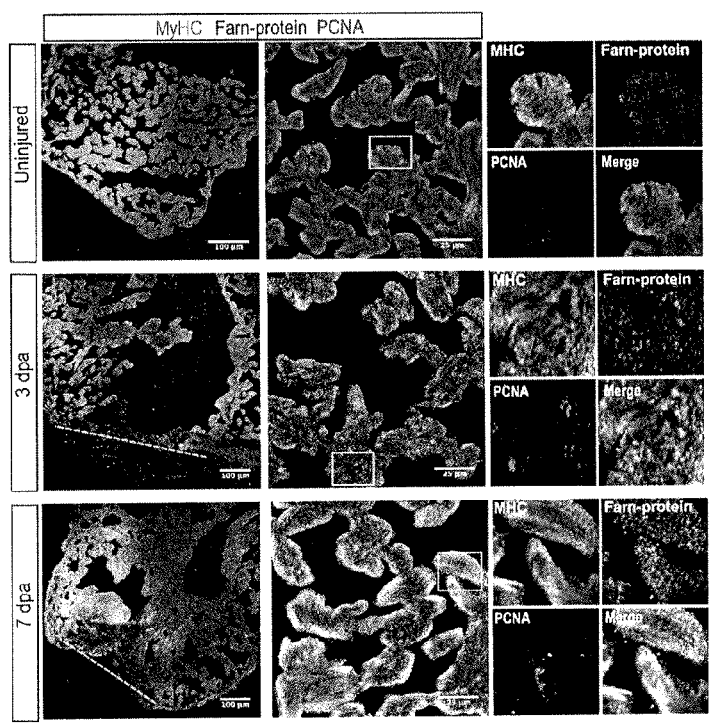
FIGS. 11A-B. Direct substrates of fnt are activated in regenerating hearts.
Figure 11B:
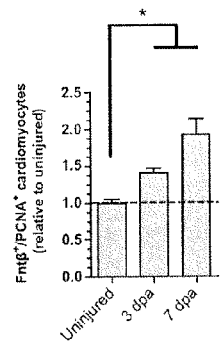
Figure 12A:
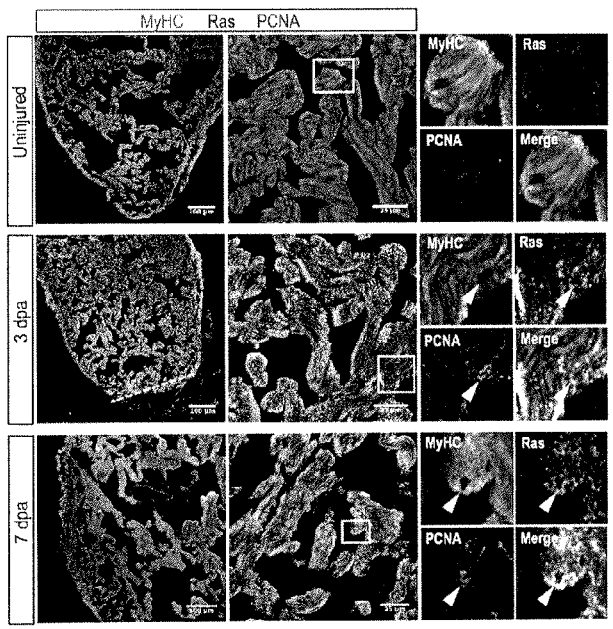
FIGS. 12A-F. Signaling downstream of fntβ in the MAPK signaling pathway were consistently up-regulated in regenerating hearts. Ras (FIGS. 12A, B, C) and c-myc (FIGS. 12D, E, F), activators of the MAPK pathway regulated by miR-99/100 and Let-7a/c were up-regulated as determined by immunofluorescence (FIGS. 12A,D) and by qRT-PCR (FIGS. 12B, C,E,F; n=5). Dashed line: amputation plane. Boxed area: magnified section. Arrowheads: cells of interest.
Figure 12B:
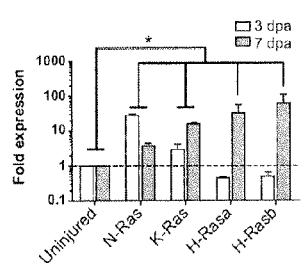
Figure 12C:
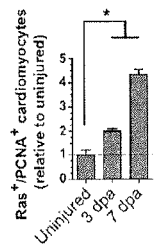
Figure 12D:
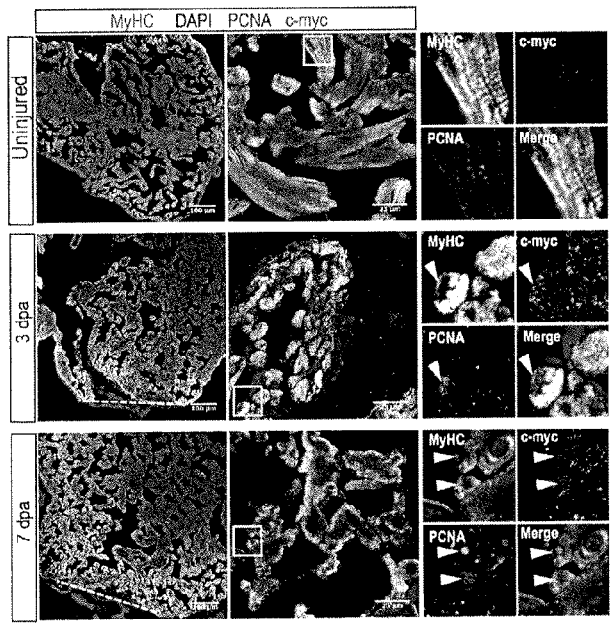
Figure 12E:
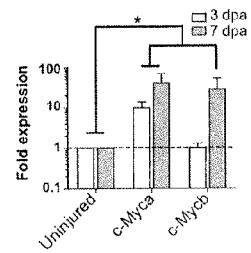
Figure 12F:
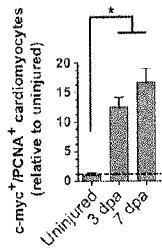
Figure 13A:
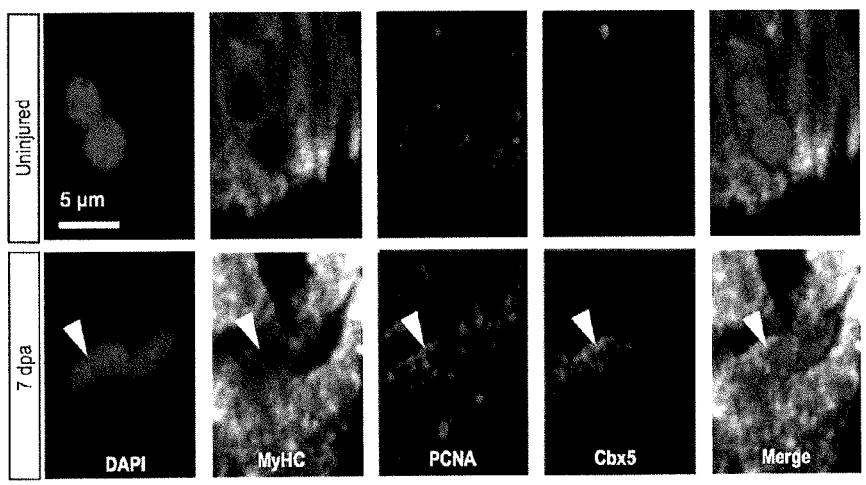
FIGS. 13A-B. Chromatin remodeling is a necessary step in cardiomyocyte dedifferentiation.
Figure 13B:
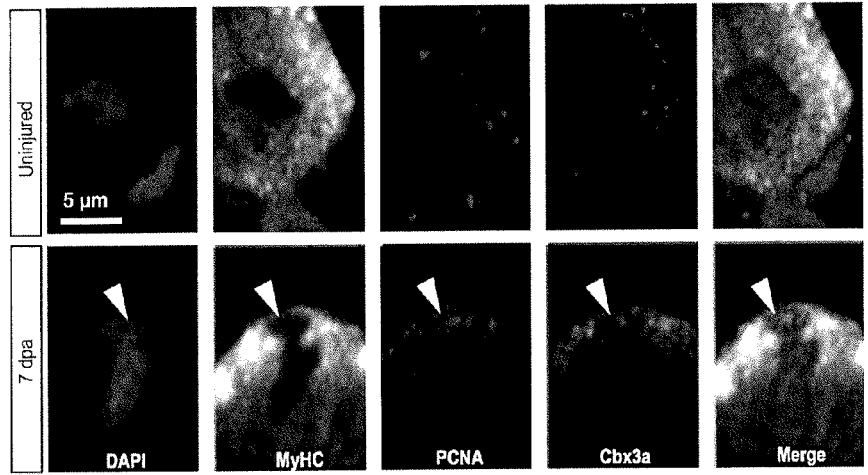
Figure 14:
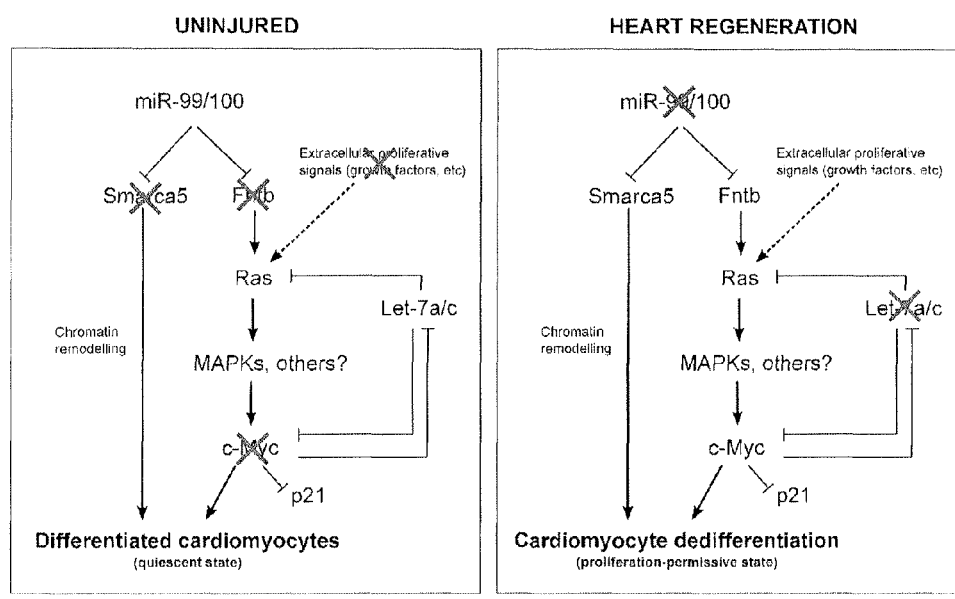
FIG. 14. Expression of miR-99/100 cluster is a switch to promote or inhibit cardiomyocyte dedifferentiation and proliferation in vertebrates. In the proposed model of action, quiescent cardiomyocytes express high levels of miR-99/100 and Let-7a/c, which inhibit the expression of key members of the proliferative activation cascade (Uninjured condition shown in left panel). Upon injury, cardiomyocytes cease to express these miRs, leading to the over-expression of key regulators of two parallel pathways simultaneously: MAPK signaling and chromatin remodeling (Injury condition shown in right panel). These changes lead to a proliferation-permissive state in cardiomyocytes, which become more receptive towards proliferative signals coming from the injured area and proliferate to replenish the lost tissue. The symbols "X" indicate blocked pathways.
Figure 15A:
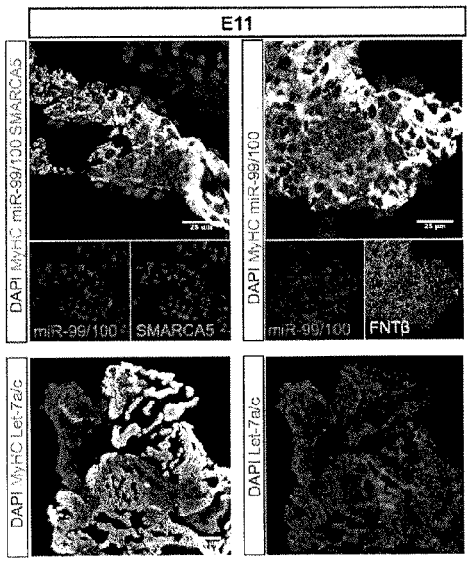
FIGS. 15A-D. FISH/IF for different developmental stages in the mouse heart.
Figure 15B:
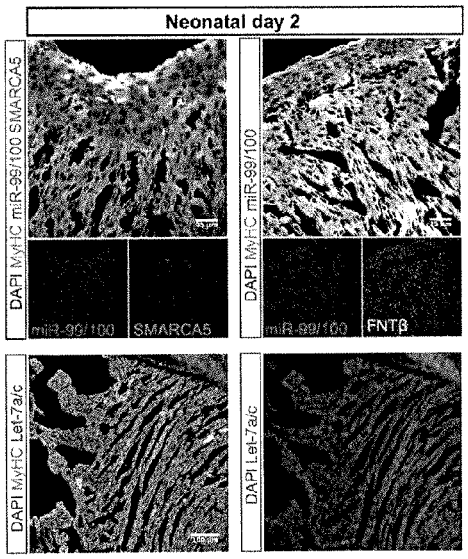
Figure 15C:
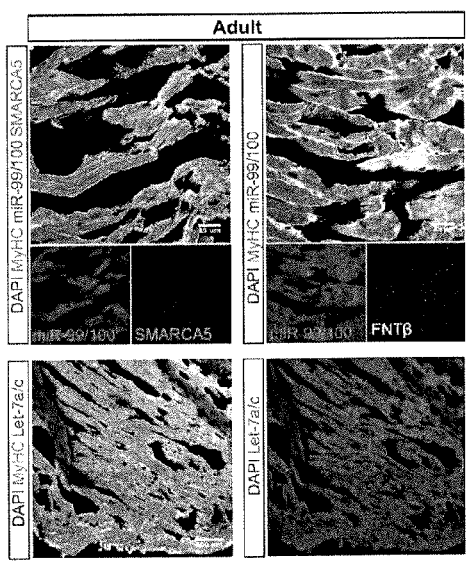
Figure 15D:
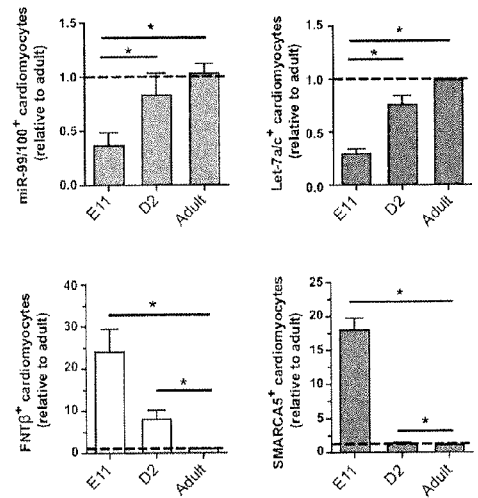

Since regeneration might be considered to a large extent redolent of development (J. P. Brockes, A. Kumar, *Annual review of cell and developmental biology* 24, 525-49 (2008); J. L. Whited, C. J. Tabin, 2-4 (2010); D. Knapp, E. M. Tanaka, *Current Opinion in Genetics & Development* (2012), doi: 10.1016/j.gde.2012.09.006) Applicants next decided to investigate the role of miR-99/100 and their target proteins Fntβ and Smarca5 during zebrafish heart development and maturation. qRT-PCR and immunofluorescence analyses demonstrated low levels of miR-99/100 expression during early heart development concomitantly with high levels of Smarca5 and Fntβ (FIG. 9). Functional analyses by injection of miR-99/100 mimics, and/or fntβ/smarca5 translation-blocking morpholinos in one-cell stage cmlc2:GFP transgenic fish embryos resulted in a significantly reduced ventricle size in spite of the presence of apparently normal heart anatomical structures (ventricle, atrium, valve) (FIG. 1, H to J). To determine if cardiomyocytes showing up-regulation of Fntβ and Smarca5 progress into a proliferative state, Applicants analyzed the expression of nuclear proliferative markers at different time points post-amputation (FIG. 2, A to D). In all cases high levels of Fntβ and Smarca5 correlated with PCNA and/or H3P expression in the nucleus. Concomitantly, disorganized sarcomeric structures were particularly evident at 7 dpa (FIG. 2, A and B). miR-99/100 expression levels, and their respective protein targets, returned to basal levels when regeneration of the ventricle was mostly complete at 30 dpa (FIG. 10, A and B). Next, Applicants designed a series of in vivo experiments to exogenously manipulate miR-99/100 levels with mimics and antagomiRs in adult regenerating animals (FIG. 10, C and D). Intra-cardiac injection of miR-99/100 mimics efficiently blocked the regenerative response in all animals tested (FIG. 2, E and F) and BrdU incorporation confirmed that cardiomyocyte proliferation was significantly disrupted in mimic-treated animals (FIG. 2G). Conversely, microRNA inhibition of size-matched sibling fish led to significantly enlarged hearts (FIG. 2, H and I). Histological analysis indicated cardiomyocyte proliferation in the absence of cardiac hypertrophy (FIG. 2J), suggesting hyperplasia as the underlying mechanism of action of miRNA-99/100. Applicants next decided to study the downstream signaling mechanisms of miR-99/100 and Let-7a/c. Applicants detected increased farnesylation as a consequence of fnt activity in regenerating hearts at 3 and 7 dpa (FIG. 11). Ras family proteins, targets of fnt, appeared up-regulated and preferentially located to the cell membrane (FIG. 12, A to C). Similarly, c-Myc, a transcription factor essential for cellular proliferation downstream of this pathway, was significantly up-regulated and localized to the cell nucleus in dedifferentiating cardiomyocytes (FIG. 12, D to F). Interestingly, Cbx5 and Cbx3a, chromatin-remodeling proteins critical in proliferating cardiomyocytes (J. K. Takeuchi et al., *Nature communications* 2, 187 (2011); N. Collins et al., *Nature genetics* 32, 627-32 (2002); S. H. Kwon, J. L. Workman, *BioEssays: news and reviews in molecular, cellular and developmental biology* 33, 280-9 (2011)), demonstrated enhanced expression at 7 dpa, when Smarca5 levels in the nucleus were highest (FIG. 13). Taken together, Applicants' results indicate that miR-99/100 down-regulation plays a role, possibly by chromatin remodeling, in the dedifferentiation process that leads to zebrafish heart regeneration (FIG. 14).

In light of the evolutionary conservation of their structures and downstream signaling pathways, Applicants wondered whether microRNA-99/100 and Let-7a/c functions would be similar between mammals and zebrafish. To this end, Applicants first analyzed microRNA-99/100 and FNTβ/SMARCA5 expression in developing and adult murine hearts. qRT-PCR and immunofluorescence analyses highlighted a progressive up-regulation of microRNA-99/100 paralleling cardiac maturation and FNTβ/SMARCA5 down-regulation (FIG. 3, A and B and FIG. 15). Analyses of human cardiomyocytes at progressive differentiation stages, including adult heart samples, demonstrated a peak in miR-99/100 expression in adult mature human cardiomyocytes, a point at which FNTβ/SMARCA5 expression was undetectable (FIG. 3, C and D). hESC-derived immature proliferative cardiomyocytes (hiCM) expressed GATA4 (a cardiac progenitor marker), FNTβ, SMARCA5 and intermediate-low levels of the identified miRNAs (FIG. 16) resembling a regenerative, proliferative state as described before (K. Kikuchi et al., *Nature* 464, 601-5 (2010), C. Jopling et al., *Nature reviews. Molecular cell biology* 12, 79-89 (2011)).

Figure 3G:
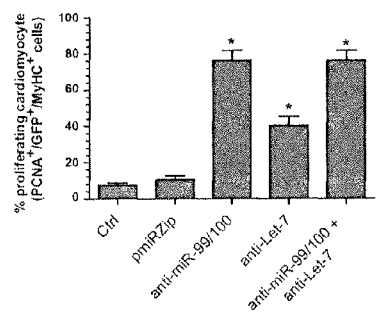
Figure 3H:
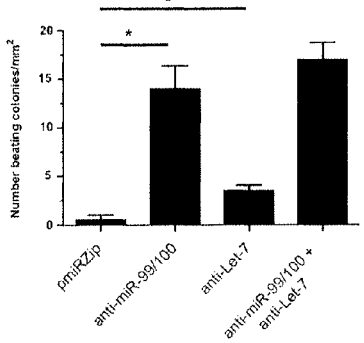
Figure 6A:
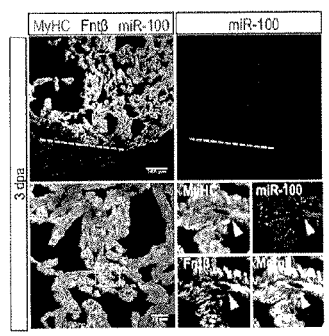
FIGS. 6A-D. Expression of miR-99/100 is restricted to cardiomyocytes and inversely correlates with Fntβ and Smarca5.
Figure 6B:
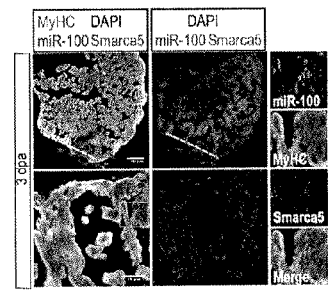
Figure 6C:
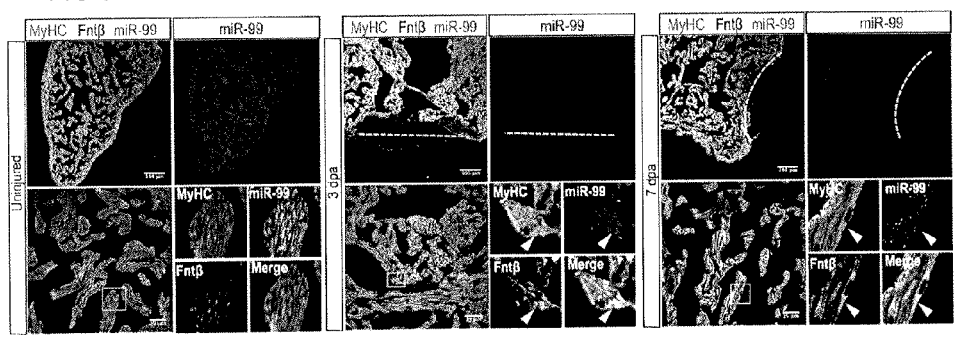
Figure 6D:
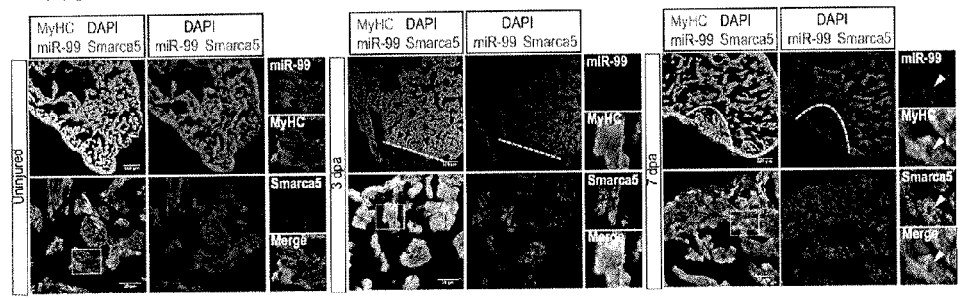
Figure 17A:
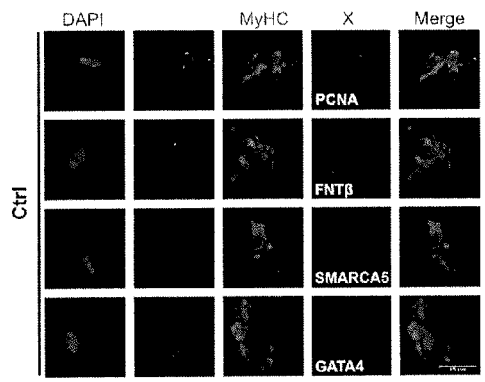
FIGS. 17A-F. miR silencing leads to dedifferentiation and proliferation of cardiomyocytes.
Figure 17B:
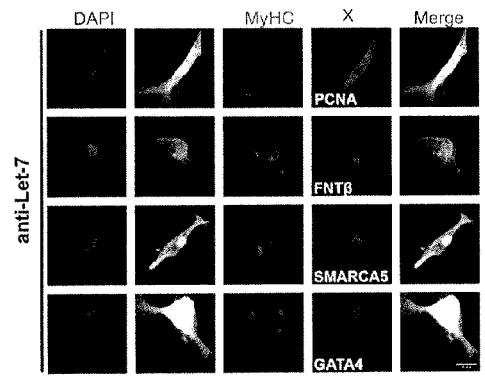
Figure 17C:
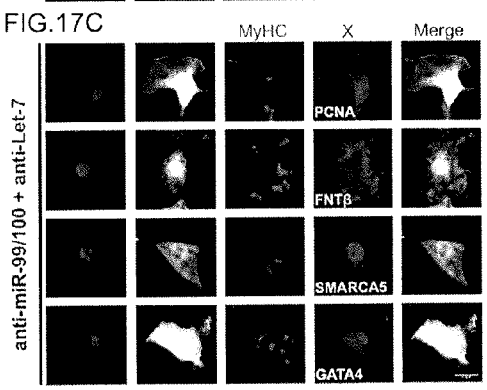
Figure 17D:
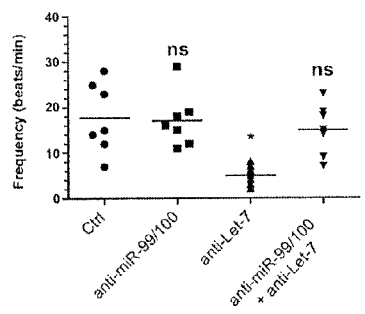
Figure 17E:
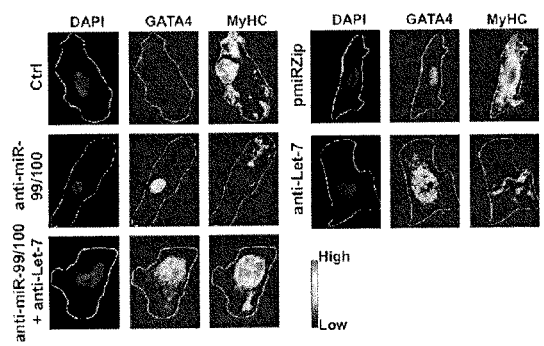
Figure 17F:
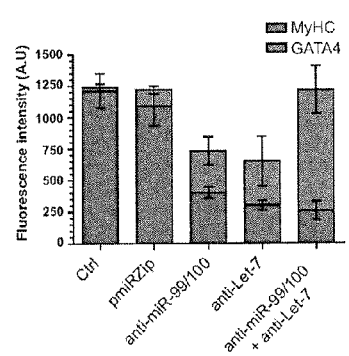
Figure 18A:
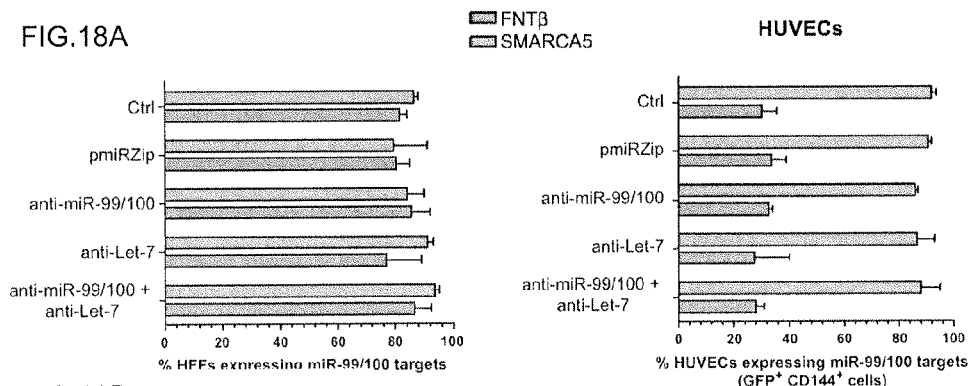
FIGS. 18A-C. microRNA silencing is specific for cardiomyocytes.
Figure 18B:
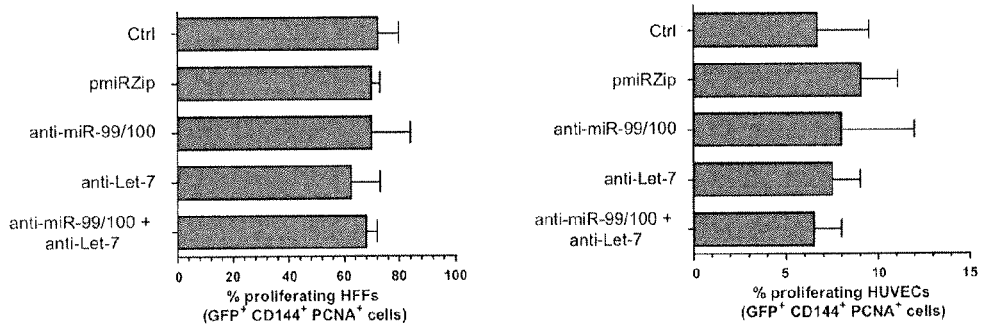
Figure 18C:
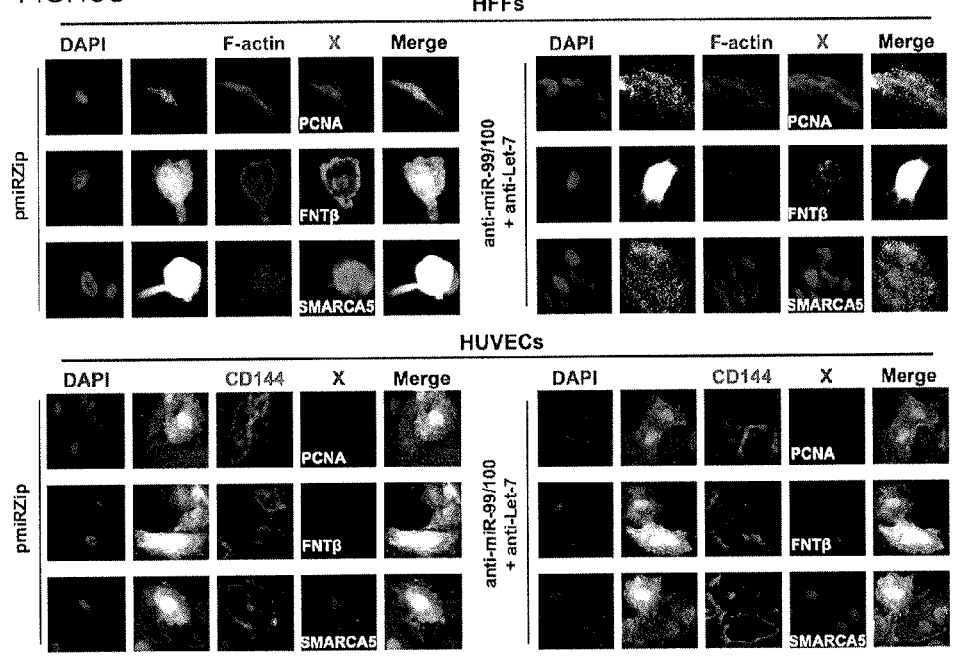
Figure 19A:
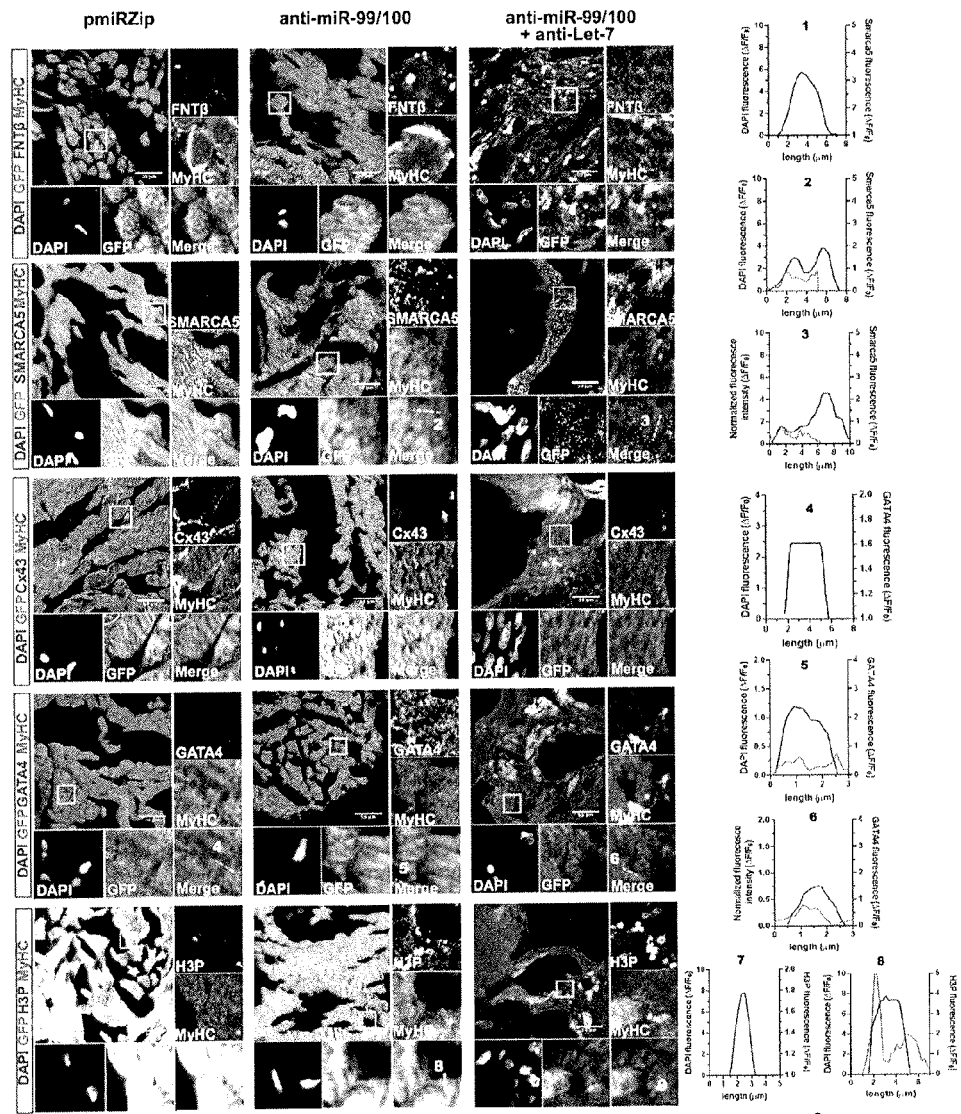
FIGS. 19A-B (from top to bottom, confocal analysis of FNTB, SMARCA5, Cx43, GATA4 and H3P). Histograms to the left represent positional information from the numbers shown in the insets. Ex vivo organotypic culture of murine myocardial tissue reveals sustained cardiomyocyte proliferation. Adult mouse heart tissue was cultured and treated with empty vector (pmiRZip), anti-miR-99/100 or both anti-miR-99/100 and anti-Let-7 (lentiviral activation was followed with a GFP reporter). Confocal analysis after 7 days of miR silencing led to significantly increased FNTβ and SMARCA5 (FIGS. 19A, B), enhanced numbers of dedifferentiated cardiomyocytes—determined by Cx43 and GATA4 expression—(FIG. 19B) and significantly increased number of proliferating cells (n=4). Dashed line and corresponding numbers: nuclear profile of representative cells. Boxed area: magnified section.
Figure 19B:
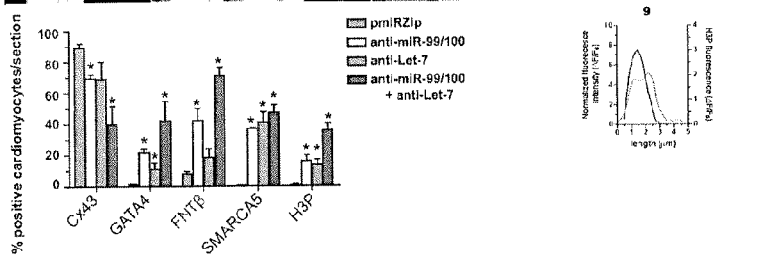
Figure 21A:
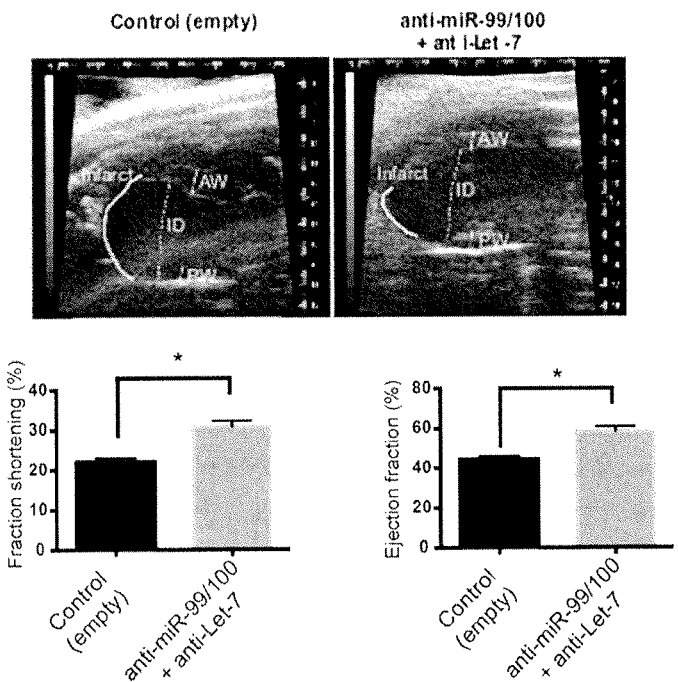
FIGS. 21A-B. Echocardiography showing functional improvement in infarcted mice treated with anti-miR-99/100 and anti-Let-7a (upper panel) and quantification of that data (lower panel). Animals were subjected to LAD artery ligation to provike infarction followed by tintramyocardial administration of antimiR containing AAV2/9 vectors. Functional heart recovery was measured versus untreated contrail animals.
Figure 21B:
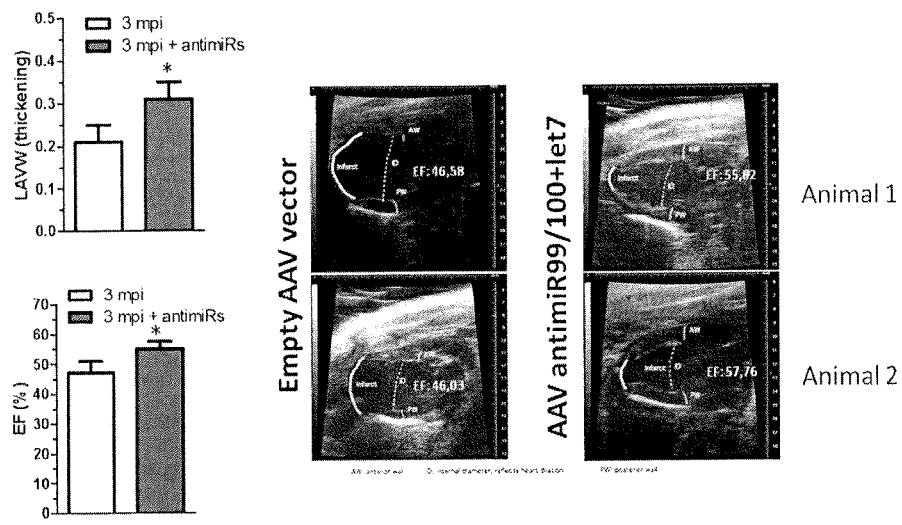
Figure 22A:
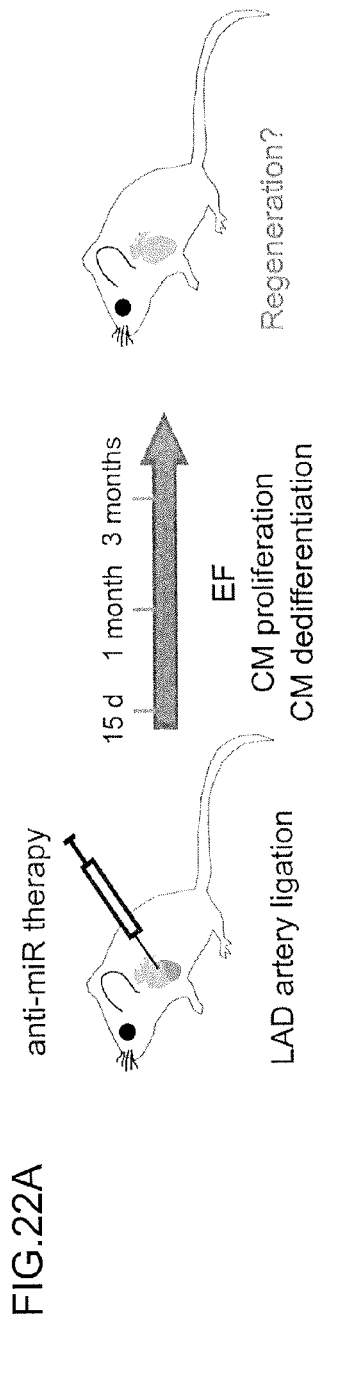
FIGS. 22A-B. In vivo regenerative reprogramming by anti-miR delivery (FIG. 22A). In vivo-induced cardiomyocyte proliferation by anti-miR delivery (18 days post-infarction) (left panels, PCNA and H3P staining showing proliferating cardiomyocytes; right panel, quantification of the data) (FIG. 22B).
Figure 22B:
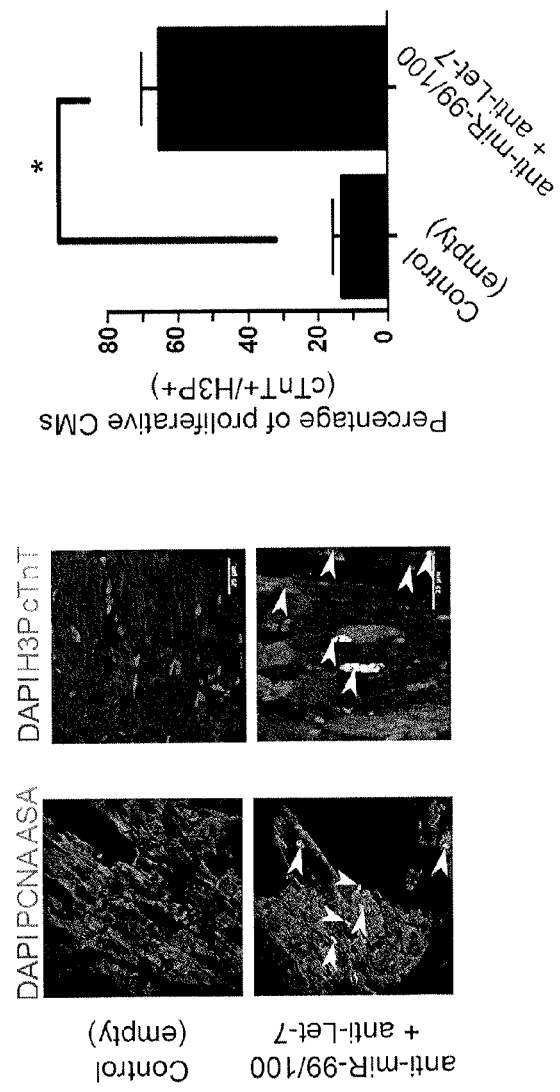

Applicants next sought to evaluate the effects of microRNA down-regulation in adult murine cardiomyocytes. Seven days after shRNA-mediated microRNA silencing significant up-regulation of SMARCA5 and FNTβ was observed accompanied by an increased amount of cardiomyocytes with disorganized sarcomeric structures and immature morphology (FIG. 3, E and F and FIG. 17, A to C). Further analysis demonstrated enhanced proliferation paralleling GATA4 and PCNA re-expression (FIG. 3, E to G and FIG. 17). These effects were more pronounced when miR-99/100 and Let-7a/c were simultaneously blocked (FIG. 3G and FIG. 17). Similarly, microRNA silencing in human cardiomyocytes resulted in increased proliferation and higher numbers of beating colonies (FIG. 3, G and H and Videos 1 to 5). Functional analyses demonstrated minimal changes in the beating rate before and after anti-miR delivery (FIG. 17D). Indicative of cardiomyocyte specificity, microRNA down-regulation did not affect proliferation or FNTβ/SMARCA5 expression in human fibroblasts or vascular cells (FIG. 18). Organotypic cultures of adult murine hearts, a setting more closely resembling physiological conditions (M. Brandenburger et al., *Cardiovascular research* 93, 50-9 (2012)), demonstrated low to undetectable levels of FNTβ/SMARCA5 (FIG. 19). Delivery of anti-miR-99/100 and/or anti-miR-Let-7 to murine heart organotypic slices resulted in cardiomyocyte proliferation as demonstrated by down-regulation of MyHC as well as re-expression of GATA4 and H3 phosphorylation (FIG. 19). Ultrastructural electron microscopy analysis confirmed cytoskeletal disassembly (FIG. 4A). Further supporting these observations, Connexin 43 (Cx43), an essential component of coupling GAP junctions in cardiomyocytes, was profoundly down-regulated (FIG. 19). Next, Applicants mimicked tissue ischemia and heart damage in organotypic slices to determine the effects of the treatment upon injury (FIG. 20A). Control organotypic slices developed necrotic areas accompanied by marginal proliferation under hypoxic conditions whereas anti-microRNA delivery resulted in reduced necrosis (FIG. 20B to D) and the appearance of proliferative cardiomyocyte populations (FIG. 4B and FIG. 20D).

Lastly, Applicants decided to test the efficacy of anti-microRNA delivery for the induction of regeneration in a murine model of myocardial infarction. Following LAD artery ligation, anti-miR-99/100 and anti-Let-7 were administered by injection of serotype 9 adeno-associated viral (AAV) particles, specifically targeting the cardiomyocyte population, in the periphery of the infarcted area. 18 days after treatment, both ejection fraction and fractional shortening significantly improved in the treated group (FIG. 4, C to F). Reduced fibrotic scarring and infarct sizes were readily observed three weeks after LAD artery ligation, indicative of an underlying regenerative response (FIG. 4G). Treated animals exhibited increased numbers of FNTβ/SMARCA5 positive cardiomyocytes, as well as a marked increase of cardiomyoctes re-expressing GATA4. PCNA and H3P staining demonstrated increased DNA synthesis and cardiomyocyte mitosis (FIG. 4, H to L). Of note, the number of mitotic cardiomyocytes was higher in areas of trabeculated muscle as opposed to the myocardium proper. Taken together, all these observations indicate that anti-miR delivery in adult murine cardiomyocytes suffices for the induction of a pro-regenerative proliferative response towards repairing a damaged heart.

These observations constitute a proof-of-concept on how animal models naturally capable of regeneration can be used for the identification of regenerative factors that may, subsequently, be applied to mammals. Experimental manipulation of conserved microRNAs unveiled during adult zebrafish heart regeneration led to similar responses in mice after heart infarction (replenishment of the lost cardiac tissue and inhibition of scar formation). In vivo activation of conserved cardiac regenerative responses may help to circumvent many of the problems associated with heart cell transplantation as well as those associated with reprogramming technologies (A. Aguirre et al., *Cell Stem Cell* 12, 275-284 (2013), M. a. Laflamme, C. E. Murry, *Nature* 473, 326-335 (2011)), serving as an additional tool to the clinical armamentarium of regenerative medicine towards the treatment of human heart disease (K. R. Chien et al., *Journal of molecular and cellular cardiology* 53, 311-3 (2012)).

Experimental Procedures

Detailed experimental procedures can be found in Supplementary information.

Animals. Wild-type zebrafish (AB) and cmlc2:GFP were maintained at 28.5° C. by standard methods, unless otherwise indicated. All protocols were previously approved and performed under institutional guidelines.

Culture and isolation of adult mouse ventricular myocytes. Wild-type mice (C57B6/J) were sacrificed and hearts were quickly recovered and washed with ice-cold $Ca^{2+}$-free ModifiedTyrode's Solution (MTS). Ventricles were dissected from the rest of the heart and subjected to enzymatic digestion (Liberase DH, Roche) for 10-15 min in a spinner flask at 37 C under continuous agitation. Afterwards cells were pelleted by short centrifugation, resuspended in KB solution and cardiomyocytes were left to sediment by gravity, thus greatly reducing the presence of other contaminating cell types. Calcium was restore to 1 mM in a step-wise fashion in three gradual steps and subsequently cardiomyocytes were centrifuged, resuspended in culture medium (IMDM 5%, 1% Pen/Strep, 0.1 ng/ml FGFb, 1 ng/ml TGF-β3) and seeded in laminin-coated tissue-culture plates. Cells were kept in culture for 1 week.

Lentiviral and AAV constructs. Anti-miR constructs, miRZip-99/100 and miRZip-let7 (SBI), were used according to the manufacturer instructions. As respective controls, the anti-miRs were removed from the parent vector by digesting with BamHI and EcoRI, end filled and re-ligated. Lentiviruses were packaged by transfecting in 293T cells followed by spinfection in the respective mouse or human ES derived cardiomyocytes. AAVs were generated as described before (Eulalio et al, 2012). Briefly, the antimiR constructs contained in the miRZip vectors were excised and ligated into pZacf-U6-luc-ZsGreen. Serotype 9 AAVs were packaged by transfection of 293T cells with the appropriate plasmids.

Organotypic Heart Slice Culture. Mice ventricles were washed in cold Modified Tyrode's Solution, embedded in 4% low melting point agarose and immediately cut into 300 μm slices using a vibratome (Leica). Heart slices were then maintained in complete IMDM 5%, 1% Pent/Strep in 12-well plates at the medium-air interface using 0.4 μm membrane transwells (Corning) at 37 C in a 5% $CO_2$ incubator. For experimental hypoxia-like conditions, slices were kept in a hypoxia chamber incubator for 4 hours at 37 C, 5% $O_2$. Lentiviral transduction was performed by immersion of the slices in virus-containing medium for 24 h.

Myocardial Infarction. Myocardial infarction was induced CD1 mice (8-12 weeks old) by permanent left anterior descending (LAD) coronary artery ligation. Briefly, mice were anesthetized with an injection of ketamine and xylazine, intubated and placed on a rodent ventilator. Body temperature was maintained at 37° C. on a heating pad. After removing the pericardium, a descending branch of the LAD coronary artery was visualized with a stereomicroscope and occluded with a nylon suture. Ligation was confirmed by the whitening of a region of the left ventricle. Recombinant AAV vectors, at a dose of $10^{11}$ viral genome particles per animal, were injected immediately after LAD ligation into the myocardium bordering the infarct zone (single injection), using an insulin syringe with incorporated 30-gauge needle. Three groups of animals were studied, receiving AAV9-control (shRNA-Luc), AAV9-antimiR-99/100 or AAV9-anti-Let-7a/c. The chest was closed, and the animals moved to a prone position until the occurrence of spontaneous breathing. BrdU was administered intraperitoneally (500 µg per animal) every 2 days, for a period of ten days. Echocardiography analysis was performed at days 12, 30 and 60 after infarction, as described below, and hearts were collected at 12 (n=6 animals per group) and 60 (n=10 animals per group) days after infarction.

Echocardiography Analysis. To evaluate left ventricular function and dimensions, transthoracic two-dimensional echocardiography was performed on mice sedated with 5% isoflurane at 12, 30 and 60 days after myocardial infarction, using a Visual Sonics Vevo 770 Ultrasound (Visual Sonics) equipped with a 30-MHz linear array transducer. M-mode tracings in parasternal short axis view were used to measure left ventricular anterior and posterior wall thickness and left ventricular internal diameter at end-systole and end-diastole, which were used to calculate left ventricular fractional shortening and ejection fraction.

Heart Collection and Histological Analysis. At the end of the studies, animals were anaesthetized with 5% isoflurane and then killed by injection of 10% KCl, to stop the heart at diastole. The heart was excised, briefly washed in PBS, weighted, fixed in 10% formalin at room temperature, embedded in paraffin and further processed for histology or immunofluorescence. Haematoxylin-eosin and Masson's trichrome staining were performed according to standard procedures, and analysed for regular morphology and extent of fibrosis. Infarct size was measured as the percentage of the total left ventricular area showing fibrosis.

Zebrafish Heart Amputation. Adult fish were anaesthetized in 0.4% Tricaine and secured, ventral side uppermost, in a slotted sponge. Watchmaker forceps were used to remove the surface scales and penetrate the skin, muscle and pericardial sac. Once exposed, the ventricle was gently pulled at the apex and cut with iridectomy scissors. After surgery, fish were immediately returned to system water.

Cryosectioning. At the specified time points, hearts were removed, washed in PBS-EDTA 0.4% and fixed for 20 min in 4% paraformaldehyde at 4° C. Afterwards, they were washed several times in PBS, equilibrated in 30% sucrose, and then frozen for cryosectioning. 10 µm slices were obtained with a cryostat (Leica).

Real Time RT-PCR. For RNA, tissue was obtained from adult heart ventricles from different time points and conditions, extensively washed in PBS-EDTA 0.4% to remove blood, and then mechanically homogenized and processed using RNeasy kit (Qiagen) as per manufacturer's instructions. RT and PCR were performed using Quantitect Reverse Transcription Kit (Qiagen) and Quantitect Primers for the following genes: Fntb, Fntα, Smarca5, myc-a, myc-b, H-rasa, H-rasb, N-ras, K-ras, tnnt2. For miRNAs, small RNA (<200 pb) was obtained employing the miRNeasy mini kit (Qiagen) using the same procedure as before. RT and PCR reactions were carried out employing miRCURY LNA RT and PCR kits (Exiqon) and stem-loop LNA primers (Exiqon).

MicroRNA microarrays. RNA was obtained as for PCR applications. GenechipmiRNA 2.0 microarrays were purchased from Affymetrix and small RNA labeling was performed using FlashTag HSR labeling kit (Genesphere). 200 ng of small RNA was polyA-tailed and biotin conjugated. After labelling, RNA was hybridized using GeneChip reagents (Affymetrix) and protocols as indicated by the manufacturer. The chip contains hybridization probes for the miRbase v15 annotations, including 248 zebrafishmiRNAs. MicroRNA data was analyzed by using the R package.

Bioinformatic Analysis of miRNA Targets. Signaling pathways and downstream target prediction related to the identified miRNAs were determined by using DIANA, Miranda and TargetScan. Gene ontology analysis was performed with DAVID software.

Fluorescence In Situ Hybridization. 10 µm heart slices were further fixed in 4% PFA for 10 min at room temperature, washed in PBS and acetylated for 10 min in acetylation solution. After washing in PBS, samples were treated with proteinase K, prehybridized for 4 h and hybridized overnight at the appropriate temperature with LNA DIG-labeled probes for the corresponding miRNAs (Exiqon). The next day slides were washed and immunolabeled with anti-DIG-alkaline phosphatase antibodies (1:2,000) and antibodies against cardiomyocytic proteins of interest (1:100) overnight at 4° C. Secondary antibody incubation was performed as for immunofluorescence experiments. Alkaline phosphatase activity was detected by incubating samples in a Fast Red solution (Dako) for 2 hours. Samples were then washed, mounted in Vecta-shield and imaged in a confocal microscope. Fast Red fluorescence was detected with Cy3 settings.

Immunofluorescence. Tissue slices were fixed for 15 min in 4% paraformaldehyde, washed in PBS-gly 0.3 M, and blocked in PBS-10% donkey serum, 0.5% TX-100, 0.5% BSA for 1 hour. Primary antibodies were diluted at the appropriate concentrations in PBS-1% donkey serum, 0.5% TX-100, 0.5% BSA and incubated overnight. After washing, slices were incubated overnight with secondary antibodies, washed and mounted in Vecta-shield. Antibodies employed are listed in table S3.

Cell Culture. COS7 cells were maintained in DMEM (high glucose) supplemented with 10% FBS, L-Glutamine and non-essential amino acids (Invitrogen). Human ES cells, H1 and H9 (WA1 and WA9, WiCell), were cultured in chemically defined hES/hiPS growth media, mTeSR1 on growth factor reduced matrigel (BD biosciences) coated plates. Briefly, 70-80% confluent hES/iPS cells were treated with dispase (Invitrogen) for 7 minutes at 37° C. and the colonies were dispersed to small clusters and lifted carefully using a 5 ml glass pipette, at a ratio of ~1:4.

Culture and Isolation of Adult Mouse Ventricular Myocytes. Wild-type mice (C57B6/J) were sacrificed and hearts were quickly recovered and washed with ice-cold $Ca^{2+}$-free ModifiedTyrode's Solution (MTS). Ventricles were dissected from the rest of the heart and subjected to enzymatic digestion (Liberase DH, Roche) for 10-15 min in a spinner flask at 37 C under continuous agitation. Afterwards cells were pelleted by short centrifugation, resuspended in KB solution and cardiomyocytes were left to sediment by gravity, thus greatly reducing the presence of other contaminating cell types. Calcium was restore to 1 mM in a step-wise fashion in three gradual steps and subsequently cardiomyocytes were centrifuged, resuspended in culture medium (IMDM 5%, 1% Pen/

Strep, 0.1 ng/ml FGFb, 1 ng/ml TGF-β3) and seeded in laminin-coated tissue-culture plates. Cells were kept in culture for 1 week.

Differentiation of Human ES Cells to Immature Cardiomyocytes. Human ES cells grown on matrigel dots (BD biosciences) were carefully dissociated using dispase and were plated on low attachment plates in EB media (IMDM, 20% FBS, 2.25 nM L-Glutamine and non-essential aminoacids). After 6 days of suspension in culture, the EBs were seeded on gelatin-coated plates in EB media. Spontaneously beating EBs were manually picked and used for further analysis. For directed differentiation, human ES cells grown in mTeSR on matrigel coated plates were treated with 12 µM GSK3β inhibitor CHIR 99021 (Stemgent) in cardiomyocyte differentiation base media (RPMI 1640 supplemented with 125 µg/ml human holo-transferrin (Sigma-Aldrich)) for 24 hours, followed by 24 hour of rest in the base media. On day 3, the cells were treated with 5 µM WNT inhibitor, IWP4 (Stemgent) for 48 hours, followed by treatment with Cardiac differentiation base media supplemented with 20 µg/ml human Insulin (SAFC) until colonies started beating.

Lentiviral Constructs. Anti-miR constructs, miRZip-99/100 and miRZip-let7 (SBI), were used according to the manufacturer instructions. As respective controls, the anti-miRs were removed from the parent vector by digesting with BamHI and EcoRI, end filled and re-ligated. Lentiviruses were packaged by transfecting in 293T cells followed by spinfection in the respective mouse or human ES derived cardiomyocytes.

Luciferase Constructs and microRNA Binding Validation. 3' UTR of human and zebrafish FNTB and SMARCA5 were amplified with the indicated primers using genomic DNA as a template and were cloned into PGL3 vector (Promega) at the XhoI site downstream of luciferase gene. COS7 cells (seeded at $3\times10^4$ cells per well of a 12 well plate and grown for 24 hours) were transfected with 50 ng each of indicated luciferase reporter vectors, pRL TK (Renilla luciferase control vector, Promega) either in the presence or absence of 20 nM or 40 nM of double stranded DNA oligonucleotide mimics of miR-99 or miR-100 (Dharmacon) using Lipofectamine (Invitrogen) following manufacturer's protocol. 12-16 hours post-transfection, cells were lysed using passive lysis buffer (Promega). Luminescent signals arising from the cell lysates obtained 12 hours post transfection of COS7 cells with appropriate luciferase constructs were measured using the Dual Luciferase assay system (Promega) in a Synergy H1 hybrid reader (BioTek). The relative luminescence intensity of each sample was calculated after normalization with corresponding Renilla luciferase activity, and were represented as % values compared to the corresponding sample without the miR mimic.

Confocal Microscopy. Samples were imaged using a Zeiss L710 confocal microscope. For every sample, at least two different fields were examined at two different magnifications (using a 20× objective and a 63× oil-immersion objective). Z-stacks were obtained for further analysis and 3D reconstruction. For intensity comparison purposes, images were taken with the same settings (pinhole size, laser intensity, etc).

Organotypic Heart Slice Culture. Mice ventricles were washed in cold Modified Tyrode's Solution, embedded in 4% low melting point agarose and immediately cut into 300 µm slices using a vibratome (Leica). Heart slices were then maintained in complete IMDM 5%, 1% Pent/Strep in 12-well plates at the medium-air interface using 0.4 µm membrane transwells (Corning) at 37 C in a 5% $CO_2$ incubator. For experimental hypoxia-like conditions, slices were kept in a hypoxia chamber incubator for 4 hours at 37 C, 5% $O_2$. Lentiviral transduction was performed by immersion of the slices in virus-containing medium for 24 h.

Morpholino and microRNA Injections in Zebrafish Embryos. Morpholinos (Gene Tools) were dissolved in water at a 2 mM stock concentration and diluted to a 2 ng/nl working concentration in PBS/phenol red solution. Embryo injections were performed by injecting ~1 nl morpholino solution at the 1-cell stage using a FemtoJet (Eppendorf). For microRNA mimic injection, a miR-99/100 equimolar mixture at 2 ng/nl in PBS was employed. Morphants were evaluated at 24, 48 and 72 h in a StereoLumar stereoscope (Zeiss).

In Vivo microRNA Delivery. MicroRNA siRNA mimics without chemical modifications were purchased from Life Technologies, dissolved in nuclease-free water and complexed to jetPEI (10 N/P ratio) for in vivo, intra-cardiac administration. 0.2 µg siRNA was injected per animal every 2 days. To determine the efficiency of the delivery, a control Cy5-labeled siRNA directed against GFP was used in cmlc2: GFP animals. MicroRNA inhibitors against the miR-99/100 family were purchased from Exiqon and used at 0.2 µg siRNA per animal every 2 days.

Tipifarnib Injections. Tipifarnib was dissolved in DMSO at 10 mg/ml and 2 µl were administered by intraperitoneal injection (final concentration 0.02 mg/animal) every 2 days for 14 days. Control animals were administered DMSO.

BrdU Labeling. Fish were anaesthetized in 0.4% Tricaine, and 10 µl of a 10 mg/ml solution of BrdU (in PBS) was injected into the abdominal cavity once every 2 days for 14 days. At that point, hearts were removed and fixed overnight in 4% paraformaldehyde at 4° C., washed in PBS, equilibrated in 30% sucrose in PBS and frozen for cryosectioning.

Histology and Histomorphometry. Masson's trichrome staining was performed in 10 µm tissue slices by immersion in Bouin's fixative followed by sequential incubation in Weigert's hematoxylin, Acid Fuchsin, phosphotungstic/ phosphomolybdic acid, Aniline Blue and acetic acid. After washes, slices were mounted for bright field observation. Histomorphometric measurements were performed with Fiji. Injured areas were quantified in four independent different slices per animal (four animals were used per condition) and normalized to whole tissue area.

Statistical Analysis. Results are expressed as mean±SEM. Statistical significance was determined by Student's t-test. Results are representative of at least 3 independent experiments except when otherwise indicated.

TABLE S1

| | miR-99/100 predicted targets | | | | | | |
|---|---|---|---|---|---|---|---|
| Target gene | Representative transcript | SEQ ID NO: | Gene name | Representative miRNA | Total context + score | Aggregate PCT | Publication (s) |
| FGFR3 | NM_000142 | 1 | fibroblast growth factor receptor 3 | hsa-miR-99a | −0.47 | <0.1 | 2005, 2007, 2009 |
| IGF1R | NM_000875 | 2 | insulin-like growth factor 1 receptor | hsa-miR-100 | −0.26 | <0.1 | 2007, 2009 |

TABLE S1-continued miR-99/100 predicted targets

| Target gene | Representative transcript | SEQ ID NO: | Gene name | Representative miRNA | Total context + score | Aggregate PCT | Publication(s) |
|---|---|---|---|---|---|---|---|
| PPP3CA | NM_000944 | 3 | protein phosphatase 3, catalytic subunit, alpha isozyme | hsa-miR-99a | −0.26 | <0.1 | 2009 |
| ZNF197 | NM_001024855 | 4 | zinc finger protein 197 | hsa-miR-100 | −0.65 | <0.1 | |
| TTC39A | NM_001080494 | 5 | tetratricopeptide repeat domain 39A | hsa-miR-99a | −0.55 | <0.1 | 2007, 2009 |
| NXF1 | NM_001081491 | 6 | nuclear RNA export factor 1 | hsa-miR-100 | −0.2 | 0.11 | 2009 |
| SMARCA4 | NM_001128844 | 7 | SWI/SNF related, matrix associated, actin dependent regulator of chromatin, subfamily a, member 4 | hsa-miR-100 | −0.26 | 0.11 | |
| LRRC8B | NM_001134476 | 8 | leucine rich repeat containing 8 family, member B | hsa-miR-99a | −0.29 | <0.1 | |
| EIF2C2 | NM_001164623 | 9 | eukaryotic translation initiation factor 2C, 2 | hsa-miR-100 | −0.4 | <0.1 | 2005, 2007, 2009 |
| TMEM135 | NM_001168724 | 10 | transmembrane protein 135 | hsa-miR-100 | −0.28 | 0.11 | |
| CLDN11 | NM_001185056 | 11 | claudin 11 | hsa-miR-100 | −0.29 | <0.1 | 2009 |
| BMPR2 | NM_001204 | 12 | bone morphogenetic protein receptor, type II (serine/threonine kinase) | hsa-miR-100 | −0.28 | 0.11 | 2005, 2007, 2009 |
| INSM1 | NM_002196 | 13 | insulinoma-associated 1 | hsa-miR-99a | −0.25 | <0.1 | 2005, 2007 |
| PPP1CB | NM_002709 | 14 | protein phosphatase 1, catalytic subunit, beta isozyme | hsa-miR-100 | −0.31 | 0.11 | 2009 |
| FZD5 | NM_003468 | 15 | frizzled family receptor 5 | hsa-miR-100 | −0.3 | <0.1 | 2007, 2009 |
| SMARCA5 | NM_003601 | 16 | SWI/SNF related, matrix associated, actin dependent regulator of chromatin, subfamily a, member 5 | hsa-miR-100 | −0.45 | <0.1 | 2005, 2007, 2009 |
| PPFIA3 | NM_003660 | 17 | protein tyrosine phosphatase, receptor type, f polypeptide (PTPRF), interacting protein (liprin), alpha 3 | hsa-miR-100 | −0.3 | 0.11 | 2005, 2007, 2009 |
| MTOR | NM_004958 | 18 | mechanistic target of rapamycin (serine/threonine kinase) | hsa-miR-100 | −0.38 | <0.1 | 2005, 2007, 2009 |
| ST5 | NM_005418 | 19 | suppression of tumorigenicity 5 | hsa-miR-100 | −0.33 | <0.1 | |
| HOXA1 | NM_005522 | 20 | homeobox A1 | hsa-miR-99a | −0.33 | <0.1 | 2005, 2007, 2009 |
| HS3ST3B1 | NM_006041 | 21 | heparan sulfate (glucosamine) 3-O-sulfotransferase 3B1 | hsa-miR-99a | −0.59 | <0.1 | 2005, 2007, 2009 |
| HS3ST2 | NM_006043 | 22 | heparan sulfate (glucosamine) 3-O-sulfotransferase 2 | hsa-miR-100 | −0.6 | <0.1 | 2005, 2007, 2009 |
| ICMT | NM_012405 | 23 | isoprenylcysteine carboxyl methyltransferase | hsa-miR-99a | −0.15 | <0.1 | 2005, 2007, 2009 |
| BAZ2A | NM_013449 | 24 | bromodomain adjacent to zinc finger domain, 2A | hsa-miR-100 | −0.46 | <0.1 | 2005, 2007, 2009 |
| ZZEF1 | NM_015113 | 25 | zinc finger, ZZ-type with EF-hand domain 1 | hsa-miR-100 | −0.42 | <0.1 | 2005, 2007, 2009 |
| NIPBL | NM_015384 | 26 | Nipped-B homolog (*Drosophila*) | hsa-miR-99a | −0.3 | 0.11 | |
| PI15 | NM_015886 | 27 | peptidase inhibitor 15 | hsa-miR-99a | −0.19 | 0.11 | 2009 |

TABLE S1-continued miR-99/100 predicted targets

| Target gene | Representative transcript | SEQ ID NO: | Gene name | Representative miRNA | Total context + score | Aggregate PCT | Publication (s) |
|---|---|---|---|---|---|---|---|
| ZBTB7A | NM_015898 | 28 | zinc finger and BTB domain containing 7A | hsa-miR-100 | −0.16 | 0.11 | 2007, 2009 |
| PPPDE1 | NM_016076 | 29 | PPPDE peptidase domain containing 1 | hsa-miR-99a | −0.26 | 0.11 | 2009 |
| EPDR1 | NM_017549 | 30 | ependymin related protein 1 (zebrafish) | hsa-miR-100 | −0.69 | <0.1 | 2009 |
| RAVER2 | NM_018211 | 31 | ribonucleoprotein, PTB-binding 2 | hsa-miR-99a | −0.44 | <0.1 | 2007, 2009 |
| CYP26B1 | NM_019885 | 32 | cytochrome P450, family 26, subfamily B, polypeptide 1 | hsa-miR-100 | −0.14 | <0.1 | 2005, 2007, 2009 |
| TAOK1 | NM_020791 | 33 | TAO kinase 1 | hsa-miR-100 | −0.21 | <0.1 | |
| MBNL1 | NM_021038 | 34 | muscleblind-like (Drosophila) | hsa-miR-99a | −0.2 | <0.1 | 2005, 2007, 2009 |
| MTMR3 | NM_021090 | 35 | myotubularin related protein 3 | hsa-miR-99a | −0.18 | <0.1 | 2005, 2007, 2009 |
| ADCY1 | NM_021116 | 36 | adenylate cyclase 1 (brain) | hsa-miR-99a | −0.4 | <0.1 | 2005, 2007, 2009 |
| RRAGD | NM_021244 | 37 | Ras-related GTP binding D | hsa-miR-100 | −0.35 | <0.1 | |
| TRIB2 | NM_021643 | 38 | tribbles homolog 2 (Drosophila) | hsa-miR-100 | −0.31 | <0.1 | 2005, 2007, 2009 |
| CEP85 | NM_022778 | 39 | centrosomal protein 85 kDa | hsa-miR-99a | −0.29 | 0.11 | 2007, 2009 |
| RMND5A | NM_022780 | 40 | required for meiotic nuclear division 5 homolog A (S. cerevisiae) | hsa-miR-99a | −0.15 | 0.11 | |
| THAP2 | NM_031435 | 41 | THAP domain containing, apoptosis associated protein 2 | hsa-miR-100 | −0.64 | 0.11 | 2007, 2009 |
| FZD8 | NM_031866 | 42 | frizzled family receptor 8 | hsa-miR-100 | −0.34 | <0.1 | 2005, 2007, 2009 |
| KBTBD8 | NM_032505 | 43 | kelch repeat and BTB (POZ) domain containing 8 | hsa-miR-100 | −0.6 | <0.1 | 2007, 2009 |
| SLC44A1 | NM_080546 | 44 | solute carrier family 44, member 1 | hsa-miR-100 | −0.31 | <0.1 | 2007, 2009 |
| ZNRF2 | NM_147128 | 45 | zinc and ring finger 2 | hsa-miR-100 | −0.24 | 0.11 | |
| ST6GALNAC4 | NM_175039 | 46 | ST6 (alpha-N-acetyl-neuraminyl-2,3-beta-galactosyl-1,3)-N-acetylgalactosaminide alpha-2,6-sialyltransferase 4 | hsa-miR-99a | −0.56 | <0.1 | |
| GRHL1 | NM_198182 | 47 | grainyhead-like 1 (Drosophila) | hsa-miR-99a | −0.3 | 0.11 | 2009 |

TABLE S2

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| ADRB2 | NM_000024 | 48 | adrenergic, beta-2-, receptor, surface | hsa-miR-4458 | −0.47 | 0.63 | 2005, 2007, 2009 |
| ADRB3 | NM_000025 | 49 | adrenergic, beta-3-, receptor | hsa-miR-4458 | −0.28 | 0.98 | 2005, 2007, 2009 |
| FAS | NM_000043 | 50 | Fas (TNF receptor superfamily, member 6) | hsa-miR-98 | −0.32 | 0.85 | 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| ATP7B | NM_000053 | 51 | ATPase, Cu++ transporting, beta polypeptide | hsa-miR-4458 | −0.09 | 0.93 | 2009 |
| CAPN3 | NM_000070 | 52 | calpain 3, (p94) | hsa-miR-4458 | −0.15 | 0.92 | 2009 |
| CLCN5 | NM_000084 | 53 | chloride channel 5 | hsa-let-7c | −0.4 | >0.99 | 2007, 2009 |
| COL1A1 | NM_000088 | 54 | collagen, type I, alpha 1 | hsa-miR-4500 | −0.18 | 0.89 | 2005, 2007, 2009 |
| COL1A2 | NM_000089 | 55 | collagen, type I, alpha 2 | hsa-miR-4500 | −0.41 | 0.95 | 2005, 2007, 2009 |
| COL3A1 | NM_000090 | 56 | collagen, type III, alpha 1 | hsa-miR-4458 | −0.37 | 0.92 | 2005, 2007, 2009 |
| CYP19A1 | NM_000103 | 57 | cytochrome P450, family 19, subfamily A, polypeptide 1 | hsa-let-7f | −0.22 | 0.9 | 2005, 2007, 2009 |
| DMD | NM_000109 | 58 | dystrophin | hsa-let-7d | −0.29 | 0.84 | 2005, 2007, 2009 |
| ERCC6 | NM_000124 | 59 | excision repair cross-complementing rodent repair deficiency, complementation group 6 | hsa-let-7d | −0.46 | 0.95 | 2005, 2007, 2009 |
| GALC | NM_000153 | 60 | galactosylceramidase | hsa-miR-4458 | −0.27 | 0.93 | 2009 |
| GHR | NM_000163 | 61 | growth hormone receptor | hsa-miR-98 | −0.16 | 0.87 | 2005, 2007, 2009 |
| HK2 | NM_000189 | 62 | hexokinase 2 | hsa-miR-4500 | −0.06 | 0.89 | 2005, 2007, 2009 |
| TBX5 | NM_000192 | 63 | T-box 5 | hsa-miR-4500 | −0.16 | 0.94 | 2005, 2007, 2009 |
| INSR | NM_000208 | 64 | insulin receptor | hsa-let-7i | −0.11 | 0.99 | 2007, 2009 |
| ITGB3 | NM_000212 | 65 | integrin, beta 3 (platelet glycoprotein IIIa, antigen CD61) | hsa-miR-4458 | −0.21 | >0.99 | 2005, 2007, 2009 |
| RB1 | NM_000321 | 66 | retinoblastoma 1 | hsa-miR-4500 | −0.1 | 0.83 | 2005, 2007, 2009 |
| SCN5A | NM_000335 | 67 | sodium channel, voltage-gated, type V, alpha subunit | hsa-miR-4458 | −0.04 | 0.95 | 2005, 2007, 2009 |
| SGCD | NM_000337 | 68 | sarcoglycan, delta (35 kDa dystrophin-associated glycoprotein) | hsa-miR-4458 | >−0.02 | 0.7 | 2005, 2007, 2009 |
| TSC1 | NM_000368 | 69 | tuberous sclerosis 1 | hsa-miR-4458 | −0.22 | 0.95 | 2005, 2007, 2009 |
| CDKN1A | NM_000389 | 70 | cyclin-dependent kinase inhibitor 1A (p21, Cip1) | hsa-let-7i | −0.24 | 0.76 | 2009 |
| TPP1 | NM_000391 | 71 | tripeptidyl peptidase I | hsa-miR-4458 | −0.24 | 0.97 | 2009 |
| COL5A2 | NM_000393 | 72 | collagen, type V, alpha 2 | hsa-miR-4458 | −0.16 | 0.95 | 2005, 2007, 2009 |
| GALE | NM_000403 | 73 | UDP-galactose-4-epimerase | hsa-miR-4458 | −0.28 | 0.91 | 2005, 2007, 2009 |
| LOR | NM_000427 | 74 | loricrin | hsa-let-7g | −0.27 | 0.88 | 2009 |
| RAG1 | NM_000448 | 75 | recombination activating gene 1 | hsa-let-7a | −0.17 | 0.76 | 2009 |
| AMT | NM_000481 | 76 | aminomethyltransferase | hsa-let-7a | −0.29 | 0.82 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| COL4A5 | NM_000495 | 77 | collagen, type IV, alpha 5 | hsa-miR-4500 | −0.14 | 0.91 | 2005, 2007, 2009 |
| KCNJ11 | NM_000525 | 78 | potassium inwardly-rectifying channel, subfamily J, member 11 | hsa-let-7d | −0.44 | 0.78 | 2009 |
| TP53 | NM_000546 | 79 | tumor protein p53 | hsa-let-7d | −0.28 | 0.93 | 2009 |
| DCX | NM_000555 | 80 | doublecortin | hsa-let-7d | −0.05 | 0.87 | 2005, 2007 |
| IL6R | NM_000565 | 81 | interleukin 6 receptor | hsa-miR-4500 | −0.16 | 0.94 | |
| IL10 | NM_000572 | 82 | interleukin 10 | hsa-let-7e | −0.14 | 0.94 | 2005, 2007, 2009 |
| IL6 | NM_000600 | 83 | interleukin 6 (interferon, beta 2) | hsa-miR-4500 | −0.15 | 0.73 | 2007 |
| IGF1 | NM_000618 | 84 | insulin-like growth factor 1 (somatomedin C) | hsa-let-7f | −0.1 | 0.97 | 2009 |
| NOS1 | NM_000620 | 85 | nitric oxide synthase 1 (neuronal) | hsa-miR-4458 | −0.11 | 0.95 | |
| FASLG | NM_000639 | 86 | Fas ligand (TNF superfamily, member 6) | hsa-miR-4458 | −0.26 | 0.98 | 2005, 2007, 2009 |
| ADRB1 | NM_000684 | 87 | adrenergic, beta-1-, receptor | hsa-miR-4500 | −0.25 | 0.98 | 2007, 2009 |
| CACNA1D | NM_000720 | 88 | calcium channel, voltage-dependent, L type, alpha 1D subunit | hsa-let-7b | −0.07 | 0.88 | 2005, 2007, 2009 |
| CACNA1E | NM_000721 | 89 | calcium channel, voltage-dependent, R type, alpha 1E subunit | hsa-miR-4500 | −0.01 | 0.93 | 2005, 2007, 2009 |
| GABRA6 | NM_000811 | 90 | gamma-aminobutyric acid (GABA) A receptor, alpha 6 | hsa-let-7d | −0.16 | 0.84 | 2009 |
| HTR1E | NM_000865 | 91 | 5-hydroxytryptamine (serotonin) receptor 1E | hsa-let-7d | −0.27 | 0.89 | 2009 |
| HTR4 | NM_000870 | 92 | 5-hydroxytryptamine (serotonin) receptor 4 | hsa-let-7a | −0.12 | 0.94 | 2005, 2007, 2009 |
| IGF1R | NM_000875 | 93 | insulin-like growth factor 1 receptor | hsa-let-7b | −0.42 | >0.99 | 2007, 2009 |
| OPRM1 | NM_000914 | 94 | opioid receptor, mu 1 | hsa-miR-4500 | −0.2 | 0.92 | 2005, 2007, 2009 |
| PTAFR | NM_000952 | 95 | platelet-activating factor receptor | hsa-miR-4500 | −0.69 | 0.94 | |
| NKIRAS2 | NM_001001349 | 96 | NFKB inhibitor interacting Ras-like 2 | hsa-miR-4458 | −0.09 | 0.88 | 2005, 2007, 2009 |
| ATP2B4 | NM_001001396 | 97 | ATPase, Ca++ transporting, plasma membrane 4 | hsa-let-7f | −0.05 | 0.93 | 2005, 2007, 2009 |
| RORC | NM_001001523 | 98 | RAR-related orphan receptor C | hsa-miR-4458 | −0.12 | 0.93 | 2005, 2007, 2009 |
| GDF6 | NM_001001557 | 99 | growth differentiation factor 6 | hsa-miR-4500 | −0.5 | 0.98 | 2005, 2007, 2009 |
| MTUS1 | NM_001001924 | 100 | microtubule associated tumor suppressor 1 | hsa-let-7d | −0.14 | 0.71 | 2009 |
| PPARA | NM_001001928 | 101 | peroxisome proliferator-activated receptor alpha | hsa-miR-4458 | −0.04 | 0.97 | 2007, 2009 |
| GOLGA7 | NM_001002296 | 102 | golgin A7 | hsa-miR-4500 | −0.15 | 0.7 | 2005, 2007, 2009 |
| WNK3 | NM_001002838 | 103 | WNK lysine deficient protein kinase 3 | hsa-miR-4458 | −0.09 | 0.91 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| CACNA1I | NM_001003406 | 104 | calcium channel, voltage-dependent, T type, alpha 1I subunit | hsa-miR-4458 | −0.1 | 0.92 | 2009 |
| SMAD2 | NM_001003652 | 105 | SMAD family member 2 | hsa-miR-4458 | −0.09 | 0.9 | 2007, 2009 |
| C18orf1 | NM_001003674 | 106 | chromosome 18 open reading frame 1 | hsa-miR-4500 | −0.01 | 0.76 | |
| KLHL31 | NM_001003760 | 107 | kelch-like 31 (*Drosophila*) | hsa-let-7d | −0.34 | 0.93 | 2009 |
| MGLL | NM_001003794 | 108 | monoglyceride lipase | hsa-miR-4458 | >−0.03 | 0.99 | 2005, 2007, 2009 |
| DLGAP1 | NM_001003809 | 109 | discs, large (*Drosophila*) homolog-associated protein 1 | hsa-miR-4500 | −0.03 | 0.81 | |
| CD200 | NM_001004196 | 110 | CD200 molecule | hsa-miR-98 | −0.12 | 0.75 | |
| ZNF740 | NM_001004304 | 111 | zinc finger protein 740 | hsa-let-7d | >−0.02 | 0.94 | 2007, 2009 |
| LIN28B | NM_001004317 | 112 | lin-28 homolog B (*C. elegans*) | hsa-let-7d | −0.98 | >0.99 | 2007, 2009 |
| PLEKHG7 | NM_001004330 | 113 | pleckstrin homology domain containing, family G (with RhoGef domain) member 7 | hsa-miR-4458 | −0.34 | 0.94 | 2009 |
| TRIM67 | NM_001004342 | 114 | tripartite motif containing 67 | hsa-let-7f | −0.08 | >0.99 | 2007, 2009 |
| NRARP | NM_001004354 | 115 | NOTCH-regulated ankyrin repeat protein | hsa-miR-4458 | −0.2 | 0.67 | 2005, 2007, 2009 |
| ITGA11 | NM_001004439 | 116 | integrin, alpha 11 | hsa-miR-4458 | −0.07 | 0.77 | |
| YPEL2 | NM_001005404 | 117 | yippee-like 2 (*Drosophila*) | hsa-miR-4500 | −0.15 | 0.96 | 2009 |
| PLCXD3 | NM_001005473 | 118 | phosphatidylinositol-specific phospholipase C, X domain containing 3 | hsa-miR-4458 | −0.19 | 0.8 | 2005, 2007 |
| CPM | NM_001005502 | 119 | carboxypeptidase M | hsa-miR-4458 | −0.27 | 0.95 | 2005, 2007, 2009 |
| EDA | NM_001005609 | 120 | ectodysplasin A | hsa-miR-4458 | −0.06 | 0.92 | 2005, 2007, 2009 |
| ZNF473 | NM_001006656 | 121 | zinc finger protein 473 | hsa-let-7d | −0.31 | 0.98 | 2009 |
| NTRK3 | NM_001007156 | 122 | neurotrophic tyrosine kinase, receptor, type 3 | hsa-let-7f | −0.16 | 0.82 | 2009 |
| IGF2BP2 | NM_001007225 | 123 | insulin-like growth factor 2 mRNA binding protein 2 | hsa-let-7b | −0.4 | >0.99 | 2007, 2009 |
| BRWD1 | NM_001007246 | 124 | bromodomain and WD repeat domain containing 1 | hsa-let-7d | −0.5 | 0.73 | |
| PRDM2 | NM_001007257 | 125 | PR domain containing 2, with ZNF domain | hsa-let-7g | −0.35 | 0.87 | |
| GEMIN7 | NM_001007269 | 126 | gem (nuclear organelle) associated protein 7 | hsa-miR-4500 | −0.37 | <0.1 | 2009 |
| IRGQ | NM_001007561 | 127 | immunity-related GTPase family, Q | hsa-let-7g | −0.11 | 0.85 | |
| BCAP29 | NM_001008405 | 128 | B-cell receptor-associated protein 29 | hsa-miR-4500 | −0.16 | 0.94 | 2007, 2009 |
| STEAP3 | NM_001008410 | 129 | STEAP family member 3 | hsa-miR-4458 | −0.28 | 0.98 | 2009 |
| KIAA2022 | NM_001008537 | 130 | KIAA2022 | hsa-let-7g | −0.12 | 0.92 | 2009 |
| USP20 | NM_001008563 | 131 | ubiquitin specific peptidase 20 | hsa-miR-4500 | −0.06 | 0.84 | |
| FNIP1 | NM_001008738 | 132 | folliculin interacting protein 1 | hsa-miR-98 | −0.22 | 0.98 | 2007, 2009 |
| ACSL6 | NM_001009185 | 133 | acyl-CoA synthetase long-chain family member 6 | hsa-let-7d | −0.39 | 0.98 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| MFAP3L | NM_001009554 | 134 | microfibrillar-associated protein 3-like | hsa-miR-4500 | −0.09 | 0.93 | 2009 |
| MEIS3 | NM_001009813 | 135 | Meis homeobox 3 | hsa-miR-4458 | −0.26 | 0.92 | 2005, 2007, 2009 |
| KIAA0930 | NM_001009880 | 136 | KIAA0930 | hsa-let-7d | −0.06 | >0.99 | 2007, 2009 |
| C20orf194 | NM_001009984 | 137 | chromosome 20 open reading frame 194 | hsa-miR-4500 | −0.18 | >0.99 | 2009 |
| ARHGAP28 | NM_001010000 | 138 | Rho GTPase activating protein 28 | hsa-let-7a | −0.35 | 0.95 | 2005, 2007, 2009 |
| PM20D2 | NM_001010853 | 139 | peptidase M20 domain containing 2 | hsa-let-7a | −0.19 | 0.78 | |
| ACER2 | NM_001010887 | 140 | alkaline ceramidase 2 | hsa-miR-4458 | −0.15 | 0.94 | 2007, 2009 |
| SLC5A9 | NM_001011547 | 141 | solute carrier family 5 (sodium/glucose cotransporter), member 9 | hsa-miR-4458 | −0.5 | 0.79 | 2009 |
| NAA30 | NM_001011713 | 142 | N(alpha)-acetyltransferase 30, NatC catalytic subunit | hsa-miR-4500 | −0.16 | 0.94 | 2007, 2009 |
| NHLRC3 | NM_001012754 | 143 | NHL repeat containing 3 | hsa-let-7a | −0.27 | 0.95 | 2007, 2009 |
| SNX30 | NM_001012994 | 144 | sorting nexin family member 30 | hsa-let-7d | −0.15 | 0.95 | 2009 |
| FIGNL2 | NM_001013690 | 145 | fidgetin-like 2 | hsa-miR-4458 | −1.07 | >0.99 | 2009 |
| C8orf58 | NM_001013842 | 146 | chromosome 8 open reading frame 58 | hsa-let-7d | −0.42 | 0.97 | 2009 |
| DCUN1D2 | NM_001014283 | 147 | DCN1, defective in cullin neddylation 1, domain containing 2 (S. cerevisiae) | hsa-let-7b | −0.13 | 0.94 | 2007, 2009 |
| KATNAL1 | NM_001014380 | 148 | katanin p60 subunit A-like 1 | hsa-miR-4458 | −0.28 | 0.94 | 2009 |
| USP21 | NM_001014443 | 149 | ubiquitin specific peptidase 21 | hsa-miR-4458 | −0.12 | 0.92 | 2005, 2007, 2009 |
| DDX19B | NM_001014449 | 150 | DEAD (Asp-Glu-Ala-As) box polypeptide 19B | hsa-miR-4500 | −0.47 | 0.97 | 2007, 2009 |
| RTKN | NM_001015055 | 151 | rhotekin | hsa-miR-98 | −0.14 | 0.76 | |
| GOPC | NM_001017408 | 152 | golgi-associated PDZ and coiled-coil motif containing | hsa-miR-4500 | −0.1 | 0.87 | 2009 |
| CALN1 | NM_001017440 | 153 | calneuron 1 | hsa-miR-4458 | −0.15 | 0.92 | 2009 |
| C14orf28 | NM_001017923 | 154 | chromosome 14 open reading frame 28 | hsa-let-7g | −1.25 | >0.99 | 2007, 2009 |
| OPA3 | NM_001017989 | 155 | optic atrophy 3 (autosomal recessive, with chorea and spastic paraplegia) | hsa-miR-4458 | −0.42 | 0.71 | |
| DKK3 | NM_001018057 | 156 | dickkopf homolog 3 (Xenopus laevis) | hsa-let-7d | −0.1 | 0.93 | 2007, 2009 |
| SERF2 | NM_001018108 | 157 | small EDRK-rich factor 2 | hsa-let-7d | −0.55 | 0.85 | |
| IQCB1 | NM_001023570 | 158 | IQ motif containing B1 | hsa-miR-4500 | −0.3 | 0.88 | 2009 |
| SBK1 | NM_001024401 | 159 | SH3-binding domain kinase 1 | hsa-let-7b | −0.1 | 0.94 | 2007, 2009 |
| CD276 | NM_001024736 | 160 | CD276 molecule | hsa-miR-4458 | −0.06 | 0.71 | |
| BCL7A | NM_001024808 | 161 | B-cell CLL/lymphoma 7A | hsa-miR-4500 | −0.06 | 0.9 | 2005, 2007, 2009 |
| KCTD21 | NM_001029859 | 162 | potassium channel tetramerisation domain containing 21 | hsa-miR-98 | −0.54 | 0.98 | 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| SLC10A7 | NM_001029998 | 163 | solute carrier family 10 (sodium/bile acid cotransporter family), member 7 | hsa-miR-98 | −0.25 | 0.94 | |
| CTNS | NM_001031681 | 164 | cystinosin, lysosomal cystine transporter | hsa-let-7d | −0.12 | 0.93 | 2005, 2007, 2009 |
| RBFOX2 | NM_001031695 | 165 | RNA binding protein, fox-1 homolog (C. elegans) 2 | hsa-miR-98 | −0.19 | 0.94 | 2005, 2007, 2009 |
| PLD3 | NM_001031696 | 166 | phospholipase D family, member 3 | hsa-miR-4458 | −0.13 | 0.9 | 2005, 2007, 2009 |
| ERGIC1 | NM_001031711 | 167 | endoplasmic reticulum-golgi intermediate compartment (ERGIC) 1 | hsa-let-7d | −0.21 | 0.93 | |
| TMPO | NM_001032283 | 168 | thymopoietin | hsa-miR-4500 | −0.1 | 0.83 | |
| STK24 | NM_001032296 | 169 | serine/threonine kinase 24 | hsa-miR-4458 | −0.11 | 0.93 | 2009 |
| MYCL1 | NM_001033081 | 170 | v-myc myelocytomatosis viral oncogene homolog 1, lung carcinoma derived (avian) | hsa-let-7a | −0.09 | 0.88 | 2007, 2009 |
| SRGAP3 | NM_001033117 | 171 | SLIT-ROBO Rho GTPase activating protein 3 | hsa-miR-4500 | −0.13 | 0.94 | 2005, 2007, 2009 |
| WIPI2 | NM_001033518 | 172 | WD repeat domain, phosphoinositide interacting 2 | hsa-let-7e | −0.34 | 0.92 | 2009 |
| RRM2 | NM_001034 | 173 | ribonucleotide reductase M2 | hsa-miR-4500 | −0.36 | 0.95 | 2007, 2009 |
| ARL5A | NM_001037174 | 174 | ADP-ribosylation factor-like 5A | hsa-let-7g | −0.13 | 0.94 | 2007, 2009 |
| CDC42SE1 | NM_001038707 | 175 | CDC42 small effector 1 | hsa-miR-4500 | −0.22 | 0.71 | 2009 |
| TRIM71 | NM_001039111 | 176 | tripartite motif containing 71 | hsa-miR-4458 | −0.89 | >0.99 | 2007, 2009 |
| TRIOBP | NM_001039141 | 177 | TRIO and F-actin binding protein | hsa-miR-4458 | −0.12 | 0.86 | 2009 |
| GK5 | NM_001039547 | 178 | glycerol kinase 5 (putative) | hsa-let-7d | −0.16 | 0.85 | |
| KREMEN1 | NM_001039570 | 179 | kringle containing transmembrane protein 1 | hsa-miR-4458 | −0.17 | 0.97 | 2007, 2009 |
| SEC14L1 | NM_001039573 | 180 | SEC14-like 1 (S. cerevisiae) | hsa-miR-4500 | −0.18 | 0.92 | 2005, 2007, 2009 |
| KCNC4 | NM_001039574 | 181 | potassium voltage-gated channel, Shaw-related subfamily, member 4 | hsa-miR-4500 | −0.1 | 0.84 | 2009 |
| TMPPE | NM_001039770 | 182 | transmembrane protein with metallophosphoesterase domain | hsa-miR-4458 | −0.17 | 0.84 | 2009 |
| CHIC1 | NM_001039840 | 183 | cysteine-rich hydrophobic domain 1 | hsa-miR-4458 | >−0.04 | >0.99 | 2009 |
| MLLT4 | NM_001040000 | 184 | myeloid/lymphoid or mixed-lineage leukemia (trithorax homolog, Drosophila); translocated to, 4 | hsa-miR-4458 | −0.16 | 0.74 | 2007, 2009 |
| PQLC2 | NM_001040125 | 185 | PQ loop repeat containing 2 | hsa-miR-4458 | −0.3 | 0.95 | 2009 |
| PEG10 | NM_001040152 | 186 | paternally expressed 10 | hsa-miR-4458 | −0.02 | 0.71 | 2009 |
| MTMR12 | NM_001040446 | 187 | myotubularin related protein 12 | hsa-miR-4458 | −0.06 | 0.9 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| PTPRD | NM_001040712 | 188 | protein tyrosine phosphatase, receptor type, D | hsa-miR-4500 | −0.22 | 0.96 | 2007, 2009 |
| KIAA0895L | NM_001040715 | 189 | KIAA0895-like | hsa-let-7i | −0.14 | 0.93 | 2007, 2009 |
| USP44 | NM_001042403 | 190 | ubiquitin specific peptidase 44 | hsa-miR-4458 | −0.14 | 0.93 | 2009 |
| RUFY2 | NM_001042417 | 191 | RUN and FYVE domain containing 2 | hsa-miR-98 | −0.27 | 0.82 | |
| C6orf204 | NM_001042475 | 192 | chromosome 6 open reading frame 204 | hsa-miR-4458 | −0.13 | 0.94 | |
| DLGAP4 | NM_001042486 | 193 | discs, large (*Drosophila*) homolog-associated protein 4 | hsa-let-7d | −0.31 | 0.97 | 2009 |
| C2orf88 | NM_001042519 | 194 | chromosome 2 open reading frame 88 | hsa-miR-4500 | −0.17 | 0.89 | 2009 |
| ATPAF1 | NM_001042546 | 195 | ATP synthase mitochondrial F1 complex assembly factor 1 | hsa-let-7d | −0.43 | 0.92 | 2009 |
| FRS2 | NM_001042555 | 196 | fibroblast growth factor receptor substrate 2 | hsa-let-7i | −0.04 | 0.86 | 2007, 2009 |
| EIF4G2 | NM_001042559 | 197 | eukaryotic translation initiation factor 4 gamma, 2 | hsa-let-7d | −0.27 | 0.92 | 2005, 2007, 2009 |
| DPH3 | NM_001047434 | 198 | DPH3, KTI11 homolog (*S. cerevisiae*) | hsa-let-7i | −0.4 | 0.98 | |
| UHRF1 | NM_001048201 | 199 | ubiquitin-like with PHD and ring finger domains 1 | hsa-let-7d | −0.17 | 0.94 | 2009 |
| TNFRSF1B | NM_001066 | 200 | tumor necrosis factor receptor superfamily, member 1B | hsa-miR-4458 | −0.09 | 0.99 | 2005, 2007, 2009 |
| CDC14B | NM_001077181 | 201 | CDC14 cell division cycle 14 homolog B (*S. cerevisiae*) | hsa-miR-4500 | −0.08 | 0.88 | 2009 |
| ATG9A | NM_001077198 | 202 | ATG9 autophagy related 9 homolog A (*S. cerevisiae*) | hsa-let-7d | −0.03 | 0.74 | |
| SREK1 | NM_001077199 | 203 | splicing regulatory glutamine/lysine-rich protein 1 | hsa-miR-4458 | −0.09 | 0.92 | 2005, 2007, 2009 |
| IKZF2 | NM_001079526 | 204 | IKAROS family zinc finger 2 (Helios) | hsa-let-7g | −0.13 | 0.98 | 2007, 2009 |
| CPEB1 | NM_001079533 | 205 | cytoplasmic polyadenylation element binding protein 1 | hsa-miR-4500 | −0.44 | 0.91 | 2007, 2009 |
| FNDC3A | NM_001079673 | 206 | fibronectin type III domain containing 3A | hsa-let-7d | −0.39 | 0.97 | 2005, 2007, 2009 |
| GYG2 | NM_001079855 | 207 | glycogenin 2 | hsa-let-7a | −0.22 | 0.88 | 2009 |
| VAV3 | NM_001079874 | 208 | vav 3 guanine nucleotide exchange factor | hsa-miR-4500 | −0.11 | 0.92 | 2005, 2007, 2009 |
| DMP1 | NM_001079911 | 209 | dentin matrix acidic phosphoprotein 1 | hsa-miR-4500 | −0.21 | 0.94 | 2005, 2007, 2009 |
| LDB3 | NM_001080114 | 210 | LIM domain binding 3 | hsa-miR-4458 | −0.09 | 0.84 | 2009 |
| GJC1 | NM_001080383 | 211 | gap junction protein, gamma 1, 45 kDa | hsa-miR-4500 | −0.42 | 0.95 | 2009 |
| KIAA1147 | NM_001080392 | 212 | KIAA1147 | hsa-miR-4458 | −0.15 | 0.86 | 2007, 2009 |
| SLC45A4 | NM_001080431 | 213 | solute carrier family 45, member 4 | hsa-let-7d | −0.08 | 0.91 | 2003, 2007, 2009 |
| DNA2 | NM_001080449 | 214 | DNA replication helicase 2 homolog (yeast) | hsa-miR-4458 | −0.53 | 0.6 | 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| MYO5B | NM_001080467 | 215 | myosin VB | hsa-let-7g | −0.04 | 0.78 | 2009 |
| ZNF697 | NM_001080470 | 216 | zinc finger protein 697 | hsa-miR-4458 | −0.14 | 0.93 | 2007, 2009 |
| ZNF275 | NM_001080485 | 217 | zinc finger protein 275 | hsa-miR-4458 | −0.11 | 0.99 | 2007, 2009 |
| MGA | NM_001080541 | 218 | MAX gene associated | hsa-miR-4500 | −0.12 | 0.91 | 2007, 2009 |
| THOC2 | NM_001081550 | 219 | THO complex 2 | hsa-miR-4458 | −0.17 | 0.85 | 2007, 2009 |
| CPSF4 | NM_001081559 | 220 | cleavage and polyadenylation specific factor 4, 30 kDa | hsa-miR-4458 | −0.12 | 0.77 | 2005, 2007, 2009 |
| C11orf57 | NM_001082969 | 221 | chromosome 11 open reading frame 57 | hsa-let-7f | −0.25 | 0.89 | 2007, 2009 |
| E2F5 | NM_001083588 | 222 | E2F transcription factor 5, p130-binding | hsa-miR-4500 | −0.3 | 0.86 | 2009 |
| ANKRD12 | NM_001083625 | 223 | ankyrin repeat domain 12 | hsa-miR-4458 | >−0.02 | 0.77 | |
| FOXN3 | NM_001085471 | 224 | forkhead box N3 | hsa-miR-4458 | >−0.01 | 0.82 | |
| MEX3A | NM_001093725 | 225 | mex-3 homolog A (*C. elegans*) | hsa-miR-98 | −0.15 | 0.92 | 2009 |
| HIC1 | NM_001098202 | 226 | hypermethylated in cancer 1 | hsa-miR-4458 | −0.05 | 0.84 | 2009 |
| MGAT3 | NM_001098270 | 227 | mannosyl (beta-1,4-)-glycoprotein beta-1,4-N-acetylglucosaminyltransferase | hsa-miR-4458 | >−0.02 | 0.66 | |
| SLC4A4 | NM_001098484 | 228 | solute carrier family 4, sodium bicarbonate cotransporter, member 4 | hsa-miR-4458 | −0.16 | 0.95 | 2005, 2007, 2009 |
| FAM104A | NM_001098832 | 229 | family with sequence similarity 104, member A | hsa-miR-4458 | −0.21 | 0.92 | 2007, 2009 |
| ATXN7L3 | NM_001098833 | 230 | ataxin 7-like 3 | hsa-miR-4500 | −0.06 | 0.74 | |
| BTBD9 | NM_001099272 | 231 | BTB (POZ) domain containing 9 | hsa-let-7a | −0.16 | 0.95 | 2009 |
| NIPAL4 | NM_001099287 | 232 | NIPA-like domain containing 4 | hsa-miR-4458 | −0.17 | 0.93 | 2009 |
| SH3RF3 | NM_001099289 | 233 | SH3 domain containing ring finger 3 | hsa-miR-4458 | −0.08 | 0.92 | 2009 |
| GXYLT1 | NM_001099650 | 234 | glucoside xylosyltransferase 1 | hsa-miR-4500 | −0.37 | 0.99 | 2009 |
| PTAR1 | NM_001099666 | 235 | protein prenyltransferase alpha subunit repeat containing 1 | hsa-miR-4500 | −0.15 | 0.98 | 2009 |
| FBXL19 | NM_001099784 | 236 | F-box and leucine-rich repeat protein 19 | hsa-miR-4458 | −0.1 | 0.7 | 2009 |
| ACTA1 | NM_001100 | 237 | actin, alpha 1, skeletal muscle | hsa-let-7c | −0.21 | 0.72 | 2005, 2007 |
| PHACTR2 | NM_001100164 | 238 | phosphatase and actin regulator 2 | hsa-miR-4500 | −0.15 | 0.94 | 2009 |
| MOBKL3 | NM_001100819 | 239 | MOB1, Mps One Binder kinase activator-like 3 (yeast) | hsa-let-7a | −0.12 | 0.93 | 2005, 2007, 2009 |
| PACS2 | NM_001100913 | 240 | phosphofurin acidic cluster sorting protein 2 | hsa-miR-4458 | −0.14 | 0.79 | 2009 |
| IGLON5 | NM_001101372 | 241 | IgLON family member 5 | hsa-let-7d | −0.04 | 0.94 | 2009 |
| SAMD12 | NM_001101676 | 242 | sterile alpha motif domain containing 12 | hsa-miR-4500 | −0.05 | 0.94 | 2009 |
| DTX2 | NM_001102594 | 243 | deltex homolog 2 (*Drosophila*) | hsa-let-7d | −0.46 | >0.99 | 2005, 2007, 2009 |
| FAM118A | NM_001104595 | 244 | family with sequence similarity 118, member A | hsa-miR-4500 | −0.28 | 0.98 | 2007, 2009 |
| FAM123C | NM_001105193 | 245 | family with sequence similarity 123C | hsa-miR-4500 | −0.25 | 0.87 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| PCDH19 | NM_001105243 | 246 | protocadherin 19 | hsa-miR-4500 | −0.12 | 0.95 | 2007, 2009 |
| ZFYVE16 | NM_001105251 | 247 | zinc finger, FYVE domain containing 16 | hsa-miR-4500 | −0.16 | 0.71 | 2009 |
| SWT1 | NM_001105518 | 248 | SWT1 RNA endoribonuclease homolog (*S. cerevisiae*) | hsa-let-7b | −0.21 | 0.85 | 2007, 2009 |
| CAP1 | NM_001105530 | 249 | CAP, adenylate cyclase-associated protein 1 (yeast) | hsa-miR-4500 | −0.14 | 0.85 | 2005, 2007, 2009 |
| FAM135A | NM_001105531 | 250 | family with sequence similarity 135, member A | hsa-let-7f | −0.19 | 0.85 | 2005, 2007, 2009 |
| ZBTB10 | NM_001105539 | 251 | zinc finger and BTB domain containing 10 | hsa-miR-4500 | −0.06 | 0.72 | 2005, 2007 |
| NEFM | NM_001105541 | 252 | neurofilament, medium polypeptide | hsa-let-7f | −0.16 | 0.86 | 2007, 2009 |
| FBXO45 | NM_001105573 | 253 | F-box protein 45 | hsa-miR-4458 | −0.06 | 0.89 | 2009 |
| ACVR2B | NM_001106 | 254 | activin A receptor, type IIB | hsa-miR-4500 | −0.03 | >0.99 | 2007, 2009 |
| C12orf51 | NM_001109662 | 255 | chromosome 12 open reading frame 51 | hsa-miR-4458 | −0.09 | 0.92 | 2009 |
| GSG1L | NM_001109763 | 256 | GSG1-like | hsa-miR-4458 | −0.08 | 0.73 | |
| ACVR1C | NM_001111031 | 257 | activin A receptor, type IC | hsa-miR-4458 | −0.48 | 0.99 | 2005, 2007, 2009 |
| C3orf63 | NM_001112736 | 258 | chromosome 3 open reading frame 63 | hsa-miR-4458 | −0.02 | 0.91 | 2009 |
| HIPK2 | NM_001113239 | 259 | homeodomain interacting protein kinase 2 | hsa-let-7d | −0.03 | 0.94 | 2009 |
| AMOT | NM_001113490 | 260 | angiomotin | hsa-miR-4458 | −0.12 | 0.76 | |
| ARHGEF7 | NM_001113513 | 261 | Rho guanine nucleotide exchange factor (GEF) 7 | hsa-let-7a | −0.14 | 0.94 | |
| CTSC | NM_001114173 | 262 | cathepsin C | hsa-miR-4458 | −0.15 | 0.89 | 2009 |
| ADCY9 | NM_001116 | 263 | adenylate cyclase 9 | hsa-miR-4458 | −0.03 | 0.91 | 2005, 2007, 2009 |
| NAPEPLD | NM_001122838 | 264 | N-acyl phosphatidylethanolamine phospholipase D | hsa-miR-4458 | −0.05 | 0.94 | 2007, 2009 |
| CASK | NM_001126054 | 265 | calcium/calmodulin-dependent serine protein kinase (MAGUK family) | hsa-let-7d | −0.04 | 0.91 | |
| ELF4 | NM_001127197 | 266 | E74-like factor 4 (ets domain transcription factor) | hsa-let-7a | −0.17 | 0.94 | 2007, 2009 |
| TET2 | NM_001127208 | 267 | tet oncogene family member 2 | hsa-miR-4458 | −0.16 | 0.96 | |
| CBX5 | NM_001127321 | 268 | chromobox homolog 5 | hsa-miR-4458 | −0.17 | >0.99 | |
| CRY2 | NM_001127457 | 269 | cryptochrome 2 (photolyase-like) | hsa-miR-4458 | −0.12 | 0.93 | 2005, 2007, 2009 |
| STXBP5 | NM_001127715 | 270 | syntaxin binding protein 5 (tomosyn) | hsa-let-7d | −0.15 | 0.8 | 2009 |
| SULF1 | NM_001128204 | 271 | sulfatase 1 | hsa-miR-4500 | −0.1 | 0.85 | 2009 |
| SMARCAD1 | NM_001128429 | 272 | SWI/SNF-related, matrix-associated actin-dependent regulator of chromatin, subfamily a, containing DEAD/H box 1 | hsa-let-7f | −0.57 | 0.95 | 2005, 2007, 2009 |
| RASGRP1 | NM_001128602 | 273 | RAS guanyl releasing protein 1 (calcium and DAG-regulated) | hsa-miR-4458 | −0.34 | 0.97 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| PAK1 | NM_001128620 | 274 | p21 protein (Cdc42/Rac)-activated kinase 1 | hsa-miR-4500 | −0.18 | 0.78 | 2005, 2007, 2009 |
| SPIRE1 | NM_001128626 | 275 | spire homolog 1 (*Drosophila*) | hsa-let-7a | −0.04 | 0.92 | 2009 |
| CALU | NM_001130674 | 276 | calumenin | hsa-miR-4458 | −0.19 | 0.93 | 2005, 2007, 2009 |
| STYX | NM_001130701 | 277 | serine/threonine/tyrosine interacting protein | hsa-miR-4500 | −0.09 | 0.93 | |
| GAS7 | NM_001130831 | 278 | growth arrest-specific 7 | hsa-miR-4500 | −0.28 | 0.98 | 2005, 2007, 2009 |
| RTCD1 | NM_001130841 | 279 | RNA terminal phosphate cyclase domain 1 | hsa-miR-4458 | −0.2 | 0.88 | |
| TGFBR1 | NM_001130916 | 280 | transforming growth factor, beta receptor 1 | hsa-let-7f | −0.52 | >0.99 | 2005, 2007, 2009 |
| TTLL6 | NM_001130918 | 281 | tubulin tyrosine ligase-like family, member 6 | hsa-miR-4458 | −0.26 | 0.76 | |
| TMEM194A | NM_001130963 | 282 | transmembrane protein 194A | hsa-let-7a | −0.07 | 0.94 | 2009 |
| MEF2C | NM_001131005 | 283 | myocyte enhancer factor 2C | hsa-miR-4458 | −0.24 | 0.87 | |
| SAP30L | NM_001131062 | 284 | SAP30-like | hsa-miR-4458 | >−0.02 | 0.92 | |
| CCNJ | NM_001134375 | 285 | cyclin J | hsa-miR-4458 | −0.44 | 0.94 | 2005, 2007, 2009 |
| CYB561D1 | NM_001134400 | 286 | cytochrome b-561 domain containing 1 | hsa-let-7d | −0.33 | 0.91 | |
| CDV3 | NM_001134422 | 287 | CDV3 homolog (mouse) | hsa-miR-4500 | −0.13 | 0.98 | 2007, 2009 |
| LRRC8B | NM_001134476 | 288 | leucine rich repeat containing 8 family, member B | hsa-miR-4500 | −0.07 | 0.88 | |
| PBX3 | NM_001134778 | 289 | pre-B-cell leukemia homeobox 3 | hsa-miR-98 | −0.32 | 0.99 | 2005, 2007, 2009 |
| FNDC3B | NM_001135095 | 290 | fibronectin type III domain containing 3B | hsa-miR-4500 | −0.16 | 0.98 | 2005, 2007, 2009 |
| TMPRSS2 | NM_001135099 | 291 | transmembrane protease, serine 2 | hsa-let-7b | −0.32 | 0.98 | 2007, 2009 |
| HDHD1 | NM_001135565 | 292 | haloacid dehalogenase-like hydrolase domain containing 1 | hsa-miR-4500 | −0.28 | 0.62 | 2005, 2007, 2009 |
| LOC221710 | NM_001135575 | 293 | hypothetical protein LOC221710 | hsa-miR-4458 | −0.01 | 0.78 | |
| SPATA2 | NM_001135773 | 294 | spermatogenesis associated 2 | hsa-let-7a | −0.07 | 0.94 | 2005, 2007, 2009 |
| C9orf7 | NM_001135775 | 295 | chromosome 9 open reading frame 7 | hsa-miR-4500 | −0.12 | 0.92 | 2005, 2007, 2009 |
| SYT1 | NM_001135805 | 296 | synaptotagmin I | hsa-miR-4458 | −0.16 | 0.87 | 2005, 2007, 2009 |
| TMEM2 | NM_001135820 | 297 | transmembrane protein 2 | hsa-let-7g | −0.41 | 0.98 | 2005, 2007, 2009 |
| PIK3IP1 | NM_001135911 | 298 | phosphoinositide-3-kinase interacting protein 1 | hsa-let-7a | −0.19 | 0.85 | 2005, 2007, 2009 |
| TTC39C | NM_001135993 | 299 | tetratricopeptide repeat domain 39C | hsa-miR-4500 | −0.06 | 0.86 | |
| ABL2 | NM_001136000 | 300 | v-abl Abelson murine leukemia viral oncogene homolog 2 | hsa-let-7f | −0.23 | >0.99 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| MICAL3 | NM_001136004 | 301 | microtubule associated monoxygenase, calponin and LIM domain containing 3 | hsa-let-7g | −0.22 | 0.83 | |
| LMLN | NM_001136049 | 302 | leishmanolysin-like (metallopeptidase M8 family) | hsa-miR-4500 | −0.13 | 0.9 | |
| LRIG3 | NM_001136051 | 303 | leucine-rich repeats and immunoglobulin-like domains 3 | hsa-miR-4458 | −0.49 | 0.96 | 2005, 2007, 2009 |
| ZNF879 | NM_001136116 | 304 | zinc finger protein 879 | hsa-miR-4458 | −0.34 | 0.95 | |
| ATXN7L3B | NM_001136262 | 305 | ataxin 7-like 3B | hsa-miR-4458 | >−0.01 | 0.91 | |
| VASH2 | NM_001136474 | 306 | vasohibin 2 | hsa-let-7d | −0.13 | 0.93 | 2007, 2009 |
| BTF3L4 | NM_001136497 | 307 | basic transcription factor 3-like 4 | hsa-miR-4458 | −0.12 | 0.9 | 2009 |
| SYT2 | NM_001136504 | 308 | synaptotagmin II | hsa-miR-4500 | −0.16 | 0.94 | 2009 |
| ATXN1L | NM_001137675 | 309 | ataxin 1-like | hsa-miR-4458 | >−0.02 | 0.93 | |
| NIPA1 | NM_001142275 | 310 | non imprinted in Prader-Willi/Angelman syndrome 1 | hsa-miR-4458 | −0.2 | 0.99 | 2007, 2009 |
| RBFOX1 | NM_001142333 | 311 | RNA binding protein, fox-1 homolog (*C. elegans*) 1 | hsa-let-7f | −0.18 | 0.86 | 2005, 2007, 2009 |
| GNAL | NM_001142339 | 312 | guanine nucleotide binding protein (G protein), alpha activating activity polypeptide, olfactory type | hsa-miR-4500 | −0.13 | 0.95 | 2005, 2007, 2009 |
| SCN4B | NM_001142348 | 313 | sodium channel, voltage-gated, type IV, beta | hsa-miR-98 | −0.08 | 0.93 | 2009 |
| CTIF | NM_001142397 | 314 | CBP80/20-dependent translation initiation factor | hsa-let-7a | −0.1 | 0.77 | |
| RPUSD3 | NM_001142547 | 315 | RNA pseudouridylate synthase domain containing 3 | hsa-miR-4500 | −0.42 | 0.89 | 2007, 2009 |
| BBX | NM_001142568 | 316 | bobby sox homolog (*Drosophila*) | hsa-let-7d | −0.11 | 0.81 | |
| CLP1 | NM_001142597 | 317 | CLP1, cleavage and polyadenylation factor I subunit, homolog (*S. cerevisiae*) | hsa-miR-4458 | −0.32 | 0.68 | 2007 |
| TMOD2 | NM_001142885 | 318 | tropomodulin 2 (neuronal) | hsa-miR-4458 | −0.12 | 0.98 | |
| PLEKHG6 | NM_001144856 | 319 | pleckstrin homology domain containing, family G (with RhoGef domain) member 6 | hsa-miR-4458 | −0.37 | 0.98 | 2007, 2009 |
| LIPT2 | NM_001144869 | 320 | lipoyl(octanoyl) transferase 2 (putative) | hsa-miR-4458 | −0.43 | 0.87 | |
| SLC30A7 | NM_001144884 | 321 | solute carrier family 30 (zinc transporter), member 7 | hsa-let-7d | −0.07 | 0.9 | 2009 |
| NEDD4L | NM_001144964 | 322 | neural precursor cell expressed, developmentally down-regulated 4-like | hsa-miR-4500 | −0.06 | 0.94 | |
| PALM3 | NM_001145028 | 323 | paralemmin 3 | hsa-miR-4458 | −0.12 | 0.91 | |
| LRRC10B | NM_001145077 | 324 | leucine rich repeat containing 10B | hsa-let-7a | −0.07 | 0.62 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| GRID2IP | NM_001145118 | 325 | glutamate receptor, ionotropic, delta 2 (Grid2) interacting protein | hsa-miR-4458 | −0.26 | 0.94 | |
| CDK6 | NM_001145306 | 326 | cyclin-dependent kinase 6 | hsa-miR-4458 | −0.08 | 0.85 | |
| ZNF566 | NM_001145343 | 327 | zinc finger protein 566 | hsa-let-7f | −0.25 | 0.93 | 2009 |
| ZNF652 | NM_001145365 | 328 | zinc finger protein 652 | hsa-miR-4458 | −0.15 | >0.99 | |
| POTEM | NM_001145442 | 329 | POTE ankyrin domain family, member M | hsa-miR-4500 | −0.22 | <0.1 | |
| ZNF200 | NM_001145446 | 330 | zinc finger protein 200 | hsa-let-7d | −0.37 | >0.99 | 2009 |
| SOX6 | NM_001145811 | 331 | SRY (sex determining region Y)-box 6 | hsa-let-7d | −0.16 | 0.72 | |
| SLCO5A1 | NM_001146008 | 332 | solute carrier organic anion transporter family, member 5A1 | hsa-miR-4500 | −0.08 | 0.81 | 2005, 2007, 2009 |
| NEK3 | NM_001146099 | 333 | NIMA (never in mitosis gene a)-related kinase 3 | hsa-miR-4500 | −0.35 | 0.91 | 2009 |
| SLC6A15 | NM_001146335 | 334 | solute carrier family 6 (neutral amino acid transporter), member 15 | hsa-miR-4500 | −0.15 | 0.94 | |
| SLC25A4 | NM_001151 | 335 | solute carrier family 25 (mitochondrial carrier; adenine nucleotide translocator), member 4 | hsa-miR-4500 | −0.15 | 0.94 | 2005, 2007 |
| KLF8 | NM_001159296 | 336 | Kruppel-like factor 8 | hsa-miR-4458 | −0.11 | 0.81 | |
| BEGAIN | NM_001159531 | 337 | brain-enriched guanylate kinase-associated homolog (rat) | hsa-miR-4458 | −0.36 | 0.99 | 2005, 2007, 2009 |
| BEND4 | NM_001159547 | 338 | BEN domain containing 4 | hsa-miR-98 | −0.24 | >0.99 | 2009 |
| SYNCRIP | NM_001159673 | 339 | synaptotagmin binding, cytoplasmic RNA interacting protein | hsa-miR-4458 | −0.29 | 0.96 | |
| BZW2 | NM_001159767 | 340 | basic leucine zipper and W2 domains 2 | hsa-let-7a | −0.24 | 0.81 | 2007, 2009 |
| CANT1 | NM_001159772 | 341 | calcium activated nucleotidase 1 | hsa-miR-4458 | −0.19 | 0.89 | 2009 |
| ZNF583 | NM_001159860 | 342 | zinc finger protein 583 | hsa-let-7f | −0.44 | 0.98 | 2007, 2009 |
| RNF170 | NM_001160223 | 343 | ring finger protein 170 | hsa-let-7d | −0.41 | 0.98 | |
| PANX2 | NM_001160300 | 344 | pannexin 2 | hsa-miR-4458 | −0.1 | 0.92 | 2005, 2007, 2009 |
| TMC7 | NM_001160364 | 345 | transmembrane channel-like 7 | hsa-let-7d | −0.12 | 0.92 | 2005, 2007, 2009 |
| IGF2BP1 | NM_001160423 | 346 | insulin-like growth factor 2 mRNA binding protein 1 | hsa-miR-4500 | −0.4 | >0.99 | 2007, 2009 |
| SYNC | NM_001161708 | 347 | syncoilin, intermediate filament protein | hsa-miR-4500 | −0.48 | <0.1 | |
| SULF2 | NM_001161841 | 348 | sulfatase 2 | hsa-miR-4458 | −0.12 | 0.91 | |
| APBA1 | NM_001163 | 349 | amyloid beta (A4) precursor protein-binding, family A, member 1 | hsa-let-7a | −0.11 | 0.94 | |
| CECR6 | NM_001163079 | 350 | cat eye syndrome chromosome region, candidate 6 | hsa-let-7d | −0.14 | 0.95 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| PCYT1B | NM_001163264 | 351 | phosphate cytidylyltransferase 1, choline, beta | hsa-miR-4458 | >−0.02 | 0.91 | 2007, 2009 |
| CPA4 | NM_001163446 | 352 | carboxypeptidase A4 | hsa-miR-4458 | −0.37 | 0.93 | 2005, 2007, 2009 |
| GTF2I | NM_001163636 | 353 | general transcription factor IIi | hsa-miR-4458 | −0.2 | 0.85 | 2007, 2009 |
| DLC1 | NM_001164271 | 354 | deleted in liver cancer 1 | hsa-miR-4458 | −0.22 | >0.99 | 2005, 2007, 2009 |
| SLC37A4 | NM_001164277 | 355 | solute carrier family 37 (glucose-6-phosphate transporter), member 4 | hsa-let-7d | −0.11 | 0.7 | |
| ANKRD33B | NM_001164440 | 356 | ankyrin repeat domain 33B | hsa-miR-4458 | >−0.03 | 0.25 | |
| C16orf52 | NM_001164579 | 357 | chromosome 16 open reading frame 52 | hsa-miR-4458 | −0.09 | 0.83 | |
| KIAA1549 | NM_001164665 | 358 | KIAA1549 | hsa-miR-4458 | >−0.02 | 0.94 | 2009 |
| PITPNM3 | NM_001165966 | 359 | PITPNM family member 3 | hsa-miR-4458 | >−0.02 | 0.94 | |
| EPB41 | NM_001166005 | 360 | erythrocyte membrane protein band 4.1 (elliptocytosis 1, RH-linked) | hsa-let-7a | −0.06 | 0.76 | 2009 |
| CEP120 | NM_001166226 | 361 | centrosomal protein 120 kDa | hsa-miR-4458 | −0.22 | 0.92 | 2007, 2009 |
| GRIK2 | NM_001166247 | 362 | glutamate receptor, ionotropic, kainate 2 | hsa-miR-4500 | −0.12 | 0.86 | 2005, 2007, 2009 |
| SPATA13 | NM_001166271 | 363 | spermatogenesis associated 13 | hsa-miR-4458 | >−0.02 | 0.64 | |
| TRAPPC1 | NM_001166621 | 364 | trafficking protein particle complex 1 | hsa-miR-4458 | N/A | 0.12 | 2005, 2007, 2009 |
| TMED5 | NM_001167830 | 365 | transmembrane emp24 protein transport domain containing 5 | hsa-miR-4500 | −0.11 | 0.95 | 2005, 2007, 2009 |
| SBNO1 | NM_001167856 | 366 | strawberry notch homolog 1 (Drosophila) | hsa-miR-4458 | −0.17 | 0.95 | |
| TIMM17B | NM_001167947 | 367 | translocase of inner mitochondrial membrane 17 homolog B (yeast) | hsa-miR-4458 | −0.16 | 0.93 | 2005, 2007, 2009 |
| GPR156 | NM_001168271 | 368 | G protein-coupled receptor 156 | hsa-miR-4458 | −0.21 | 0.95 | |
| EDN1 | NM_001168319 | 369 | endothelin 1 | hsa-miR-4500 | −0.31 | 0.86 | 2009 |
| TXLNG | NM_001168683 | 370 | taxilin gamma | hsa-miR-4500 | −0.32 | 0.95 | |
| TMEM135 | NM_001168724 | 371 | transmembrane protein 135 | hsa-let-7a | −0.11 | 0.93 | |
| AFF2 | NM_001169122 | 372 | AF4/FMR2 family, member 2 | hsa-miR-4458 | −0.22 | 0.92 | 2009 |
| GPR137 | NM_001170726 | 373 | G protein-coupled receptor 137 | hsa-let-7b | −0.16 | 0.67 | 2003, 2007, 2009 |
| LCOR | NM_001170765 | 374 | ligand dependent nuclear receptor corepressor | hsa-miR-4500 | −0.14 | 0.96 | 2007, 2009 |
| IGSF1 | NM_001170963 | 375 | immunoglobulin superfamily, member 1 | hsa-let-7f | −0.38 | 0.93 | 2009 |
| STRBP | NM_001171137 | 376 | spermatid perinuclear RNA binding protein | hsa-miR-4458 | −0.2 | 0.89 | 2005, 2007, 2009 |
| C3orf52 | NM_001171747 | 377 | chromosome 3 open reading frame 52 | hsa-miR-4458 | −0.23 | 0.85 | 2009 |
| CSRNP3 | NM_001172173 | 378 | cysteine-serine-rich nuclear protein 3 | hsa-let-7c | −0.05 | 0.87 | |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| OLR1 | NM_001172632 | 379 | oxidized low density lipoprotein (lectin-like) receptor 1 | hsa-miR-4458 | −0.12 | 0.88 | 2005, 2007, 2009 |
| RAB40C | NM_001172663 | 380 | RAB40C, member RAS oncogene family | hsa-let-7a | −0.1 | 0.91 | 2005, 2007, 2009 |
| ZNF347 | NM_001172674 | 381 | zinc finger protein 347 | hsa-miR-4458 | −0.41 | <0.1 | |
| ZNF641 | NM_001172681 | 382 | zinc finger protein 641 | hsa-miR-4458 | −0.2 | 0.93 | |
| PPARGC1B | NM_001172698 | 383 | peroxisome proliferator-activated receptor gamma, coactivator 1 beta | hsa-miR-4500 | −0.31 | >0.99 | 2005, 2007, 2009 |
| PPP1R16B | NM_001172735 | 384 | protein phosphatase 1, regulatory (inhibitor) subunit 16B | hsa-miR-4458 | −0.07 | 0.94 | 2005, 2007, 2009 |
| FOXP2 | NM_001172766 | 385 | forkhead box P2 | hsa-miR-4500 | −0.33 | >0.99 | |
| CRBN | NM_001173482 | 386 | cereblon | hsa-miR-4458 | −0.2 | 0.74 | |
| LMX1A | NM_001174069 | 387 | LIM homeobox transcription factor 1, alpha | hsa-miR-98 | −0.16 | 0.92 | 2007, 2009 |
| POLL | NM_001174084 | 388 | polymerase (DNA directed), lambda | hsa-miR-4458 | −0.31 | <0.1 | 2009 |
| NCOA3 | NM_001174087 | 389 | nuclear receptor coactivator 3 | hsa-miR-4458 | −0.1 | 0.84 | 2005, 2007 |
| TRPM6 | NM_001177310 | 390 | transient receptor potential cation channel, subfamily M, member 6 | hsa-miR-4458 | −0.2 | 0.98 | 2005, 2007, 2009 |
| CPEB2 | NM_001177381 | 391 | cytoplasmic polyadenylation element binding protein 2 | hsa-let-7b | −0.21 | 0.98 | 2005, 2007, 2009 |
| HDX | NM_001177478 | 392 | highly divergent homeobox | hsa-let-7g | −0.38 | 0.97 | |
| PPP2R2A | NM_001177591 | 393 | protein phosphatase 2, regulatory subunit B, alpha | hsa-miR-4458 | −0.19 | 0.94 | |
| STX3 | NM_001178040 | 394 | syntaxin 3 | hsa-let-7g | −0.41 | 0.98 | 2007, 2009 |
| PARP8 | NM_001178055 | 395 | poly (ADP-ribose) polymerase family, member 8 | hsa-miR-4458 | −0.23 | 0.98 | |
| BCAT1 | NM_001178091 | 396 | branched chain amino-acid transaminase 1, cytosolic | hsa-miR-4500 | −0.1 | 0.95 | 2009 |
| CPEB3 | NM_001178137 | 397 | cytoplasmic polyadenylation element binding protein 3 | hsa-miR-4458 | −0.15 | 0.96 | 2005, 2007, 2009 |
| SLAMF6 | NM_001184714 | 398 | SLAM family member 6 | hsa-miR-4458 | −0.22 | 0.88 | 2007, 2009 |
| PEX11B | NM_001184795 | 399 | peroxisomal biogenesis factor 11 beta | hsa-miR-4458 | −0.34 | 0.51 | 2009 |
| PHF8 | NM_001184896 | 400 | PHD finger protein 8 | hsa-miR-4458 | >−0.02 | 0.92 | 2005, 2007, 2009 |
| CLDN12 | NM_001185072 | 401 | claudin 12 | hsa-miR-4458 | −0.34 | 0.98 | 2005, 2007, 2009 |
| BACH1 | NM_001186 | 402 | BTB and CNC homology 1, basic leucine zipper transcription factor 1 | hsa-let-7c | −0.31 | >0.99 | 2005, 2007, 2009 |
| ATG16L1 | NM_001190266 | 403 | ATG16 autophagy related 16-like 1 (*S. cerevisiae*) | hsa-miR-4458 | −0.09 | 0.92 | 2007, 2009 |
| NCOR1 | NM_001190440 | 404 | nuclear receptor corepressor 1 | hsa-miR-4458 | −0.05 | 0.92 | |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| COL11A1 | NM_001190709 | 405 | collagen, type XI, alpha 1 | hsa-miR-4458 | −0.1 | 0.77 | |
| YAF2 | NM_001190977 | 406 | YY1 associated factor 2 | hsa-let-7a | −0.05 | 0.94 | 2009 |
| BCL2L1 | NM_001191 | 407 | BCL2-like 1 | hsa-miR-4458 | −0.2 | 0.9 | 2005, 2007, 2009 |
| IKBKE | NM_001193321 | 408 | inhibitor of kappa light polypeptide gene enhancer in B-cells, kinase epsilon | hsa-let-7b | −0.13 | 0.94 | 2005, 2007, 2009 |
| SECISBP2L | NM_001193489 | 409 | SECIS binding protein 2-like | hsa-miR-4458 | −0.08 | 0.81 | |
| SLC1A4 | NM_001193493 | 410 | solute carrier family 1 (glutamate/neutral amino acid transporter), member 4 | hsa-let-7d | −0.05 | 0.98 | 2009 |
| SLC30A6 | NM_001193513 | 411 | solute carrier family 30 (zinc transporter), member 6 | hsa-miR-4458 | −0.31 | 0.92 | |
| POGZ | NM_001194937 | 412 | pogo transposable element with ZNF domain | hsa-miR-4458 | −0.16 | 0.88 | 2005, 2007, 2009 |
| PTPRU | NM_001195001 | 413 | protein tyrosine phosphatase, receptor type, U | hsa-let-7a | −0.14 | 0.92 | 2009 |
| ANKRD28 | NM_001195098 | 414 | ankyrin repeat domain 28 | hsa-miR-4458 | −0.2 | 0.84 | 2009 |
| PTP4A2 | NM_001195100 | 415 | protein tyrosine phosphatase type IVA, member 2 | hsa-let-7b | −0.07 | 0.75 | |
| LOC100507421 | NM_001195278 | 416 | transmembrane protein 178-like | hsa-miR-4458 | −0.06 | 0.85 | |
| DICER1 | NM_001195573 | 417 | dicer 1, ribonuclease type III | hsa-miR-4458 | −0.05 | >0.99 | 2009 |
| MLLT10 | NM_001195626 | 418 | myeloid/lymphoid or mixed-lineage leukemia (trithorax homolog, *Drosophila*); translocated to, 10 | hsa-let-7i | −0.15 | 0.86 | 2005, 2007, 2009 |
| TGFBR3 | NM_001195683 | 419 | transforming growth factor, beta receptor III | hsa-let-7g | −0.39 | 0.98 | |
| PLD5 | NM_001195811 | 420 | phospholipase D family, member 5 | hsa-miR-98 | −0.18 | 0.86 | |
| PLEKHA8 | NM_001197026 | 421 | pleckstrin homology domain containing, family A (phosphoinositide binding specific) member 8 | hsa-let-7a | −0.32 | 0.99 | |
| DPYSL3 | NM_001197294 | 422 | dihydropyrimidinase-like 3 | hsa-miR-4500 | −0.03 | 0.84 | 2009 |
| GABPA | NM_001197297 | 423 | GA binding protein transcription factor, alpha subunit 60 kDa | hsa-miR-4500 | −0.09 | 0.92 | 2007, 2009 |
| PRDM1 | NM_001198 | 424 | PR domain containing 1, with ZNF domain | hsa-let-7a | −0.05 | 0.74 | 2005, 2007, 2009 |
| RUNX1T1 | NM_001198625 | 425 | runt-related transcription factor 1; translocated to, 1 (cyclin D-related) | hsa-miR-4458 | −0.05 | 0.91 | |
| POU2F1 | NM_001198783 | 426 | POU class 2 homeobox 1 | hsa-miR-4458 | −0.02 | >0.99 | |
| A1CF | NM_001198818 | 427 | APOBEC1 complementation factor | hsa-miR-4500 | −0.11 | <0.1 | |
| ABCC10 | NM_001198934 | 428 | ATP-binding cassette, sub-family C (CFTR/MRP), member 10 | hsa-miR-4458 | −0.16 | 0.82 | 2005, 2007 |
| SMAP2 | NM_001198978 | 429 | small ArfGAP2 | hsa-miR-4458 | −0.21 | 0.82 | 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| AMMECR1L | NM_001199140 | 430 | AMME chromosomal region gene 1-like | hsa-let-7d | −0.11 | <0.1 | 2007, 2009 |
| TOR1AIP2 | NM_001199260 | 431 | torsin A interacting protein 2 | hsa-miR-4458 | >−0.03 | 0.98 | |
| UCHL5 | NM_001199261 | 432 | ubiquitin carboxyl-terminal hydrolase L5 | hsa-let-7f | −0.04 | <0.1 | |
| PHOSPHO2-KLHL23 | NM_001199290 | 433 | PHOSPHO2-KLHL23 readthrough | hsa-let-7f | −0.2 | 0.95 | |
| CNOT2 | NM_001199302 | 434 | CCR4-NOT transcription complex, subunit 2 | hsa-let-7d | −0.14 | 0.86 | 2007, 2009 |
| MUTED | NM_001199322 | 435 | muted homolog (mouse) | hsa-let-7c | −0.1 | 0.82 | 2009 |
| CPD | NM_001199775 | 436 | carboxypeptidase D | hsa-let-7d | −0.18 | 0.95 | 2005, 2007, 2009 |
| POC1B-GALNT4 | NM_001199781 | 437 | POC1B-GALNT4 readthrough | hsa-let-7a | −0.1 | 0.84 | |
| EGR3 | NM_001199880 | 438 | early growth response 3 | hsa-miR-4458 | >−0.03 | 0.67 | 2005, 2007, 2009 |
| DNAL1 | NM_001201366 | 439 | dynein, axonemal, light chain 1 | hsa-miR-4458 | −0.03 | 0.94 | 2009 |
| RNF7 | NM_001201370 | 440 | ring finger protein 7 | hsa-miR-4458 | −0.18 | 0.94 | 2005, 2007, 2009 |
| TRMT1L | NM_001202423 | 441 | TRM1 tRNA methyltransferase 1-like | hsa-miR-4458 | −0.16 | 0.65 | |
| HSPE1-MOBKL3 | NM_001202485 | 442 | HSPE1-MOBKL3 readthrough | hsa-let-7a | −0.12 | 0.93 | |
| UBE2G2 | NM_001202489 | 443 | ubiquitin-conjugating enzyme E2G 2 | hsa-miR-4458 | −0.14 | 0.94 | 2009 |
| MXD1 | NM_001202513 | 444 | MAX dimerization protein 1 | hsa-miR-4458 | −0.23 | 0.94 | 2007, 2009 |
| CUX1 | NM_001202543 | 445 | cut-like homeobox 1 | hsa-miR-4458 | −0.05 | 0.77 | |
| SEMA4G | NM_001203244 | 446 | sema domain, immunoglobulin domain (Ig), transmembrane domain (TM) and short cytoplasmic domain, (semaphorin) 4G | hsa-let-7a | −0.22 | 0.9 | 2005, 2007, 2009 |
| EZH2 | NM_001203247 | 447 | enhancer of zeste homolog 2 (Drosophila) | hsa-miR-4458 | N/A | 0.86 | 2005, 2007, 2009 |
| PPT2 | NM_001204103 | 448 | palmitoyl-protein thioesterase 2 | hsa-miR-4458 | −0.29 | <0.1 | |
| MDM4 | NM_001204171 | 449 | Mdm4 p53 binding protein homolog (mouse) | hsa-let-7a | −0.27 | >0.99 | |
| RGS6 | NM_001204416 | 450 | regulator of G-protein signaling 6 | hsa-miR-4458 | −0.22 | 0.95 | 2009 |
| NPEPL1 | NM_001204872 | 451 | aminopeptidase-like 1 | hsa-let-7f | −0.15 | 0.94 | 2005, 2007, 2009 |
| PBX1 | NM_001204961 | 452 | pre-B-cell leukemia homeobox 1 | hsa-let-7g | −0.28 | 0.94 | |
| KLF9 | NM_001206 | 453 | Kruppel-like factor 9 | hsa-miR-4500 | −0.18 | 0.92 | 2005, 2007, 2009 |
| CD86 | NM_001206924 | 454 | CD86 molecule | hsa-miR-4500 | −0.2 | 0.6 | 2009 |
| POU2F2 | NM_001207025 | 455 | POU class 2 homeobox 2 | hsa-miR-4458 | −0.14 | 0.89 | 2007, 2009 |
| CLASP2 | NM_001207044 | 456 | cytoplasmic linker associated protein 2 | hsa-let-7g | −0.14 | 0.94 | 2005, 2007, 2009 |
| BZW1 | NM_001207067 | 457 | basic leucine zipper and W2 domains 1 | hsa-let-7f | −0.48 | 0.99 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| MEIS2 | NM_001220482 | 458 | Meis homeobox 2 | hsa-miR-4458 | −0.18 | 0.86 | 2005, 2007, 2009 |
| CCNT2 | NM_001241 | 459 | cyclin T2 | hsa-miR-4458 | −0.1 | 0.76 | |
| ATAD2B | NM_001242338 | 460 | ATPase family, AAA domain containing 2B | hsa-miR-4458 | >−0.03 | 0.66 | 2009 |
| FAM59A | NM_001242409 | 461 | family with sequence similarity 59, member A | hsa-let-7f | −0.17 | 0.94 | |
| FBXO32 | NM_001242463 | 462 | F-box protein 32 | hsa-let-7b | −0.26 | 0.95 | |
| MAP4K4 | NM_001242559 | 463 | mitogen-activated protein kinase kinase kinase kinase 4 | hsa-miR-4458 | −0.2 | 0.99 | 2005, 2007, 2009 |
| NXT2 | NM_001242617 | 464 | nuclear transport factor 2-like export factor 2 | hsa-let-7g | −0.21 | 0.86 | 2005, 2007, 2009 |
| GFOD1 | NM_001242628 | 465 | glucose-fructose oxidoreductase domain containing 1 | hsa-miR-4458 | −0.29 | <0.1 | |
| ARHGEF38 | NM_001242729 | 466 | Rho guanine nucleotide exchange factor (GEF) 38 | hsa-miR-4500 | −0.53 | 0.94 | |
| ZNF322A | NM_001242797 | 467 | zinc finger protein 322A | hsa-let-7a | −0.47 | 0.96 | 2009 |
| CHD4 | NM_001273 | 468 | chromodomain helicase DNA binding protein 4 | hsa-miR-4500 | −0.17 | 0.83 | 2005, 2007, 2009 |
| CHUK | NM_001278 | 469 | conserved helix-loop-helix ubiquitous kinase | hsa-miR-4500 | −0.27 | 0.74 | |
| AP1S1 | NM_001283 | 470 | adaptor-related protein complex 1, sigma 1 subunit | hsa-miR-4458 | −0.27 | 0.88 | 2005, 2007, 2009 |
| DUSP4 | NM_001394 | 471 | dual specificity phosphatase 4 | hsa-miR-4500 | −0.17 | 0.94 | 2007, 2009 |
| DUSP9 | NM_001395 | 472 | dual specificity phosphatase 9 | hsa-miR-4500 | −0.07 | 0.93 | 2005, 2007, 2009 |
| DYRK1A | NM_001396 | 473 | dual-specificity tyrosine-(Y)-phosphorylation regulated kinase 1A | hsa-miR-4500 | −0.15 | 0.84 | 2005, 2007, 2009 |
| GATM | NM_001482 | 474 | glycine amidinotransferase (L-arginine:glycine amidinotransferase) | hsa-let-7a | −0.44 | 0.96 | 2009 |
| ACVR2A | NM_001616 | 475 | activin A receptor, type IIA | hsa-let-7a | −0.24 | 0.98 | 2007, 2009 |
| AKT2 | NM_001626 | 476 | v-akt marine thymoma viral oncogene homolog 2 | hsa-let-7i | −0.15 | 0.88 | 2009 |
| ARL4D | NM_001661 | 477 | ADP-ribosylation factor-like 4D | hsa-miR-4500 | −0.19 | 0.94 | 2009 |
| POLR3D | NM_001722 | 478 | polymerase (RNA) III (DNA directed) polypeptide D, 44 kDa | hsa-miR-4500 | −0.28 | 0.91 | 2007, 2009 |
| CCND2 | NM_001759 | 479 | cyclin D2 | hsa-miR-4458 | −0.14 | >0.99 | 2005, 2007, 2009 |
| CCNF | NM_001761 | 480 | cyclin F | hsa-let-7d | −0.4 | 0.92 | 2009 |
| CDC25A | NM_001789 | 481 | cell division cycle 25 homolog A (*S. pombe*) | hsa-miR-4458 | −0.42 | 0.9 | 2005, 2007, 2009 |
| CCR7 | NM_001838 | 482 | chemokine (C-C motif) receptor 7 | hsa-let-7f | −0.36 | 0.96 | 2005, 2007, 2009 |
| COL4A1 | NM_001845 | 483 | collagen, type IV, alpha 1 | hsa-miR-4458 | −0.15 | 0.92 | 2005, 2007, 2009 |
| COL4A2 | NM_001846 | 484 | collagen, type IV, alpha 2 | hsa-miR-98 | −0.17 | 0.94 | 2005, 2007, 2009 |
| COL4A6 | NM_001847 | 485 | collagen, type IV, alpha 6 | hsa-miR-4458 | −0.34 | <0.1 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| COL9A3 | NM_001853 | 486 | collagen, type IX, alpha 3 | hsa-let-7a | −0.11 | 0.86 | 2009 |
| COL15A1 | NM_001855 | 487 | collagen, type XV, alpha 1 | hsa-miR-4500 | −0.18 | 0.93 | 2005, 2007, 2009 |
| SLC31A1 | NM_001859 | 488 | solute carrier family 31 (copper transporters), member 1 | hsa-miR-4458 | −0.12 | 0.94 | 2009 |
| SLC31A2 | NM_001860 | 489 | solute carrier family 31 (copper transporters), member 2 | hsa-let-7a | −0.17 | 0.71 | 2005, 2007 |
| MASP1 | NM_001879 | 490 | mannan-binding lectin serine peptidase 1 (C4/C2 activating component of Ra-reactive factor) | hsa-let-7a | −0.34 | 0.94 | 2007, 2009 |
| CTPS | NM_001905 | 491 | CTP synthase | hsa-miR-4458 | −0.19 | 0.79 | |
| DLST | NM_001933 | 492 | dihydrolipoamide S-succinyltransferase (E2 component of 2-oxo-glutarate complex) | hsa-miR-4500 | −0.17 | 0.95 | 2005, 2007, 2009 |
| DSG3 | NM_001944 | 493 | desmoglein 3 | hsa-miR-4500 | −0.16 | <0.1 | |
| HBEGF | NM_001945 | 494 | heparin-binding EGF-like growth factor | hsa-miR-4500 | −0.17 | 0.73 | |
| DUSP7 | NM_001947 | 495 | dual specificity phosphatase 7 | hsa-let-7b | −0.07 | 0.94 | |
| ELK4 | NM_001973 | 496 | ELK4, ETS-domain protein (SRF accessory protein 1) | hsa-miR-4458 | −0.14 | 0.94 | |
| EZH1 | NM_001991 | 497 | enhancer of zeste homolog 1 (Drosophila) | hsa-let-7a | −0.14 | 0.88 | 2009 |
| GLRX | NM_002064 | 498 | glutaredoxin (thioltransferase) | hsa-let-7d | −0.23 | 0.78 | 2009 |
| GNS | NM_002076 | 499 | glucosamine (N-acetyl)-6-sulfatase | hsa-miR-4458 | >−0.01 | 0.88 | 2005, 2007, 2009 |
| HLF | NM_002126 | 500 | hepatic leukemia factor | hsa-miR-4500 | −0.06 | 0.87 | 2007, 2009 |
| HMGA1 | NM_002131 | 501 | high mobility group AT-hook 1 | hsa-let-7i | −0.25 | 0.94 | 2005, 2007, 2009 |
| IDH2 | NM_002168 | 502 | isocitrate dehydrogenase 2 (NADP+), mitochondrial | hsa-let-7d | −0.12 | 0.83 | 2005, 2007 |
| IL13 | NM_002188 | 503 | interleukin 13 | hsa-miR-4500 | −0.32 | 0.98 | 2005, 2007, 2009 |
| ITGB8 | NM_002214 | 504 | integrin, beta 8 | hsa-let-7i | −0.1 | 0.94 | 2007, 2009 |
| KCNA6 | NM_002235 | 505 | potassium voltage-gated channel, shaker-related subfamily, member 6 | hsa-miR-4458 | >−0.03 | 0.44 | 2009 |
| KPNA1 | NM_002264 | 506 | karyopherin alpha 1 (importin alpha 5) | hsa-miR-4458 | −0.15 | 0.93 | 2007, 2009 |
| KPNA4 | NM_002268 | 507 | karyopherin alpha 4 (importin alpha 3) | hsa-miR-4458 | −0.08 | 0.97 | 2005, 2007 |
| LBR | NM_002296 | 508 | lamin B receptor | hsa-miR-4458 | −0.21 | 0.98 | 2009 |
| LY75 | NM_002349 | 509 | lymphocyte antigen 75 | hsa-let-7d | −0.17 | 0.8 | 2009 |
| MAP3K3 | NM_002401 | 510 | mitogen-activated protein kinase kinase kinase 3 | hsa-miR-4458 | −0.06 | 0.95 | 2005, 2007, 2009 |
| MSR1 | NM_002445 | 511 | macrophage scavenger receptor 1 | hsa-let-7a | −0.37 | 0.98 | |
| NGF | NM_002506 | 512 | nerve growth factor (beta polypeptide) | hsa-miR-4458 | −0.34 | 0.93 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| NOVA1 | NM_002515 | 513 | neuro-oncological ventral antigen 1 | hsa-let-7d | −0.11 | 0.92 | 2005, 2007, 2009 |
| NRAS | NM_002524 | 514 | neuroblastoma RAS viral (v-ras) oncogene homolog | hsa-miR-4500 | −0.35 | >0.99 | 2005, 2007, 2009 |
| P2RX1 | NM_002558 | 515 | purinergic receptor P2X, ligand-gated ion channel, 1 | hsa-miR-4458 | −0.12 | 0.9 | 2009 |
| PAPPA | NM_002581 | 516 | pregnancy-associated plasma protein A, pappalysin 1 | hsa-miR-98 | −0.2 | >0.99 | 2005, 2007, 2009 |
| PBX2 | NM_002586 | 517 | pre-B-cell leukemia homeobox 2 | hsa-miR-4500 | −0.22 | >0.99 | 2005, 2007, 2009 |
| PDGFB | NM_002608 | 518 | platelet-derived growth factor beta polypeptide | hsa-miR-4458 | −0.11 | 0.88 | 2005, 2007, 2009 |
| PIGA | NM_002641 | 519 | phosphatidylinositol glycan anchor biosynthesis, class A | hsa-miR-4500 | −0.29 | 0.94 | 2005, 2007, 2009 |
| PLAGL2 | NM_002657 | 520 | pleiomorphic adenoma gene-like 2 | hsa-miR-4500 | −0.12 | 0.91 | 2005, 2007, 2009 |
| MAPK6 | NM_002748 | 521 | mitogen-activated protein kinase 6 | hsa-let-7b | −0.38 | 0.94 | 2005, 2007, 2009 |
| MAPK11 | NM_002751 | 522 | mitogen-activated protein kinase 11 | hsa-miR-4458 | −0.11 | 0.79 | 2009 |
| MAPK9 | NM_002752 | 523 | mitogen-activated protein kinase 9 | hsa-miR-4458 | −0.05 | 0.77 | |
| PTPRO | NM_002848 | 524 | protein tyrosine phosphatase, receptor type, O | hsa-let-7d | −0.14 | 0.88 | 2009 |
| RALB | NM_002881 | 525 | v-ral simian leukemia viral oncogene homolog B (ras related; GTP binding protein) | hsa-miR-4458 | −0.17 | 0.94 | 2009 |
| RBMS1 | NM_002897 | 526 | RNA binding motif, single stranded interacting protein 1 | hsa-let-7d | −0.25 | 0.96 | |
| RBMS2 | NM_002898 | 527 | RNA binding motif, single stranded interacting protein 2 | hsa-let-7a | −0.1 | 0.98 | |
| RCN1 | NM_002901 | 528 | reticulocalbin 1, EF-hand calcium binding domain | hsa-let-7d | −0.17 | 0.85 | 2009 |
| RDX | NM_002906 | 529 | radixin | hsa-let-7a | −0.25 | 0.75 | 2005, 2007, 2009 |
| RGS16 | NM_002928 | 530 | regulator of G-protein signaling 16 | hsa-miR-4500 | −0.31 | 0.98 | 2005, 2007, 2009 |
| S100A8 | NM_002964 | 531 | S100 calcium binding protein A8 | hsa-miR-4500 | −0.18 | 0.69 | |
| CCL3 | NM_002983 | 532 | chemokine (C-C motif) ligand 3 | hsa-miR-4458 | −0.23 | 0.87 | 2009 |
| ST3GAL1 | NM_003033 | 533 | ST3 beta-galactoside alpha-2,3-sialyltransferase 1 | hsa-miR-4458 | >−0.01 | 0.89 | |
| ST8SIA1 | NM_003034 | 534 | ST8 alpha-N-acetyl-neuraminide alpha-2,8-sialyltransferase 1 | hsa-let-7f | −0.29 | 0.94 | 2009 |
| SLC6A1 | NM_003042 | 535 | solute carrier family 6 (neurotransmitter transporter, GABA), member 1 | hsa-miR-4458 | −0.19 | 0.95 | 2005, 2007, 2009 |
| SMARCC1 | NM_003074 | 536 | SWI/SNF related, matrix associated, actin dependent regulator of chromatin, subfamily c, member 1 | hsa-let-7g | −0.13 | 0.91 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| SNX1 | NM_003099 | 537 | sorting nexin 1 | hsa-miR-4458 | −0.2 | <0.1 | 2009 |
| STRN | NM_003162 | 538 | striatin, calmodulin binding protein | hsa-miR-4458 | −0.14 | 0.95 | |
| TEAD3 | NM_003214 | 539 | TEA domain family member 3 | hsa-miR-4458 | −0.08 | 0.91 | 2007, 2009 |
| THBS1 | NM_003246 | 540 | thrombospondin 1 | hsa-let-7c | −0.16 | 0.86 | 2009 |
| THRSP | NM_003251 | 541 | thyroid hormone responsive | hsa-let-7d | −0.62 | 0.74 | 2009 |
| VSNL1 | NM_003385 | 542 | visinin-like 1 | hsa-miR-4458 | −0.11 | 0.79 | 2005, 2007, 2009 |
| ZNF202 | NM_003455 | 543 | zinc finger protein 202 | hsa-let-7d | −0.36 | <0.1 | |
| BSN | NM_003458 | 544 | bassoon (presynaptic cytomatrix protein) | hsa-let-7a | −0.09 | 0.94 | 2009 |
| MLL2 | NM_003482 | 545 | myeloid/lymphoid or mixed-lineage leukemia 2 | hsa-miR-4458 | −0.26 | 0.98 | 2007, 2009 |
| HMGA2 | NM_003483 | 546 | high mobility group AT-hook 2 | hsa-miR-4458 | −1.04 | >0.99 | 2005, 2007, 2009 |
| SNN | NM_003498 | 547 | stannin | hsa-miR-4458 | −0.15 | 0.87 | 2005, 2007, 2009 |
| EEA1 | NM_003566 | 548 | early endosome antigen 1 | hsa-miR-4458 | −0.21 | 0.94 | 2007, 2009 |
| ZNF282 | NM_003575 | 549 | zinc finger protein 282 | hsa-miR-4458 | >−0.02 | 0.94 | 2009 |
| DYRK2 | NM_003583 | 550 | dual-specificity tyrosine-(Y)-phosphorylation regulated kinase 2 | hsa-miR-4500 | −0.12 | 0.87 | 2009 |
| SLC4A7 | NM_003615 | 551 | solute carrier family 4, sodium bicarbonate cotransporter, member 7 | hsa-let-7g | −0.02 | 0.81 | 2005, 2007 |
| MAP4K3 | NM_003618 | 552 | mitogen-activated protein kinase kinase kinase kinase 3 | hsa-miR-98 | −0.46 | 0.96 | 2005, 2007, 2009 |
| NDST2 | NM_003635 | 553 | N-deacetylase/N-sulfotransferase (heparan glucosaminyl) 2 | hsa-miR-4458 | −0.32 | 0.96 | 2005, 2007, 2009 |
| IKBKAP | NM_003640 | 554 | inhibitor of kappa light polypeptide gene enhancer in B-cells, kinase complex-associated protein | hsa-miR-4458 | −0.27 | 0.93 | 2005, 2007, 2009 |
| CHRD | NM_003741 | 555 | chordin | hsa-miR-4458 | −0.15 | 0.87 | 2005, 2007 |
| NCOA1 | NM_003743 | 556 | nuclear receptor coactivator 1 | hsa-let-7d | −0.07 | 0.7 | 2005, 2007 |
| IRS2 | NM_003749 | 557 | insulin receptor substrate 2 | hsa-miR-4458 | −0.28 | 0.98 | 2005, 2007, 2009 |
| GALNT4 | NM_003774 | 558 | UDP-N-acetyl-alpha-D-galactosamine:polypeptide N-acetylgalactosaminyltransferase 4 (GalNAc-T4) | hsa-let-7a | −0.1 | 0.84 | 2009 |
| RNMT | NM_003799 | 559 | RNA (guanine-7-) methyltransferase | hsa-miR-4458 | −0.31 | <0.1 | |
| TNFSF9 | NM_003811 | 560 | tumor necrosis factor (ligand) superfamily, member 9 | hsa-let-7d | −0.35 | 0.98 | 2009 |
| SNAP23 | NM_003825 | 561 | synaptosomal-associated protein, 23 kDa | hsa-miR-4500 | −0.26 | 0.93 | 2005, 2007, 2009 |
| RIOK3 | NM_003831 | 562 | RIO kinase 3 (yeast) | hsa-miR-4500 | −0.26 | 0.94 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| SUCLG2 | NM_003848 | 563 | succinate-CoA ligase, GDP-forming, beta subunit | hsa-let-7a | −0.14 | 0.89 | 2009 |
| EIF2S2 | NM_003908 | 564 | eukaryotic translation initiation factor 2, subunit 2 beta, 38 kDa | hsa-miR-4458 | −0.22 | 0.92 | 2009 |
| MBD2 | NM_003927 | 565 | methyl-CpG binding domain protein 2 | hsa-let-7f | −0.29 | >0.99 | |
| WASL | NM_003941 | 566 | Wiskott-Aldrich syndrome-like | hsa-let-7d | −0.17 | 0.87 | 2009 |
| RNF8 | NM_003958 | 567 | ring finger protein 8 | hsa-miR-4500 | −0.1 | 0.68 | |
| OSMR | NM_003999 | 568 | oncostatin M receptor | hsa-miR-4458 | −0.27 | 0.94 | 2005, 2007, 2009 |
| E2F2 | NM_004091 | 569 | E2F transcription factor 2 | hsa-let-7d | −0.28 | 0.94 | 2009 |
| FGF11 | NM_004112 | 570 | fibroblast growth factor 11 | hsa-miR-98 | −0.26 | 0.93 | 2005, 2007, 2009 |
| TARBP2 | NM_004178 | 571 | TAR (HIV-1) RNA binding protein 2 | hsa-miR-4458 | −0.2 | 0.93 | 2009 |
| SEMA3F | NM_004186 | 572 | sema domain, immunoglobulin domain (Ig), short basic domain, secreted, (semaphorin) 3F | hsa-miR-4458 | −0.16 | 0.72 | 2005, 2007 |
| SYT7 | NM_004200 | 573 | synaptotagmin VII | hsa-miR-98 | −0.25 | 0.98 | 2007, 2009 |
| AURKB | NM_004217 | 574 | aurora kinase B | hsa-miR-4458 | −0.26 | 0.78 | |
| CYTH3 | NM_004227 | 575 | cytohesin 3 | hsa-miR-4458 | −0.02 | 0.9 | 2005, 2007, 2009 |
| SEMA4F | NM_004263 | 576 | sema domain, immunoglobulin domain (Ig), transmembrane domain (TM) and short cytoplasmic domain, (semaphorin) 4F | hsa-miR-4500 | −0.4 | 0.97 | 2009 |
| CHST3 | NM_004273 | 577 | carbohydrate (chondroitin 6) sulfotransferase 3 | hsa-miR-4458 | −0.11 | 0.99 | 2009 |
| AKAP6 | NM_004274 | 578 | A kinase (PRKA) anchor protein 6 | hsa-let-7c | −0.28 | 0.95 | 2005, 2007, 2009 |
| SLC25A27 | NM_004277 | 579 | solute carrier family 25, member 27 | hsa-miR-4458 | −0.29 | 0.95 | 2005, 2007, 2009 |
| ACVR1B | NM_004302 | 580 | activin A receptor, type IB | hsa-let-7g | −0.12 | 0.95 | 2005, 2007, 2009 |
| CASP3 | NM_004346 | 581 | caspase 3, apoptosis-related cysteine peptidase | hsa-let-7b | −0.4 | 0.99 | 2005, 2007, 2009 |
| CDC34 | NM_004359 | 582 | cell division cycle 34 homolog (*S. cerevisiae*) | hsa-miR-4500 | −0.47 | >0.99 | 2005, 2007, 2009 |
| DUSP1 | NM_004417 | 583 | dual specificity phosphatase 1 | hsa-miR-4500 | −0.18 | 0.87 | 2005, 2007, 2009 |
| DVL3 | NM_004423 | 584 | dishevelled, dsh homolog 3 (*Drosophila*) | hsa-let-7f | −0.41 | 0.89 | 2009 |
| EPHA4 | NM_004438 | 585 | EPH receptor A4 | hsa-miR-4500 | −0.18 | 0.87 | 2005, 2007, 2009 |
| FGF5 | NM_004464 | 586 | fibroblast growth factor 5 | hsa-miR-4458 | −0.11 | 0.93 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| GALNT2 | NM_004481 | 587 | UDP-N-acetyl-alpha-D-galactosamine:polypeptide N-acetylgalactosaminyltransferase 2 (GalNAc-T2) | hsa-miR-4500 | −0.18 | 0.94 | 2005, 2007, 2009 |
| USP6 | NM_004505 | 588 | ubiquitin specific peptidase 6 (Tre-2 oncogene) | hsa-let-7a | −0.18 | 0.92 | 2005, 2007, 2009 |
| NAP1L1 | NM_004537 | 589 | nucleosome assembly protein 1-like 1 | hsa-let-7d | −0.41 | >0.99 | 2005, 2007, 2009 |
| NRTN | NM_004558 | 590 | neurturin | hsa-miR-4458 | N/A | 0.85 | 2007, 2009 |
| RPS6KA3 | NM_004586 | 591 | ribosomal protein S6 kinase, 90 kDa, polypeptide 3 | hsa-miR-98 | −0.1 | 0.94 | 2005, 2007, 2009 |
| COIL | NM_004645 | 592 | coilin | hsa-miR-4500 | −0.5 | 0.96 | 2005, 2007, 2009 |
| KCNQ4 | NM_004700 | 593 | potassium voltage-gated channel, KQT-like subfamily, member 4 | hsa-let-7d | −0.18 | 0.94 | |
| NUMBL | NM_004756 | 594 | numb homolog (*Drosophila*)-like | hsa-miR-4500 | −0.04 | 0.94 | 2005, 2007, 2009 |
| NDST3 | NM_004784 | 595 | N-deacetylase/N-sulfotransferase (heparan glucosaminyl) 3 | hsa-let-7d | −0.18 | 0.83 | |
| POLR2D | NM_004805 | 596 | polymerase (RNA) II (DNA directed) polypeptide D | hsa-let-7b | −0.42 | <0.1 | 2009 |
| HAND1 | NM_004821 | 597 | heart and neural crest derivatives expressed 1 | hsa-let-7a | −0.44 | 0.98 | 2005, 2007, 2009 |
| NTN1 | NM_004822 | 598 | netrin 1 | hsa-miR-4500 | −0.26 | 0.84 | 2009 |
| ONECUT2 | NM_004852 | 599 | one cut homeobox 2 | hsa-miR-4500 | −0.13 | >0.99 | 2007, 2009 |
| AKAP5 | NM_004857 | 600 | A kinase (PRKA) anchor protein 5 | hsa-miR-4458 | >−0.03 | 0.72 | 2009 |
| IGDCC3 | NM_004884 | 601 | immunoglobulin superfamily, DCC subclass, member 3 | hsa-miR-4500 | −0.72 | >0.99 | 2003, 2007, 2009 |
| SEC24C | NM_004922 | 602 | SEC24 family, member C (*S. cerevisiae*) | hsa-miR-98 | −0.1 | 0.82 | 2005, 2007, 2009 |
| DAPK1 | NM_004938 | 603 | death-associated protein kinase 1 | hsa-let-7g | −0.18 | 0.93 | 2009 |
| DOCK3 | NM_004947 | 604 | dedicator of cytokinesis 3 | hsa-miR-4458 | −0.07 | 0.9 | 2005, 2007, 2009 |
| KCNC1 | NM_004976 | 605 | potassium voltage-gated channel, Shaw-related subfamily, member 1 | hsa-miR-4458 | −0.1 | 0.91 | 2009 |
| NME4 | NM_005009 | 606 | non-metastatic cells 4, protein expressed in | hsa-let-7d | −0.19 | 0.94 | 2003, 2005, 2007, 2009 |
| QARS | NM_005051 | 607 | glutaminyl-tRNA synthetase | hsa-let-7i | −0.37 | 0.2 | 2005, 2007, 2009 |
| SCD | NM_005063 | 608 | stearoyl-CoA desaturase (delta-9-desaturase) | hsa-miR-98 | −0.33 | 0.95 | 2007, 2009 |
| SIM2 | NM_005069 | 609 | single-minded homolog 2 (*Drosophila*) | hsa-let-7d | −0.08 | 0.9 | 2009 |
| ADRBK2 | NM_005160 | 610 | adrenergic, beta, receptor kinase 2 | hsa-miR-98 | −0.15 | 0.89 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| CBFA2T3 | NM_005187 | 611 | core-binding factor, runt domain, alpha subunit 2; translocated to, 3 | hsa-miR-4458 | −0.06 | 0.94 | 2005, 2007, 2009 |
| CBL | NM_005188 | 612 | Cas-Br-M (murine) ecotropic retroviral transforming sequence | hsa-miR-4500 | −0.07 | 0.96 | 2005, 2007, 2009 |
| CBX2 | NM_005189 | 613 | chromobox homolog 2 | hsa-miR-4458 | −0.15 | 0.94 | 2007, 2009 |
| CEBPD | NM_005195 | 614 | CCAAT/enhancer binding protein (C/EBP), delta | hsa-let-7d | −0.09 | 0.86 | 2009 |
| ARID3A | NM_005224 | 615 | AT rich interactive domain 3A (BRIGHT-like) | hsa-miR-4458 | −0.11 | 0.9 | 2007, 2009 |
| EPHA3 | NM_005233 | 616 | EPH receptor A3 | hsa-miR-4500 | −0.14 | 0.93 | 2005, 2007 |
| ERCC4 | NM_005236 | 617 | excision repair cross-complementing rodent repair deficiency, complementation group 4 | hsa-miR-4500 | −0.1 | 0.98 | 2009 |
| GNG5 | NM_005274 | 618 | guanine nucleotide binding protein (G protein), gamma 5 | hsa-miR-4458 | −0.28 | 0.81 | 2005, 2007, 2009 |
| HAS2 | NM_005328 | 619 | hyaluronan synthase 2 | hsa-let-7d | −0.12 | 0.87 | 2005, 2007, 2009 |
| HDLBP | NM_005336 | 620 | high density lipoprotein binding protein | hsa-miR-4458 | −0.21 | 0.98 | 2007, 2009 |
| MYCN | NM_005378 | 621 | v-myc myelocytomatosis viral related oncogene, neuroblastoma derived (avian) | hsa-let-7i | −0.34 | 0.95 | 2005, 2007, 2009 |
| NUP98 | NM_005387 | 622 | nucleoporin 98 kDa | hsa-let-7d | −0.23 | 0.85 | |
| PRKAB2 | NM_005399 | 623 | protein kinase, AMP-activated, beta 2 non-catalytic subunit | hsa-miR-4458 | >−0.02 | 0.89 | 2009 |
| SLC20A1 | NM_005415 | 624 | solute carrier family 20 (phosphate transporter), member 1 | hsa-miR-4458 | −0.31 | 0.87 | 2005, 2007 |
| WNT1 | NM_005430 | 625 | wingless-type MMTV integration site family, member 1 | hsa-let-7d | −0.07 | 0.88 | 2005, 2007, 2009 |
| GABBR2 | NM_005458 | 626 | gamma-aminobutyric acid (GABA) B receptor, 2 | hsa-miR-4458 | −0.07 | 0.89 | 2009 |
| MED6 | NM_005466 | 627 | mediator complex subunit 6 | hsa-let-7d | −0.14 | 0.86 | 2005, 2007, 2009 |
| SH2B3 | NM_005475 | 628 | SH2B adaptor protein 3 | hsa-miR-4500 | −0.13 | 0.94 | 2007, 2009 |
| INPP5A | NM_005539 | 629 | inositol polyphosphate-5-phosphatase, 40 kDa | hsa-let-7d | −0.1 | 0.92 | 2005, 2007, 2009 |
| ISLR | NM_005545 | 630 | immunoglobulin superfamily containing leucine-rich repeat | hsa-let-7b | −0.23 | 0.86 | |
| LIMK2 | NM_005569 | 631 | LIM domain kinase 2 | hsa-miR-98 | −0.14 | 0.76 | |
| MDFI | NM_005586 | 632 | MyoD family inhibitor | hsa-miR-4500 | −0.11 | 0.94 | 2007, 2009 |
| ZNF354A | NM_005649 | 633 | zinc finger protein 354A | hsa-miR-4500 | −0.27 | 0.93 | 2005, 2007, 2009 |
| SOX13 | NM_005686 | 634 | SRY (sex determining region Y)-box 13 | hsa-let-7g | −0.16 | 0.9 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| ABCC5 | NM_005688 | 635 | ATP-binding cassette, sub-family C (CFTR/MRP), member 5 | hsa-miR-4500 | −0.34 | 0.67 | 2005, 2007, 2009 |
| DPP3 | NM_005700 | 636 | dipeptidyl-peptidase 3 | hsa-miR-4458 | −0.35 | 0.91 | 2005, 2007, 2009 |
| GIPC1 | NM_005716 | 637 | GIPC PDZ domain containing family, member 1 | hsa-miR-4458 | −0.26 | 0.9 | 2007, 2009 |
| TSPAN2 | NM_005725 | 638 | tetraspanin 2 | hsa-let-7g | −0.09 | 0.94 | 2009 |
| PLXNC1 | NM_005761 | 639 | plexin C1 | hsa-miR-4458 | −0.33 | 0.33 | |
| AASS | NM_005763 | 640 | aminoadipate-semialdehyde synthase | hsa-miR-4458 | −0.16 | <0.1 | |
| FARP1 | NM_005766 | 641 | FERM, RhoGEF (ARHGEF) and pleckstrin domain protein 1 (chondrocyte-derived) | hsa-miR-4500 | −0.16 | 0.93 | 2005, 2007, 2009 |
| NME6 | NM_005793 | 642 | non-metastatic cells 6, protein expressed in (nucleoside-diphosphate kinase) | hsa-miR-4458 | −0.27 | 0.94 | 2005, 2007, 2009 |
| SPEG | NM_005876 | 643 | SPEG complex locus | hsa-let-7d | −0.11 | 0.9 | 2009 |
| DNAJA2 | NM_005880 | 644 | DnaJ (Hsp40) homolog, subfamily A, member 2 | hsa-miR-4458 | −0.28 | 0.79 | |
| APC2 | NM_005883 | 645 | adenomatosis polyposis coli 2 | hsa-miR-4458 | −0.11 | 0.83 | 2009 |
| MEF2D | NM_005920 | 646 | myocyte enhancer factor 2D | hsa-miR-4458 | >−0.04 | 0.94 | 2005, 2007, 2009 |
| MAP3K1 | NM_005921 | 647 | mitogen-activated protein kinase kinase kinase 1 | hsa-miR-4458 | −0.39 | 0.86 | 2009 |
| MMP11 | NM_005940 | 648 | matrix metallopeptidase 11 (stromelysin 3) | hsa-let-7d | −0.12 | 0.92 | 2007, 2009 |
| ALKBH1 | NM_006020 | 649 | alkB, alkylation repair homolog 1 (E. coli) | hsa-miR-4500 | −0.16 | 0.89 | 2009 |
| APBB3 | NM_006051 | 650 | amyloid beta (A4) precursor protein-binding, family B, member 3 | hsa-let-7a | −0.41 | 0.98 | 2005, 2007, 2009 |
| DAGLA | NM_006133 | 651 | diacylglycerol lipase, alpha | hsa-miR-4458 | −0.27 | 0.97 | 2007, 2009 |
| PRKAA2 | NM_006252 | 652 | protein kinase, AMP-activated, alpha 2 catalytic subunit | hsa-let-7f | −0.17 | 0.93 | 2009 |
| RANBP2 | NM_006267 | 653 | RAN binding protein 2 | hsa-miR-4458 | −0.38 | 0.98 | 2005, 2007, 2009 |
| DPF2 | NM_006268 | 654 | D4, zinc and double PHD fingers family 2 | hsa-let-7g | −0.21 | 0.94 | 2005, 2007, 2009 |
| CCL7 | NM_006273 | 655 | chemokine (C-C motif) ligand 7 | hsa-miR-4458 | −0.39 | 0.9 | 2009 |
| TNFAIP3 | NM_006290 | 656 | tumor necrosis factor, alpha-induced protein 3 | hsa-miR-4458 | −0.08 | 0.92 | 2009 |
| SMC1A | NM_006306 | 657 | structural maintenance of chromosomes 1A | hsa-let-7a | −0.46 | >0.99 | 2009 |
| PCGF3 | NM_006315 | 658 | polycomb group ring finger 3 | hsa-let-7a | −0.11 | 0.98 | 2005, 2007, 2009 |
| CRTAP | NM_006371 | 659 | cartilage associated protein | hsa-miR-4500 | −0.11 | 0.94 | 2005, 2007, 2009 |
| APPBP2 | NM_006380 | 660 | amyloid beta precursor protein (cytoplasmic tail) binding protein 2 | hsa-miR-4458 | −0.02 | 0.92 | 2005, 2007 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| OLFM4 | NM_006418 | 661 | olfactomedin 4 | hsa-miR-4500 | −0.37 | <0.1 | |
| ARID3B | NM_006465 | 662 | AT rich interactive domain 3B (BRIGHT-like) | hsa-let-7i | −0.72 | >0.99 | 2005, 2007, 2009 |
| IGF2BP3 | NM_006547 | 663 | insulin-like growth factor 2 mRNA binding protein 3 | hsa-let-7a | −0.33 | 0.96 | 2007, 2009 |
| CLDN16 | NM_006580 | 664 | claudin 16 | hsa-miR-98 | −0.3 | <0.1 | |
| MAP3K2 | NM_006609 | 665 | mitogen-activated protein kinase kinase kinase 2 | hsa-let-7a | −0.1 | 0.8 | |
| ARPP19 | NM_006628 | 666 | cAMP-regulated phosphoprotein, 19 kDa | hsa-miR-98 | −0.09 | 0.98 | 2005, 2007, 2009 |
| PGRMC1 | NM_006667 | 667 | progesterone receptor membrane component 1 | hsa-miR-4458 | −0.46 | 0.98 | 2005, 2007, 2009 |
| CYP46A1 | NM_006668 | 668 | cytochrome P450, family 46, subfamily A, polypeptide 1 | hsa-let-7a | −0.17 | 0.89 | 2007, 2009 |
| SUB1 | NM_006713 | 669 | SUB1 homolog (*S. cerevisiae*) | hsa-miR-4500 | −0.36 | 0.84 | |
| BTG2 | NM_006763 | 670 | BTG family, member 2 | hsa-miR-4458 | −0.12 | 0.89 | 2005, 2007, 2009 |
| PKIA | NM_006823 | 671 | protein kinase (cAMP-dependent, catalytic) inhibitor alpha | hsa-miR-4458 | −0.18 | 0.94 | |
| B3GNT1 | NM_006876 | 672 | UDP-GlcNAc:betaGal beta-1,3-N-acetylglucosaminyltransferase 1 | hsa-miR-4500 | −0.34 | 0.93 | 2007, 2009 |
| CALM1 | NM_006888 | 673 | calmodulin 1 (phosphorylase kinase, delta) | hsa-miR-4500 | −0.1 | 0.93 | 2005, 2007, 2009 |
| PRRX1 | NM_006902 | 674 | paired related homeobox 1 | hsa-miR-98 | −0.05 | 0.95 | 2007, 2009 |
| RNF5 | NM_006913 | 675 | ring finger protein 5 | hsa-miR-4458 | −0.26 | 0.64 | 2005, 2007, 2009 |
| ZNF24 | NM_006965 | 676 | zinc finger protein 24 | hsa-miR-4500 | −0.12 | 0.94 | |
| ADAMTS1 | NM_006988 | 677 | ADAM metallopeptidase with thrombospondin type 1 motif, 1 | hsa-miR-98 | −0.12 | 0.84 | 2009 |
| ZNF197 | NM_006991 | 678 | zinc finger protein 197 | hsa-let-7a | −0.38 | 0.12 | |
| SLC35D2 | NM_007001 | 679 | solute carrier family 35, member D2 | hsa-let-7d | −0.48 | 0.98 | 2005, 2007, 2009 |
| CNTRL | NM_007018 | 680 | centriolin | hsa-miR-4458 | −0.42 | 0.98 | 2009 |
| ADAMTS8 | NM_007037 | 681 | ADAM metallopeptidase with thrombospondin type 1 motif, 8 | hsa-miR-4500 | −0.4 | 0.98 | 2007, 2009 |
| ADAMTS5 | NM_007038 | 682 | ADAM metallopeptidase with thrombospondin type 1 motif, 5 | hsa-miR-4458 | −0.18 | 0.95 | 2005, 2007, 2009 |
| UTRN | NM_007124 | 683 | utrophin | hsa-miR-4458 | −0.35 | 0.9 | 2007, 2009 |
| ZNF81 | NM_007137 | 684 | zinc finger protein 81 | hsa-miR-4500 | −0.07 | 0.81 | |
| TUSC2 | NM_007275 | 685 | tumor suppressor candidate 2 | hsa-miR-4458 | −0.12 | 0.93 | 2005, 2007, 2009 |
| AP4E1 | NM_007347 | 686 | adaptor-related protein complex 4, epsilon 1 subunit | hsa-miR-4458 | >−0.02 | 0.57 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| NID2 | NM_007361 | 687 | nidogen 2 (osteonidogen) | hsa-miR-4500 | −0.16 | 0.92 | 2005, 2007, 2009 |
| BRD3 | NM_007371 | 688 | bromodomain containing 3 | hsa-miR-4500 | −0.11 | 0.94 | 2005, 2007, 2009 |
| ICOS | NM_012092 | 689 | inducible T-cell co-stimulator | hsa-let-7b | −0.24 | 0.92 | 2009 |
| ANGPTL2 | NM_012098 | 690 | angiopoietin-like 2 | hsa-miR-4458 | −0.13 | 0.93 | 2005, 2007, 2009 |
| BACE2 | NM_012105 | 691 | beta-site APP-cleaving enzyme 2 | hsa-miR-4500 | −0.27 | 0.93 | 2009 |
| FZD4 | NM_012193 | 692 | frizzled family receptor 4 | hsa-miR-4500 | −0.33 | 0.94 | 2007, 2009 |
| EIF2C1 | NM_012199 | 693 | eukaryotic translation initiation factor 2C, 1 | hsa-miR-4500 | −0.16 | 0.93 | 2005, 2007, 2009 |
| B3GAT3 | NM_012200 | 694 | beta-1,3-glucuronyltransferase 3 (glucuronosyltransferase I) | hsa-miR-4458 | −0.18 | 0.88 | 2009 |
| MGAT4A | NM_012214 | 695 | mannosyl (alpha-1,3-)-glycoprotein beta-1,4-N-acetylgluco saminyltransferase, isozyme A | hsa-miR-4500 | −0.29 | 0.95 | 2005, 2007, 2009 |
| HS2ST1 | NM_012262 | 696 | heparan sulfate 2-O-sulfotransferase 1 | hsa-miR-98 | −0.06 | 0.89 | 2009 |
| ESPL1 | NM_012291 | 697 | extra spindle pole bodies homolog 1 (S. cerevisiae) | hsa-miR-98 | −0.28 | 0.57 | |
| PXDN | NM_012293 | 698 | peroxidasin homolog (Drosophila) | hsa-miR-4500 | −0.12 | >0.99 | 2007, 2009 |
| GAB2 | NM_012296 | 699 | GRB2-associated binding protein 2 | hsa-miR-4458 | −0.15 | 0.6 | 2009 |
| PLA2G15 | NM_012320 | 700 | phospholipase A2, group XV | hsa-miR-4458 | −0.09 | 0.92 | 2005, 2007, 2009 |
| DNAJB9 | NM_012328 | 701 | DnaJ (Hsp40) homolog, subfamily B, member 9 | hsa-miR-4500 | −0.1 | 0.91 | 2005, 2007, 2009 |
| MYCBP | NM_012333 | 702 | c-myc binding protein | hsa-miR-4458 | −0.08 | 0.98 | 2009 |
| MYO1F | NM_012335 | 703 | myosin IF | hsa-miR-4500 | −0.22 | 0.93 | 2007, 2009 |
| NNT | NM_012343 | 704 | nicotinamide nucleotide transhydrogenase | hsa-miR-4458 | −0.26 | 0.87 | 2009 |
| PLDN | NM_012388 | 705 | pallidin homolog (mouse) | hsa-miR-4500 | −0.07 | 0.94 | 2005, 2007, 2009 |
| CDK14 | NM_012395 | 706 | cyclin-dependent kinase 14 | hsa-miR-4500 | −0.16 | 0.67 | |
| ICMT | NM_012405 | 707 | isoprenylcysteine carboxyl methyltransferase | hsa-miR-4458 | >−0.03 | 0.98 | 2009 |
| RAB3GAP2 | NM_012414 | 708 | RAB3 GTPase activating protein subunit 2 (non-catalytic) | hsa-let-7d | −0.18 | 0.94 | |
| PPARGC1A | NM_013261 | 709 | peroxisome proliferator-activated receptor gamma, coactivator 1 alpha | hsa-miR-4500 | −0.11 | 0.83 | 2005, 2007, 2009 |
| EEF2K | NM_013302 | 710 | eukaryotic elongation factor-2 kinase | hsa-let-7d | −0.17 | 0.95 | 2007, 2009 |
| SLC30A4 | NM_013309 | 711 | solute carrier family 30 (zinc transporter), member 4 | hsa-let-7a | −0.14 | 0.94 | 2005, 2007, 2009 |
| HCFC2 | NM_013320 | 712 | host cell factor C2 | hsa-miR-4500 | −0.04 | 0.91 | |
| ATG4B | NM_013325 | 713 | ATG4 autophagy related 4 homolog B (S. cerevisiae) | hsa-let-7a | −0.19 | 0.79 | 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| GPR132 | NM_013345 | 714 | G protein-coupled receptor 132 | hsa-let-7f | −0.21 | <0.1 | |
| TRHDE | NM_013381 | 715 | thyrotropin-releasing hormone degrading enzyme | hsa-let-7d | −0.19 | 0.99 | 2005, 2007, 2009 |
| SLC25A24 | NM_013386 | 716 | solute carrier family 25 (mitochondrial carrier; phosphate carrier), member 24 | hsa-miR-4458 | −0.24 | 0.94 | 2005, 2007, 2009 |
| WDR37 | NM_014023 | 717 | WD repeat domain 37 | hsa-let-7a | −0.21 | 0.99 | 2005, 2007, 2009 |
| PSORS1C2 | NM_014069 | 718 | psoriasis susceptibility 1 candidate 2 | hsa-let-7d | −0.15 | 0.93 | |
| SCN11A | NM_014139 | 719 | sodium channel, voltage-gated, type XI, alpha subunit | hsa-miR-4458 | −0.36 | 0.91 | 2007, 2009 |
| HOXC11 | NM_014212 | 720 | homeobox C11 | hsa-miR-4458 | −0.08 | 0.94 | 2005, 2007, 2009 |
| LIMD1 | NM_014240 | 721 | LIM domains containing 1 | hsa-let-7b | −0.05 | 0.92 | 2005, 2007, 2009 |
| HABP4 | NM_014282 | 722 | hyaluronan binding protein 4 | hsa-miR-4458 | −0.18 | 0.94 | 2009 |
| TGDS | NM_014305 | 723 | TDP-glucose 4,6-dehydratase | hsa-miR-4500 | −0.24 | 0.95 | 2009 |
| SMUG1 | NM_014311 | 724 | single-strand-selective monofunctional uracil-DNA glycosylase 1 | hsa-let-7d | −0.35 | 0.92 | 2009 |
| CACNG4 | NM_014405 | 725 | calcium channel, voltage-dependent, gamma subunit 4 | hsa-miR-4458 | −0.17 | 0.84 | 2005, 2007, 2009 |
| KIAA1274 | NM_014431 | 726 | KIAA1274 | hsa-miR-98 | −0.38 | 0.98 | 2009 |
| ZKSCAN5 | NM_014569 | 727 | zinc finger with KRAB and SCAN domains 5 | hsa-miR-4458 | −0.1 | 0.77 | |
| ERO1L | NM_014584 | 728 | ERO1-like (S. cerevisiae) | hsa-miR-4500 | −0.18 | 0.88 | 2009 |
| SOCS7 | NM_014598 | 729 | suppressor of cytokine signaling 7 | hsa-miR-4458 | >−0.02 | 0.92 | |
| UBXN4 | NM_014607 | 730 | UBX domain protein 4 | hsa-let-7a | −0.15 | 0.89 | 2005, 2007, 2009 |
| RALGPS1 | NM_014636 | 731 | Ral GEF with PH domain and SH3 binding motif 1 | hsa-miR-4500 | −0.15 | 0.94 | 2005, 2007, 2009 |
| TTLL4 | NM_014640 | 732 | tubulin tyrosine ligase-like family, member 4 | hsa-let-7d | −0.56 | >0.99 | 2003, 2005, 2007, 2009 |
| ZNF516 | NM_014643 | 733 | zinc finger protein 516 | hsa-miR-4500 | −0.04 | 0.95 | 2009 |
| GREB1 | NM_014668 | 734 | growth regulation by estrogen in breast cancer 1 | hsa-miR-4500 | −0.17 | 0.88 | 2009 |
| ULK2 | NM_014683 | 735 | unc-51-like kinase 2 (C. elegans) | hsa-miR-98 | −0.14 | 0.95 | 2005, 2007, 2009 |
| SEC14L5 | NM_014692 | 736 | SEC14-like 5 (S. cerevisiae) | hsa-let-7d | −0.14 | 0.98 | 2009 |
| TBKBP1 | NM_014726 | 737 | TBK1 binding protein 1 | hsa-miR-4500 | −0.36 | 0.97 | 2007, 2009 |
| RIMS3 | NM_014747 | 738 | regulating synaptic membrane exocytosis 3 | hsa-miR-4458 | >−0.01 | 0.92 | 2009 |
| TSC22D2 | NM_014779 | 739 | TSC22 domain family, member 2 | hsa-miR-4458 | −0.16 | 0.87 | 2005, 2007, 2009 |
| LRIG2 | NM_014813 | 740 | leucine-rich repeats and immunoglobulin-like domains 2 | hsa-let-7d | −0.48 | 0.95 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| ZBTB39 | NM_014830 | 741 | zinc finger and BTB domain containing 39 | hsa-miR-4458 | −0.04 | 0.98 | 2007, 2009 |
| TRANK1 | NM_014831 | 742 | tetratricopeptide repeat and ankyrin repeat containing 1 | hsa-let-7b | −0.3 | 0.85 | 2009 |
| TECPR2 | NM_014844 | 743 | tectonin beta-propeller repeat containing 2 | hsa-let-7d | −0.13 | 0.94 | 2005, 2007, 2009 |
| ZBTB5 | NM_014872 | 744 | zinc finger and BTB domain containing 5 | hsa-let-7f | −0.23 | 0.92 | 2005, 2007, 2009 |
| LPGAT1 | NM_014873 | 745 | lysophosphatidylglycerol acyltransferase 1 | hsa-let-7g | −0.34 | >0.99 | 2005, 2007, 2009 |
| HELZ | NM_014877 | 746 | helicase with zinc finger | hsa-let-7d | −0.28 | 0.9 | |
| RNF44 | NM_014901 | 747 | ring finger protein 44 | hsa-let-7i | −0.14 | 0.94 | 2005, 2007, 2009 |
| AAK1 | NM_014911 | 748 | AP2 associated kinase 1 | hsa-miR-4458 | >−0.03 | 0.92 | 2007, 2009 |
| DZIP1 | NM_014934 | 749 | DAZ interacting protein 1 | hsa-miR-4500 | −0.11 | 0.94 | 2005, 2007, 2009 |
| MLXIP | NM_014938 | 750 | MLX interacting protein | hsa-miR-4458 | −0.11 | 0.8 | |
| BAHD1 | NM_014952 | 751 | bromo adjacent homology domain containing 1 | hsa-miR-4458 | −0.05 | 0.89 | 2005, 2007, 2009 |
| CEP164 | NM_014956 | 752 | centrosomal protein 164 kDa | hsa-miR-4458 | −0.08 | 0.93 | 2005, 2007, 2009 |
| RUFY3 | NM_014961 | 753 | RUN and FYVE domain containing 3 | hsa-let-7f | −0.13 | 0.93 | 2007, 2009 |
| BTBD3 | NM_014962 | 754 | BTB (POZ) domain containing 3 | hsa-let-7c | −0.19 | 0.92 | 2005, 2007, 2009 |
| MON2 | NM_015026 | 755 | MON2 homolog (S. cerevisiae) | hsa-miR-4458 | −0.09 | 0.94 | 2007, 2009 |
| NMNAT2 | NM_015039 | 756 | nicotinamide nucleotide adenylyltransferase 2 | hsa-miR-4458 | >−0.01 | 0.72 | |
| RRP1B | NM_015056 | 757 | ribosomal RNA processing 1 homolog B (S. cerevisiae) | hsa-miR-4458 | −0.09 | 0.93 | 2007, 2009 |
| SLC8A2 | NM_015063 | 758 | solute carrier family 8 (sodium/calcium exchanger), member 2 | hsa-miR-4458 | −0.07 | 0.91 | 2005, 2007, 2009 |
| DDN | NM_015086 | 759 | dendrin | hsa-miR-4500 | −0.18 | 0.92 | 2009 |
| TAB2 | NM_015093 | 760 | TGF-beta activated kinase 1/MAP3K7 binding protein 2 | hsa-miR-4500 | −0.16 | 0.83 | 2005, 2007, 2009 |
| HIC2 | NM_015094 | 761 | hypermethylated in cancer 2 | hsa-miR-4458 | −0.45 | >0.99 | 2003, 2005, 2007, 2009 |
| PLXND1 | NM_015103 | 762 | plexin D1 | hsa-miR-4500 | −0.35 | 0.98 | 2007, 2009 |
| ZC3H3 | NM_015117 | 763 | zinc finger CCCH-type containing 3 | hsa-let-7d | −0.3 | 0.98 | 2007, 2009 |
| FRMD4B | NM_015123 | 764 | FERM domain containing 4B | hsa-miR-4500 | −0.31 | 0.86 | 2009 |
| DTX4 | NM_015177 | 765 | deltex homolog 4 (Drosophila) | hsa-miR-4500 | −0.06 | 0.98 | 2009 |
| OTUD3 | NM_015207 | 766 | OTU domain containing 3 | hsa-miR-4458 | >−0.01 | 0.82 | 2009 |
| KHNYN | NM_015299 | 767 | KH and NYN domain containing | hsa-let-7f | −0.44 | 0.93 | |
| USP24 | NM_015306 | 768 | ubiquitin specific peptidase 24 | hsa-miR-4458 | −0.26 | 0.93 | 2009 |
| FAM189A1 | NM_015307 | 769 | family with sequence similarity 189, member A1 | hsa-miR-4458 | −0.19 | 0.94 | 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| LEPROTL1 | NM_015344 | 770 | leptin receptor overlapping transcript-like 1 | hsa-let-7d | −0.09 | 0.82 | 2005, 2007 |
| ZFYVE26 | NM_015346 | 771 | zinc finger, FYVE domain containing 26 | hsa-miR-4458 | −0.38 | 0.98 | 2005, 2007, 2009 |
| PARM1 | NM_015393 | 772 | prostate androgen-regulated mucin-like protein 1 | hsa-miR-4458 | −0.24 | 0.97 | 2009 |
| ARMC8 | NM_015396 | 773 | armadillo repeat containing 8 | hsa-miR-4500 | −0.1 | 0.87 | |
| AHCTF1 | NM_015446 | 774 | AT hook containing transcription factor 1 | hsa-miR-4458 | −0.38 | 0.4 | 2007, 2009 |
| MYRIP | NM_015460 | 775 | myosin VIIA and Rab interacting protein | hsa-miR-4458 | −0.11 | 0.85 | 2005, 2007, 2009 |
| SLC22A23 | NM_015482 | 776 | solute carrier family 22, member 23 | hsa-miR-4458 | −0.27 | 0.98 | |
| PNKD | NM_015488 | 777 | paroxysmal nonkinesigenic dyskinesia | hsa-miR-4458 | −0.14 | 0.76 | 2007, 2009 |
| SEC31B | NM_015490 | 778 | SEC31 homolog B (*S. cerevisiae*) | hsa-miR-4458 | −0.15 | 0.82 | 2009 |
| C15orf39 | NM_015492 | 779 | chromosome 15 open reading frame 39 | hsa-let-7a | −0.31 | 0.93 | 2009 |
| LRIG1 | NM_015541 | 780 | leucine-rich repeats and immunoglobulin-like domains 1 | hsa-miR-4458 | N/A | 0.95 | 2005, 2007, 2009 |
| OSBPL3 | NM_015550 | 781 | oxysterol binding protein-like 3 | hsa-miR-4458 | −0.2 | 0.95 | 2005, 2007, 2009 |
| LTN1 | NM_015565 | 782 | listerin E3 ubiquitin protein ligase 1 | hsa-let-7d | −0.22 | 0.93 | 2005, 2007, 2009 |
| PLA2G3 | NM_015715 | 783 | phospholipase A2, group III | hsa-let-7a | −0.35 | 0.91 | 2009 |
| DCAF8 | NM_015726 | 784 | DDB1 and CUL4 associated factor 8 | hsa-miR-4500 | −0.1 | 0.66 | |
| WARS2 | NM_015836 | 785 | tryptophanyl tRNA synthetase 2, mitochondrial | hsa-miR-4458 | −0.3 | <0.1 | 2009 |
| MBTPS2 | NM_015884 | 786 | membrane-bound transcription factor peptidase, site 2 | hsa-miR-4458 | −0.06 | 0.86 | |
| HOOK1 | NM_015888 | 787 | hook homolog 1 (*Drosophila*) | hsa-miR-4458 | −0.12 | 0.94 | 2007, 2009 |
| TAF9B | NM_015975 | 788 | TAF9B RNA polymerase II, TATA box binding protein (TBP)-associated factor, 31 kDa | hsa-let-7a | −0.3 | 0.98 | 2009 |
| GOLT1B | NM_016072 | 789 | golgi transport 1B | hsa-miR-4500 | −0.18 | 0.98 | 2005, 2007, 2009 |
| CERCAM | NM_016174 | 790 | cerebral endothelial cell adhesion molecule | hsa-let-7d | −0.15 | 0.93 | 2007, 2009 |
| VGLL3 | NM_016206 | 791 | vestigial like 3 (*Drosophila*) | hsa-miR-4458 | −0.11 | 0.94 | 2009 |
| NLK | NM_016231 | 792 | nemo-like kinase | hsa-miR-4500 | −0.14 | 0.87 | 2005, 2007, 2009 |
| SCARA3 | NM_016240 | 793 | scavenger receptor class A, member 3 | hsa-miR-4500 | −0.03 | 0.77 | |
| IMPG2 | NM_016247 | 794 | interphotoreceptor matrix proteoglycan 2 | hsa-let-7i | −0.31 | 0.95 | |
| TOB2 | NM_016272 | 795 | transducer of ERBB2, 2 | hsa-miR-4458 | >−0.02 | 0.94 | 2005, 2007, 2009 |
| PLEKHO1 | NM_016274 | 796 | pleckstrin homology domain containing, family O member 1 | hsa-miR-4458 | −0.2 | 0.79 | 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| ANKFY1 | NM_016376 | 797 | ankyrin repeat and FYVE domain containing 1 | hsa-miR-4458 | >−0.03 | 0.98 | 2005, 2007, 2009 |
| LUC7L3 | NM_016424 | 798 | LUC7-like 3 (S. cerevisiae) | hsa-miR-4500 | −0.05 | 0.85 | 2005, 2007, 2009 |
| RAB8B | NM_016530 | 799 | RAB8B, member RAS oncogene family | hsa-let-7f | −0.07 | 0.92 | 2007 |
| GCNT4 | NM_016591 | 800 | glucosaminyl (N-acetyl) transferase 4, core 2 | hsa-miR-4500 | −0.34 | 0.91 | 2007, 2009 |
| UFM1 | NM_016617 | 801 | ubiquitin-fold modifier 1 | hsa-miR-4458 | −0.36 | 0.63 | 2009 |
| ZNF644 | NM_016620 | 802 | zinc finger protein 644 | hsa-miR-4458 | −0.28 | 0.97 | 2005, 2007, 2009 |
| FZD3 | NM_017412 | 803 | frizzled family receptor 3 | hsa-miR-98 | −0.2 | >0.99 | |
| RBM38 | NM_017495 | 804 | RNA binding motif protein 38 | hsa-miR-4458 | −0.25 | 0.98 | 2007, 2009 |
| STAB2 | NM_017564 | 805 | stabilin 2 | hsa-miR-4500 | −0.13 | 0.9 | 2005, 2007, 2009 |
| KIF21B | NM_017596 | 806 | kinesin family member 21B | hsa-miR-4458 | >−0.03 | 0.95 | 2007, 2009 |
| EIF2C4 | NM_017629 | 807 | eukaryotic translation initiation factor 2C, 4 | hsa-let-7d | −0.17 | 0.95 | 2005, 2007, 2009 |
| BNC2 | NM_017637 | 808 | basonuclin 2 | hsa-let-7g | −0.03 | 0.88 | 2005, 2007, 2009 |
| KLHL24 | NM_017644 | 809 | kelch-like 24 (Drosophila) | hsa-miR-4458 | >−0.01 | 0.87 | 2007, 2009 |
| GDAP2 | NM_017686 | 810 | ganglioside induced differentiation associated protein 2 | hsa-let-7d | −0.33 | 0.97 | 2009 |
| FBXL12 | NM_017703 | 811 | F-box and leucine-rich repeat protein 12 | hsa-miR-4458 | −0.32 | 0.92 | 2007, 2009 |
| ANKRD49 | NM_017704 | 812 | ankyrin repeat domain 49 | hsa-miR-4500 | −0.25 | 0.9 | 2007, 2009 |
| UHRF1BP1 | NM_017754 | 813 | UHRF1 binding protein 1 | hsa-miR-4500 | −0.03 | 0.85 | |
| INO80D | NM_017759 | 814 | INO80 complex subunit D | hsa-miR-4500 | −0.12 | 0.91 | 2005, 2007, 2009 |
| CHD7 | NM_017780 | 815 | chromodomain helicase DNA binding protein 7 | hsa-miR-4500 | −0.07 | 0.86 | 2005, 2007, 2009 |
| SEMA4C | NM_017789 | 816 | sema domain, immunoglobulin domain (Ig), transmembrane domain (TM) and short cytoplasmic domain, (semaphorin) 4C | hsa-let-7i | −0.32 | 0.98 | 2005, 2007, 2009 |
| CMTM6 | NM_017801 | 817 | CKLF-like MARVEL transmembrane domain containing 6 | hsa-let-7c | −0.16 | <0.1 | |
| HIF1AN | NM_017902 | 818 | hypoxia inducible factor 1, alpha subunit inhibitor | hsa-miR-4500 | −0.47 | 0.94 | 2009 |
| STX17 | NM_017919 | 819 | syntaxin 17 | hsa-miR-4500 | −0.16 | 0.97 | 2005, 2007, 2009 |
| USP47 | NM_017944 | 820 | ubiquitin specific peptidase 47 | hsa-let-7d | −0.14 | 0.94 | 2007, 2009 |
| PDPR | NM_017990 | 821 | pyruvate dehydrogenase phosphatase regulatory subunit | hsa-miR-4500 | −0.3 | 0.95 | 2005, 2007, 2009 |
| C9orf40 | NM_017998 | 822 | chromosome 9 open reading frame 40 | hsa-let-7f | −0.55 | 0.76 | 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| XKR8 | NM_018053 | 823 | XK, Kell blood group complex subunit-related family, member 8 | hsa-miR-4458 | −0.49 | 0.98 | 2007, 2009 |
| PRPF38B | NM_018061 | 824 | PRP38 pre-mRNA processing factor 38 (yeast) domain containing B | hsa-miR-4458 | −0.32 | 0.26 | 2007, 2009 |
| IPO9 | NM_018085 | 825 | importin 9 | hsa-miR-4500 | −0.06 | 0.78 | 2009 |
| FIGN | NM_018086 | 826 | fidgetin | hsa-let-7d | −0.56 | >0.99 | 2007, 2009 |
| CDCA8 | NM_018101 | 827 | cell division cycle associated 8 | hsa-miR-4458 | −0.17 | 0.94 | 2009 |
| FAM178A | NM_018121 | 828 | family with sequence similarity 178, member A | hsa-miR-98 | −0.24 | 0.98 | 2003, 2005, 2007, 2009 |
| LRRC20 | NM_018205 | 829 | leucine rich repeat containing 20 | hsa-miR-4458 | −0.04 | 0.87 | 2009 |
| ETNK2 | NM_018208 | 830 | ethanolamine kinase 2 | hsa-miR-4458 | −0.14 | 0.93 | 2005, 2007, 2009 |
| TMEM143 | NM_018273 | 831 | transmembrane protein 143 | hsa-miR-4500 | −0.23 | 0.9 | 2009 |
| BRF2 | NM_018310 | 832 | BRF2, subunit of RNA polymerase III transcription initiation factor, BRF1-like | hsa-miR-4500 | −0.43 | <0.1 | 2009 |
| DDX19A | NM_018332 | 833 | DEAD (Asp-Glu-Ala-As) box polypeptide 19A | hsa-miR-4500 | −0.47 | 0.94 | 2007, 2009 |
| FGD6 | NM_018351 | 834 | FYVE, RhoGEF and PH domain containing 6 | hsa-miR-4458 | −0.32 | 0.99 | 2009 |
| ACER3 | NM_018367 | 835 | alkaline ceramidase 3 | hsa-let-7d | −0.2 | 0.93 | |
| SYNJ2BP | NM_018373 | 836 | synaptojanin 2 binding protein | hsa-miR-4500 | −0.11 | 0.85 | |
| PAG1 | NM_018440 | 837 | phosphoprotein associated with glycosphingolipid microdomains 1 | hsa-miR-4458 | −0.3 | 0.98 | 2009 |
| ACTR10 | NM_018477 | 838 | actin-related protein 10 homolog (S. cerevisiae) | hsa-let-7f | −0.34 | 0.75 | 2009 |
| LGR4 | NM_018490 | 839 | leucine-rich repeat containing G protein-coupled receptor 4 | hsa-miR-4500 | −0.2 | 0.92 | 2005, 2007, 2009 |
| YOD1 | NM_018566 | 840 | YOD1 OTU deubiquinating enzyme 1 homolog (S. cerevisiae) | hsa-miR-4500 | −0.57 | >0.99 | 2007, 2009 |
| SLC16A10 | NM_018593 | 841 | solute carrier family 16, member 10 (aromatic amino acid transporter) | hsa-miR-4500 | −0.14 | 0.86 | 2009 |
| ETNK1 | NM_018638 | 842 | ethanolamine kinase 1 | hsa-miR-4500 | −0.05 | 0.92 | 2007, 2009 |
| B3GAT1 | NM_018644 | 843 | beta-1,3-glucuronyltransferase 1 (glucuronosyltransferase P) | hsa-let-7d | −0.02 | 0.9 | 2009 |
| BIN3 | NM_018688 | 844 | bridging integrator 3 | hsa-let-7g | −0.22 | 0.92 | 2005, 2007, 2009 |
| YIPF1 | NM_018982 | 845 | Yip1 domain family, member 1 | hsa-let-7d | −0.18 | 0.71 | |
| SSH1 | NM_018984 | 846 | slingshot homolog 1 (Drosophila) | hsa-let-7a | −0.17 | 0.95 | 2005, 2007, 2009 |
| SMCR7L | NM_019008 | 847 | Smith-Magenis syndrome chromosome region, candidate 7-like | hsa-let-7f | −0.08 | 0.94 | 2007, 2009 |
| CCDC93 | NM_019044 | 848 | coiled-coil domain containing 93 | hsa-miR-4458 | −0.07 | 0.62 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| CRCT1 | NM_019060 | 849 | cysteine-rich C-terminal 1 | hsa-miR-4500 | −0.28 | 0.92 | 2009 |
| CCDC76 | NM_019083 | 850 | coiled-coil domain containing 76 | hsa-let-7f | −0.38 | 0.72 | |
| UBFD1 | NM_019116 | 851 | ubiquitin family domain containing 1 | hsa-miR-4458 | −0.1 | 0.87 | 2007, 2009 |
| TMEM234 | NM_019118 | 852 | transmembrane protein 234 | hsa-let-7a | −0.37 | 0.92 | 2009 |
| RNF20 | NM_019592 | 853 | ring finger protein 20 | hsa-let-7g | −0.27 | 0.7 | 2005, 2007 |
| GPCPD1 | NM_019593 | 854 | glycerophosphocholine phosphodiesterase GDE1 homolog (*S. cerevisiae*) | hsa-miR-4500 | −0.42 | >0.99 | 2007, 2009 |
| ABCB9 | NM_019624 | 855 | ATP-binding cassette, sub-family B (MDR/TAP), member 9 | hsa-miR-98 | −0.3 | 0.95 | 2005, 2007, 2009 |
| UGGT1 | NM_020120 | 856 | UDP-glucose glycoprotein glucosyltransferase 1 | hsa-miR-4458 | −0.22 | 0.98 | 2007, 2009 |
| KCMF1 | NM_020122 | 857 | potassium channel modulatory factor 1 | hsa-let-7g | −0.02 | 0.93 | 2009 |
| C1GALT1 | NM_020156 | 858 | core 1 synthase, glycoprotein-N-acetylgalactosamine 3-beta-galactosyltransferase, 1 | hsa-miR-98 | −0.07 | 0.98 | |
| SLC12A9 | NM_020246 | 859 | solute carrier family 12 (potassium/chloride transporters), member 9 | hsa-miR-4458 | −0.29 | 0.98 | 2009 |
| MNT | NM_020310 | 860 | MAX binding protein | hsa-let-7d | −0.02 | 0.93 | 2005, 2007, 2009 |
| VANGL2 | NM_020335 | 861 | vang-like 2 (van gogh, *Drosophila*) | hsa-miR-4458 | −0.06 | >0.99 | 2007, 2009 |
| KIAA1244 | NM_020340 | 862 | KIAA1244 | hsa-miR-4458 | >−0.02 | 0.79 | |
| ENTPD7 | NM_020354 | 863 | ectonucleoside triphosphate diphosphohydrolase 7 | hsa-let-7d | −0.17 | 0.94 | |
| AVEN | NM_020371 | 864 | apoptosis, caspase activation inhibitor | hsa-let-7i | −0.22 | 0.59 | |
| SCYL3 | NM_020423 | 865 | SCY1-like 3 (*S. cerevisiae*) | hsa-let-7f | −0.18 | 0.93 | 2005, 2007, 2009 |
| ASPHD2 | NM_020437 | 866 | aspartate beta-hydroxylase domain containing 2 | hsa-miR-4458 | −0.02 | 0.8 | |
| GALNT1 | NM_020474 | 867 | UDP-N-acetyl-alpha-D-galactosamine:polypeptide N-acetylgalactosaminyltransferase 1 (GalNAc-T1) | hsa-miR-4500 | −0.47 | >0.99 | 2005, 2007, 2009 |
| MRS2 | NM_020662 | 868 | MRS2 magnesium homeostasis factor homolog (*S. cerevisiae*) | hsa-let-7f | −0.48 | 0.91 | 2009 |
| RAB22A | NM_020673 | 869 | RAB22A, member RAS oncogene family | hsa-miR-4500 | −0.15 | 0.88 | 2009 |
| ZNF512B | NM_020713 | 870 | zinc finger protein 512B | hsa-miR-4458 | −0.31 | >0.99 | 2007, 2009 |
| PLEKHH1 | NM_020715 | 871 | pleckstrin homology domain containing, family H (with MyTH4 domain) member 1 | hsa-miR-4500 | −0.2 | 0.93 | 2007, 2009 |
| NLN | NM_020726 | 872 | neurolysin (metallopeptidase M3 family) | hsa-miR-4458 | −0.1 | 0.79 | |
| INTS2 | NM_020748 | 873 | integrator complex subunit 2 | hsa-let-7a | −0.3 | 0.84 | 2007, 2009 |
| STARD9 | NM_020759 | 874 | StAR-related lipid transfer (START) domain containing 9 | hsa-miR-4458 | −0.7 | 0.79 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| SRGAP1 | NM_020762 | 875 | SLIT-ROBO Rho GTPase activating protein 1 | hsa-miR-4458 | −0.08 | 0.73 | |
| CASKIN1 | NM_020764 | 876 | CASK interacting protein 1 | hsa-let-7i | −0.1 | 0.89 | 2005, 2007, 2009 |
| KCTD16 | NM_020768 | 877 | potassium channel tetramerisation domain containing 16 | hsa-miR-4458 | −0.19 | 0.87 | 2009 |
| RGAG1 | NM_020769 | 878 | retrotransposon gag domain containing 1 | hsa-let-7f | −0.14 | 0.79 | 2005, 2007 |
| MIB1 | NM_020774 | 879 | mindbomb homolog 1 (Drosophila) | hsa-let-7f | −0.15 | >0.99 | 2007, 2009 |
| ALPK3 | NM_020778 | 880 | alpha-kinase 3 | hsa-miR-4458 | >−0.02 | 0.84 | 2009 |
| PDP2 | NM_020786 | 881 | pyruvate dehyrogenase phosphatase catalytic subunit 2 | hsa-let-7b | −0.18 | 0.92 | 2009 |
| TAOK1 | NM_020791 | 882 | TAO kinase 1 | hsa-let-7g | −0.07 | 0.91 | |
| ARHGAP20 | NM_020809 | 883 | Rho GTPase activating protein 20 | hsa-let-7a | −0.11 | 0.93 | 2005, 2007, 2009 |
| KIAA1467 | NM_020853 | 884 | KIAA1467 | hsa-miR-4458 | −0.15 | 0.83 | 2009 |
| ZSWIM5 | NM_020883 | 885 | zinc finger, SWIM-type containing 5 | hsa-miR-4458 | −0.29 | 0.97 | 2009 |
| PLXNA4 | NM_020911 | 886 | plexin A4 | hsa-miR-4500 | −0.15 | >0.99 | 2009 |
| SLC7A14 | NM_020949 | 887 | solute carrier family 7 (orphan transporter), member 14 | hsa-let-7d | −0.07 | 0.94 | |
| IGDCC4 | NM_020962 | 888 | immunoglobulin superfamily, DCC subclass, member 4 | hsa-let-7a | −0.24 | 0.98 | 2005, 2007, 2009 |
| SPTBN4 | NM_020971 | 889 | spectrin, beta, non-erythrocytic 4 | hsa-miR-4458 | −0.07 | 0.87 | 2007, 2009 |
| XK | NM_021083 | 890 | X-linked Kx blood group (McLeod syndrome) | hsa-miR-4458 | −0.29 | 0.93 | 2009 |
| MTMR3 | NM_021090 | 891 | myotubularin related protein 3 | hsa-let-7a | −0.05 | 0.88 | 2009 |
| SLC5A6 | NM_021095 | 892 | solute carrier family 5 (sodium-dependent vitamin transporter), member 6 | hsa-let-7f | −0.21 | 0.93 | 2007, 2009 |
| COL14A1 | NM_021110 | 893 | collagen, type XIV, alpha 1 | hsa-miR-4500 | −0.3 | 0.71 | 2007 |
| PMAIP1 | NM_021127 | 894 | phorbol-12-myristate-13-acetate-induced protein 1 | hsa-miR-4500 | −0.17 | 0.9 | 2009 |
| FAM108C1 | NM_021214 | 895 | family with sequence similarity 108, member C1 | hsa-miR-98 | −0.2 | 0.72 | |
| RRAGD | NM_021244 | 896 | Ras-related GTP binding D | hsa-miR-4500 | −0.1 | 0.93 | |
| CDH22 | NM_021248 | 897 | cadherin 22, type 2 | hsa-miR-4500 | −0.23 | 0.88 | |
| SNX6 | NM_021249 | 898 | sorting nexin 6 | hsa-let-7c | −0.38 | 0.98 | 2009 |
| SENP2 | NM_021627 | 899 | SUMO1/sentrin/SMT 3 specific peptidase 2 | hsa-miR-4458 | −0.17 | 0.8 | 2005, 2007, 2009 |
| TRIB2 | NM_021643 | 900 | tribbles homolog 2 (Drosophila) | hsa-miR-4458 | −0.11 | 0.84 | 2005, 2007, 2009 |
| SPCS3 | NM_021928 | 901 | signal peptidase complex subunit 3 homolog (S. cerevisiae) | hsa-miR-4458 | −0.06 | 0.81 | |
| FKBP10 | NM_021939 | 902 | FK506 binding protein 10, 65 kDa | hsa-let-7d | −0.08 | 0.65 | |
| TIA1 | NM_022037 | 903 | TIA1 cytotoxic granule-associated RNA binding protein | hsa-let-7f | −0.12 | 0.93 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| GAN | NM_022041 | 904 | gigaxonin | hsa-miR-4500 | −0.26 | 0.98 | 2005, 2007, 2009 |
| CERS2 | NM_022075 | 905 | ceramide synthase 2 | hsa-let-7c | −0.11 | 0.69 | |
| PRSS22 | NM_022119 | 906 | protease, serine, 22 | hsa-miR-98 | −0.2 | 0.84 | |
| SNX16 | NM_022133 | 907 | sorting nexin 16 | hsa-miR-4500 | −0.23 | 0.94 | 2005, 2007, 2009 |
| XYLT1 | NM_022166 | 908 | xylosyltransferase I | hsa-miR-4458 | >−0.03 | 0.99 | 2007, 2009 |
| DNAJC1 | NM_022365 | 909 | DnaJ (Hsp40) homolog, subfamily C, member 1 | hsa-let-7d | −0.21 | 0.85 | 2005, 2007, 2009 |
| NSD1 | NM_022455 | 910 | nuclear receptor binding SET domain protein 1 | hsa-miR-4458 | −0.12 | 0.76 | |
| HIF3A | NM_022462 | 911 | hypoxia inducible factor 3, alpha subunit | hsa-let-7b | −0.35 | >0.99 | 2009 |
| ZMAT3 | NM_022470 | 912 | zinc finger, matrin-type 3 | hsa-miR-4458 | >−0.01 | 0.73 | |
| TTC31 | NM_022492 | 913 | tetratricopeptide repeat domain 31 | hsa-miR-4458 | −0.36 | 0.87 | 2009 |
| MESDC1 | NM_022566 | 914 | mesoderm development candidate 1 | hsa-miR-4500 | −0.15 | 0.8 | 2005, 2007, 2009 |
| ELOVL4 | NM_022726 | 915 | ELOVL fatty acid elongase 4 | hsa-miR-4500 | −0.16 | 0.94 | 2005, 2007, 2009 |
| FAM160B2 | NM_022749 | 916 | family with sequence similarity 160, member B2 | hsa-miR-4458 | −0.06 | 0.92 | 2005, 2007, 2009 |
| AEN | NM_022767 | 917 | apoptosis enhancing nuclease | hsa-miR-4458 | −0.31 | 0.93 | 2009 |
| RNF38 | NM_022781 | 918 | ring finger protein 38 | hsa-let-7g | −0.13 | 0.7 | 2005, 2007, 2009 |
| ANKRA2 | NM_023039 | 919 | ankyrin repeat, family A (RFXANK-like), 2 | hsa-miR-4458 | −0.19 | 0.84 | |
| ZSWIM4 | NM_023072 | 920 | zinc finger, SWIM-type containing 4 | hsa-miR-4458 | −0.03 | 0.79 | 2007 |
| OTUB2 | NM_023112 | 921 | OTU domain, ubiquitin aldehyde binding 2 | hsa-miR-4458 | −0.09 | 0.65 | |
| LRFN4 | NM_024036 | 922 | leucine rich repeat and fibronectin type III domain containing 4 | hsa-miR-4458 | −0.12 | 0.89 | 2007, 2009 |
| GNPTAB | NM_024312 | 923 | N-acetylglucosamine-1-phosphate transferase, alpha and beta subunits | hsa-miR-4500 | −0.48 | 0.95 | 2007, 2009 |
| EFHD2 | NM_024329 | 924 | EF-hand domain family, member D2 | hsa-let-7f | −0.19 | 0.97 | 2005, 2007, 2009 |
| HOXD1 | NM_024501 | 925 | homeobox D1 | hsa-miR-4500 | −0.25 | 0.93 | 2005, 2007, 2009 |
| ADIPOR2 | NM_024551 | 926 | adiponectin receptor 2 | hsa-let-7f | −0.16 | 0.94 | 2005, 2007, 2009 |
| CCNJL | NM_024565 | 927 | cyclin J-like | hsa-let-7f | −0.12 | 0.89 | 2009 |
| SRD5A3 | NM_024592 | 928 | steroid 5 alpha-reductase 3 | hsa-let-7a | −0.4 | 0.84 | |
| THAP9 | NM_024672 | 929 | THAP domain containing 9 | hsa-miR-4458 | −0.47 | 0.9 | |
| LIN28A | NM_024674 | 930 | lin-28 homolog A (*C. elegans*) | hsa-let-7i | −0.25 | 0.98 | 2005, 2007, 2009 |
| KCTD17 | NM_024681 | 931 | potassium channel tetramerisation domain containing 17 | hsa-miR-4458 | −0.24 | 0.98 | 2007, 2009 |
| C15orf29 | NM_024713 | 932 | chromosome 15 open reading frame 29 | hsa-miR-4458 | −0.18 | 0.94 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication(s) |
|---|---|---|---|---|---|---|---|
| MOBKL2B | NM_024761 | 933 | MOB1, Mps One Binder kinase activator-like 2B (yeast) | hsa-miR-4458 | >−0.03 | 0.93 | 2009 |
| ATP8B4 | NM_024837 | 934 | ATPase, class I, type 8B, member 4 | hsa-let-7a | −0.25 | 0.94 | 2009 |
| EIF2C3 | NM_024852 | 935 | eukaryotic translation initiation factor 2C, 3 | hsa-let-7f | −0.13 | 0.83 | 2005, 2007, 2009 |
| L2HGDH | NM_024884 | 936 | L-2-hydroxyglutarate dehydrogenase | hsa-let-7a | −0.05 | 0.98 | 2009 |
| C7orf58 | NM_024913 | 937 | chromosome 7 open reading frame 58 | hsa-let-7g | −0.14 | 0.92 | 2005, 2007, 2009 |
| PHC3 | NM_024947 | 938 | polyhomeotic homolog 3 (Drosophila) | hsa-let-7b | −0.05 | 0.84 | 2009 |
| CEP135 | NM_025009 | 939 | centrosomal protein 135 kDa | hsa-let-7b | −0.34 | 0.95 | 2009 |
| ARHGEF15 | NM_025014 | 940 | Rho guanine nucleotide exchange factor (GEF) 15 | hsa-miR-4500 | −0.23 | 0.94 | 2005, 2007, 2009 |
| VCPIP1 | NM_025054 | 941 | valosin containing protein (p97)/p47 complex interacting protein 1 | hsa-miR-4458 | >−0.01 | 0.76 | 2005, 2007 |
| FRAS1 | NM_025074 | 942 | Fraser syndrome 1 | hsa-let-7b | −0.42 | 0.95 | 2005, 2007, 2009 |
| NYNRIN | NM_025081 | 943 | NYN domain and retroviral integrase containing | hsa-let-7d | −0.32 | >0.99 | 2007, 2009 |
| CHD9 | NM_025134 | 944 | chromodomain helicase DNA binding protein 9 | hsa-let-7a | −0.07 | 0.74 | 2005, 2007 |
| KIAA1539 | NM_025182 | 945 | KIAA1539 | hsa-miR-4458 | −0.25 | 0.92 | 2005, 2007, 2009 |
| EDEM3 | NM_025191 | 946 | ER degradation enhancer, mannosidase alpha-like 3 | hsa-miR-4500 | −0.21 | 0.98 | 2007, 2009 |
| TRIB1 | NM_025195 | 947 | tribbles homolog 1 (Drosophila) | hsa-miR-4500 | −0.1 | 0.92 | 2005, 2007, 2009 |
| TRABD | NM_025204 | 948 | TraB domain containing | hsa-miR-4458 | −0.22 | 0.73 | 2007, 2009 |
| MED28 | NM_025205 | 949 | mediator complex subunit 28 | hsa-miR-4500 | −0.45 | 0.32 | |
| SOST | NM_025237 | 950 | sclerostin | hsa-miR-4500 | −0.04 | 0.87 | 2009 |
| LIMD2 | NM_030576 | 951 | LIM domain containing 2 | hsa-let-7i | −0.38 | 0.95 | 2007, 2009 |
| CPEB4 | NM_030627 | 952 | cytoplasmic polyadenylation element binding protein 4 | hsa-let-7d | −0.08 | 0.96 | 2005, 2007, 2009 |
| DUSP16 | NM_030640 | 953 | dual specificity phosphatase 16 | hsa-let-7d | −0.19 | 0.97 | 2005, 2007, 2009 |
| C1orf21 | NM_030806 | 954 | chromosome 1 open reading frame 21 | hsa-let-7g | −0.03 | 0.77 | |
| LBH | NM_030915 | 955 | limb bud and heart development homolog (mouse) | hsa-let-7g | −0.07 | 0.92 | 2005, 2007, 2009 |
| FAM103A1 | NM_031452 | 956 | family with sequence similarity 103, member A1 | hsa-miR-4458 | −0.42 | 0.87 | 2009 |
| SLC25A18 | NM_031481 | 957 | solute carrier family 25 (mitochondrial carrier), member 18 | hsa-miR-4458 | −0.34 | 0.94 | 2005, 2007, 2009 |
| KCTD10 | NM_031954 | 958 | potassium channel tetramerisation domain containing 10 | hsa-miR-4458 | >−0.02 | 0.86 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| STARD3NL | NM_032016 | 959 | STARD3 N-terminal like | hsa-miR-4458 | −0.15 | 0.91 | 2005, 2007, 2009 |
| STK40 | NM_032017 | 960 | serine/threonine kinase 40 | hsa-miR-4458 | −0.25 | 0.95 | 2007, 2009 |
| UTP15 | NM_032175 | 961 | UTP15, U3 small nucleolar ribonucleoprotein, homolog (*S. cerevisiae*) | hsa-let-7b | −0.16 | 0.79 | 2009 |
| LOXL4 | NM_032211 | 962 | lysyl oxidase-like 4 | hsa-let-7a | −0.13 | 0.94 | 2005, 2007, 2009 |
| DDI2 | NM_032341 | 963 | DNA-damage inducible 1 homolog 2 (*S. cerevisiae*) | hsa-miR-4500 | −0.46 | 0.98 | 2007, 2009 |
| MEGF11 | NM_032445 | 964 | multiple EGF-like-domains 11 | hsa-miR-4500 | −0.05 | 0.88 | 2009 |
| DOT1L | NM_032482 | 965 | DOT1-like, histone H3 methyltransferase (*S. cerevisiae*) | hsa-miR-4458 | N/A | 0.99 | 2005, 2007, 2009 |
| C6orf168 | NM_032511 | 966 | chromosome 6 open reading frame 168 | hsa-miR-4458 | −0.22 | 0.95 | 2009 |
| PARD6B | NM_032521 | 967 | par-6 partitioning defective 6 homolog beta (*C. elegans*) | hsa-let-7a | −0.29 | 0.95 | 2007, 2009 |
| USP38 | NM_032557 | 968 | ubiquitin specific peptidase 38 | hsa-miR-4500 | −0.33 | 0.85 | 2005, 2007, 2009 |
| USP32 | NM_032582 | 969 | ubiquitin specific peptidase 32 | hsa-let-7a | −0.2 | 0.93 | 2005, 2007, 2009 |
| LOXL3 | NM_032603 | 970 | lysyl oxidase-like 3 | hsa-miR-4458 | −0.1 | 0.79 | 2005, 2007, 2009 |
| FOXP1 | NM_032682 | 971 | forkhead box P1 | hsa-let-7g | −0.04 | 0.85 | 2009 |
| SFT2D3 | NM_032740 | 972 | SFT2 domain containing 3 | hsa-let-7a | −0.34 | <0.1 | 2009 |
| LINGO1 | NM_032808 | 973 | leucine rich repeat and Ig domain containing 1 | hsa-let-7d | −0.3 | 0.89 | 2009 |
| ZNF341 | NM_032819 | 974 | zinc finger protein 341 | hsa-let-7a | −0.42 | <0.1 | |
| PPP1R15B | NM_032833 | 975 | protein phosphatase 1, regulatory (inhibitor) subunit 15B | hsa-let-7c | −0.44 | >0.99 | 2005, 2007, 2009 |
| CGNL1 | NM_032866 | 976 | cingulin-like 1 | hsa-miR-4458 | −0.2 | 0.94 | 2005, 2007, 2009 |
| RAB11FIP4 | NM_032932 | 977 | RAB11 family interacting protein 4 (class II) | hsa-let-7d | −0.27 | >0.99 | 2003, 2005, 2007, 2009 |
| C5orf62 | NM_032947 | 978 | chromosome 5 open reading frame 62 | hsa-let-7d | −0.38 | 0.92 | 2007, 2009 |
| ZCCHC3 | NM_033089 | 979 | zinc finger, CCHC domain containing 3 | hsa-miR-4458 | −0.16 | 0.93 | 2007, 2009 |
| NKD1 | NM_033119 | 980 | naked cuticle homolog 1 (*Drosophila*) | hsa-let-7a | −0.2 | 0.95 | 2005, 2007, 2009 |
| SCRT2 | NM_033129 | 981 | scratch homolog 2, zinc finger protein (*Drosophila*) | hsa-miR-4458 | −0.05 | 0.88 | 2005, 2007, 2009 |
| SURF4 | NM_033161 | 982 | surfeit 4 | hsa-let-7a | −0.02 | 0.87 | 2005, 2007, 2009 |
| PURB | NM_033224 | 983 | purine-rich element binding protein B | hsa-miR-4458 | −0.03 | 0.87 | 2009 |
| RASL10B | NM_033315 | 984 | RAS-like, family 10, member B | hsa-miR-4458 | −0.06 | 0.94 | 2005, 2007, 2009 |
| C20orf54 | NM_033409 | 985 | chromosome 20 open reading frame 54 | hsa-miR-4458 | −0.3 | <0.1 | |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| FAM125B | NM_033446 | 986 | family with sequence similarity 125, member B | hsa-miR-4458 | >−0.01 | 0.77 | 2007, 2009 |
| TSPYL5 | NM_033512 | 987 | TSPY-like 5 | hsa-miR-4458 | −0.24 | 0.58 | |
| TRIM41 | NM_033549 | 988 | tripartite motif containing 41 | hsa-let-7f | −0.22 | 0.92 | |
| STARD13 | NM_052851 | 989 | StAR-related lipid transfer (START) domain containing 13 | hsa-let-7g | −0.4 | >0.99 | 2005, 2007, 2009 |
| VPS26B | NM_052875 | 990 | vacuolar protein sorting 26 homolog B (S. pombe) | hsa-miR-4500 | −0.15 | 0.9 | 2009 |
| EGLN2 | NM_053046 | 991 | egl nine homolog 2 (C. elegans) | hsa-miR-4500 | −0.16 | 0.93 | 2005, 2007, 2009 |
| CCND1 | NM_053056 | 992 | cyclin D1 | hsa-let-7b | −0.12 | 0.99 | 2005, 2007, 2009 |
| GALNTL2 | NM_054110 | 993 | UDP-N-acetyl-alpha-D-galactosamine:polypeptide N-acetylgalactosaminyltransferase-like 2 | hsa-miR-4500 | −0.2 | 0.94 | 2005, 2007, 2009 |
| C20orf112 | NM_080616 | 994 | chromosome 20 open reading frame 112 | hsa-let-7b | −0.22 | 0.97 | |
| TMEM41A | NM_080652 | 995 | transmembrane protein 41A | hsa-miR-4458 | −0.13 | 0.94 | |
| ADAMTS14 | NM_080722 | 996 | ADAM metallopeptidase with thrombospondin type 1 motif, 14 | hsa-miR-4458 | −0.18 | 0.93 | 2007, 2009 |
| ZNF280B | NM_080764 | 997 | zinc finger protein 280B | hsa-let-7d | −0.34 | 0.98 | 2007, 2009 |
| SOCS4 | NM_080867 | 998 | suppressor of cytokine signaling 4 | hsa-miR-4500 | −0.15 | 0.91 | 2005, 2007, 2009 |
| KLHL6 | NM_130446 | 999 | kelch-like 6 (Drosophila) | hsa-let-7d | −0.32 | 0.95 | 2007, 2009 |
| TSPAN18 | NM_130783 | 1000 | tetraspanin 18 | hsa-miR-4500 | −0.08 | 0.94 | |
| UNC5A | NM_133369 | 1001 | unc-5 homolog A (C. elegans) | hsa-let-7d | −0.12 | 0.9 | 2007, 2009 |
| GRIN3A | NM_133445 | 1002 | glutamate receptor, ionotropic, N-methyl-D-aspartate 3A | hsa-miR-4458 | >−0.01 | 0.87 | 2009 |
| PYGO2 | NM_138300 | 1003 | pygopus homolog 2 (Drosophila) | hsa-miR-4500 | −0.07 | 0.92 | 2005, 2007, 2009 |
| DCAF15 | NM_138353 | 1004 | DDB1 and CUL4 associated factor 15 | hsa-miR-4458 | −0.17 | 0.95 | 2007, 2009 |
| MARS2 | NM_138395 | 1005 | methionyl-tRNA synthetase 2, mitochondrial | hsa-let-7d | −0.37 | 0.94 | 2009 |
| MARCH9 | NM_138396 | 1006 | membrane-associated ring finger (C3HC4) 9 | hsa-miR-4500 | −0.09 | 0.78 | 2007, 2009 |
| ZNF689 | NM_138447 | 1007 | zinc finger protein 689 | hsa-miR-4500 | −0.29 | 0.94 | 2009 |
| CTHRC1 | NM_138455 | 1008 | collagen triple helix repeat containing 1 | hsa-miR-4458 | −0.31 | 0.76 | 2009 |
| C11orf84 | NM_138471 | 1009 | chromosome 11 open reading frame 84 | hsa-miR-4458 | −0.14 | 0.94 | 2005, 2007, 2009 |
| H2AFV | NM_138635 | 1010 | H2A histone family, member V | hsa-miR-4458 | >−0.03 | <0.1 | |
| CD200R1 | NM_138806 | 1011 | CD200 receptor 1 | hsa-let-7a | −0.38 | 0.82 | 2009 |
| ADAMTS15 | NM_139055 | 1012 | ADAM metallopeptidase with thrombospondin type 1 motif, 15 | hsa-let-7i | −0.38 | >0.99 | |
| LIPH | NM_139248 | 1013 | lipase, member H | hsa-miR-4500 | −0.29 | 0.94 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| PPTC7 | NM_139283 | 1014 | PTC7 protein phosphatase homolog (*S. cerevisiae*) | hsa-let-7d | −0.06 | 0.85 | 2007, 2009 |
| GNAT1 | NM_144499 | 1015 | guanine nucleotide binding protein (G protein), alpha transducing activity polypeptide 1 | hsa-let-7g | −0.14 | <0.1 | |
| CNOT6L | NM_144571 | 1016 | CCR4-NOT transcription complex, subunit 6-like | hsa-miR-4458 | −0.02 | 0.92 | 2007, 2009 |
| MAPK1IP1L | NM_144578 | 1017 | mitogen-activated protein kinase 1 interacting protein 1-like | hsa-miR-4458 | −0.03 | 0.99 | 2009 |
| TEX261 | NM_144582 | 1018 | testis expressed 261 | hsa-miR-4458 | −0.04 | 0.8 | 2009 |
| FOPNL | NM_144600 | 1019 | FGFR1OP N-terminal like | hsa-let-7a | −0.13 | 0.88 | 2009 |
| KLHL23 | NM_144711 | 1020 | kelch-like 23 (*Drosophila*) | hsa-let-7f | −0.2 | 0.95 | |
| SMCR8 | NM_144775 | 1021 | Smith-Magenis syndrome chromosome region, candidate 8 | hsa-let-7d | −0.16 | 0.95 | 2009 |
| TSPEAR | NM_144991 | 1022 | thrombospondin-type laminin G domain and EAR repeats | hsa-let-7a | −0.16 | 0.9 | 2005, 2007 |
| TET3 | NM_144993 | 1023 | tet oncogene family member 3 | hsa-miR-98 | −0.19 | >0.99 | 2009 |
| CCNY | NM_145012 | 1024 | cyclin Y | hsa-let-7d | −0.22 | 0.94 | |
| SLC2A12 | NM_145176 | 1025 | solute carrier family 2 (facilitated glucose transporter), member 12 | hsa-miR-4500 | −0.2 | 0.93 | 2007, 2009 |
| B3GNT7 | NM_145236 | 1026 | UDP-GlcNAc:betaGal beta-1,3-N-acetylglucosaminyltransferase 7 | hsa-miR-4458 | −0.2 | 0.98 | |
| KIFC2 | NM_145754 | 1027 | kinesin family member C2 | hsa-miR-4500 | −0.16 | 0.64 | |
| MTPN | NM_145808 | 1028 | myotrophin | hsa-let-7d | −0.04 | 0.82 | 2005, 2007, 2009 |
| SYT11 | NM_152280 | 1029 | synaptotagmin XI | hsa-miR-4458 | −0.13 | 0.98 | 2005, 2007, 2009 |
| POGLUT1 | NM_152305 | 1030 | protein O-glucosyltransferase 1 | hsa-let-7f | −0.14 | 0.87 | 2007, 2009 |
| GRPEL2 | NM_152407 | 1031 | GrpE-like 2, mitochondrial (*E. coli*) | hsa-let-7i | −0.18 | 0.93 | 2009 |
| RNF165 | NM_152470 | 1032 | ring finger protein 165 | hsa-miR-4458 | −0.19 | >0.99 | 2007, 2009 |
| ZNF362 | NM_152493 | 1033 | zinc finger protein 362 | hsa-miR-4458 | −0.08 | 0.98 | 2007, 2009 |
| ARL6IP6 | NM_152522 | 1034 | ADP-ribosylation-like factor 6 interacting protein 6 | hsa-miR-4500 | −0.33 | 0.83 | |
| SLC16A14 | NM_152527 | 1035 | solute carrier family 16, member 14 (monocarboxylic acid transporter 14) | hsa-miR-98 | −0.18 | 0.94 | 2007, 2009 |
| C7orf60 | NM_152556 | 1036 | chromosome 7 open reading frame 60 | hsa-let-7a | −0.06 | 0.87 | 2005, 2007, 2009 |
| FAM116A | NM_152678 | 1037 | family with sequence similarity 116, member A | hsa-miR-4458 | −0.08 | 0.7 | |
| SENP5 | NM_152699 | 1038 | SUMO1/sentrin specific peptidase 5 | hsa-miR-4458 | −0.17 | 0.94 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| HOXA9 | NM_152739 | 1039 | homeobox A9 | hsa-let-7d | −0.16 | 0.85 | 2005, 2007, 2009 |
| SDK1 | NM_152744 | 1040 | sidekick homolog 1, cell adhesion molecule (chicken) | hsa-miR-4458 | −0.14 | 0.95 | |
| SCUBE3 | NM_152753 | 1041 | signal peptide, CUB domain, EGF-like 3 | hsa-miR-4458 | >−0.02 | 0.88 | 2005, 2007, 2009 |
| RICTOR | NM_152756 | 1042 | RPTOR independent companion of MTOR, complex 2 | hsa-miR-4500 | −0.14 | 0.98 | 2007, 2009 |
| YTHDF3 | NM_152758 | 1043 | YTH domain family, member 3 | hsa-miR-4500 | −0.1 | 0.86 | 2005, 2007, 2009 |
| MFSD8 | NM_152778 | 1044 | major facilitator superfamily domain containing 8 | hsa-miR-98 | −0.33 | 0.91 | |
| COL24A1 | NM_152890 | 1045 | collagen, type XXIV, alpha 1 | hsa-let-7a | −0.19 | 0.92 | 2005, 2007, 2009 |
| UHRF2 | NM_152896 | 1046 | ubiquitin-like with PHD and ring finger domains 2 | hsa-let-7d | −0.41 | 0.89 | 2005, 2007, 2009 |
| PXT1 | NM_152990 | 1047 | peroxisomal, testis specific 1 | hsa-let-7f | −0.54 | 0.93 | 2009 |
| NPHP3 | NM_153240 | 1048 | nephronophthisis 3 (adolescent) | hsa-let-7f | −0.49 | >0.99 | 2009 |
| BRWD3 | NM_153252 | 1049 | bromodomain and WD repeat domain containing 3 | hsa-let-7i | −0.12 | 0.95 | |
| ATXN7L2 | NM_153340 | 1050 | ataxia 7-like 2 | hsa-miR-4458 | −0.18 | 0.75 | 2007 |
| GPR26 | NM_153442 | 1051 | G protein-coupled receptor 26 | hsa-miR-4500 | −0.17 | 0.95 | 2009 |
| LCORL | NM_153686 | 1052 | ligand dependent nuclear receptor corepressor-like | hsa-miR-4458 | −0.2 | 0.78 | 2007, 2009 |
| FAM43A | NM_153690 | 1053 | family with sequence similarity 43, member A | hsa-miR-4458 | −0.16 | 0.82 | 2009 |
| TTL | NM_153712 | 1054 | tubulin tyrosine ligase | hsa-miR-4458 | −0.08 | 0.94 | 2007, 2009 |
| ATP2A2 | NM_170665 | 1055 | ATPase, Ca++ transporting, cardiac muscle, slow twitch 2 | hsa-miR-4500 | −0.28 | 0.96 | 2005, 2007 |
| IL28RA | NM_170743 | 1056 | interleukin 28 receptor, alpha (interferon, lambda receptor) | hsa-miR-4458 | −0.17 | 0.72 | |
| RDH10 | NM_172037 | 1057 | retinol dehydrogenase 10 (all-trans) | hsa-miR-98 | −0.19 | 0.95 | 2005, 2007, 2009 |
| DCUN1D3 | NM_173475 | 1058 | DCN1, defective in cullin neddylation 1, domain containing 3 (S. cerevisiae) | hsa-miR-4500 | −0.21 | 0.98 | 2007, 2009 |
| LSM11 | NM_173491 | 1059 | LSM11, U7 small nuclear RNA associated | hsa-let-7b | −0.35 | 0.94 | 2005, 2007, 2009 |
| SLC38A9 | NM_173514 | 1060 | solute carrier family 38, member 9 | hsa-miR-4458 | −0.17 | 0.82 | 2005, 2007 |
| KLHDC8B | NM_173546 | 1061 | kelch domain containing 8B | hsa-miR-4458 | −0.35 | 0.98 | 2009 |
| RFX6 | NM_173560 | 1062 | regulatory factor X, 6 | hsa-let-7d | −0.24 | 0.95 | 2005, 2007, 2009 |
| PRR14L | NM_173566 | 1063 | proline rich 14-like | hsa-miR-4458 | −0.03 | 0.9 | |
| UBN2 | NM_173569 | 1064 | ubinuclein 2 | hsa-miR-4458 | >−0.02 | 0.94 | 2009 |
| PGM2L1 | NM_173582 | 1065 | phosphoglucomutase 2-like 1 | hsa-miR-4458 | −0.05 | >0.99 | 2005, 2007, 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| ANKRD52 | NM_173595 | 1066 | ankyrin repeat domain 52 | hsa-miR-4458 | >−0.06 | 0.96 | 2009 |
| RIMKLA | NM_173642 | 1067 | ribosomal modification protein rimK-like family member A | hsa-let-7b | −0.08 | <0.1 | |
| CCDC141 | NM_173648 | 1068 | coiled-coil domain containing 141 | hsa-miR-4458 | −0.17 | 0.95 | |
| SLC9A9 | NM_173653 | 1069 | solute carrier family 9 (sodium/hydrogen exchanger), member 9 | hsa-miR-4458 | −0.11 | 0.89 | 2005, 2007, 2009 |
| C3orf64 | NM_173654 | 1070 | chromosome 3 open reading frame 64 | hsa-let-7d | −0.21 | >0.99 | 2007, 2009 |
| CRB2 | NM_173689 | 1071 | crumbs homolog 2 (Drosophila) | hsa-miR-4458 | −0.12 | 0.93 | 2009 |
| PRTG | NM_173814 | 1072 | protogenin | hsa-miR-98 | −0.56 | >0.99 | 2007, 2009 |
| SREK1IP1 | NM_173829 | 1073 | SREK1-interacting protein 1 | hsa-let-7g | −0.12 | 0.95 | 2007, 2009 |
| FAM84B | NM_174911 | 1074 | family with sequence similarity 84, member B | hsa-miR-4500 | −0.13 | 0.58 | 2007 |
| ZPLD1 | NM_175056 | 1075 | zona pellucida-like domain containing 1 | hsa-miR-4458 | −0.2 | 0.94 | 2009 |
| TXLNA | NM_175852 | 1076 | taxilin alpha | hsa-let-7b | −0.1 | 0.9 | 2009 |
| CHSY3 | NM_175856 | 1077 | chondroitin sulfate synthase 3 | hsa-miR-4500 | −0.17 | 0.75 | 2007 |
| C19orf39 | NM_175871 | 1078 | chromosome 19 open reading frame 39 | hsa-let-7d | −0.32 | 0.77 | |
| ANKRD43 | NM_175873 | 1079 | ankyrin repeat domain 43 | hsa-miR-4500 | −0.22 | 0.94 | 2007, 2009 |
| FLJ36031 | NM_175884 | 1080 | hypothetical protein FLJ36031 | hsa-let-7g | −0.31 | 0.88 | 2007, 2009 |
| C5orf51 | NM_175921 | 1081 | chromosome 5 open reading frame 51 | hsa-miR-4458 | −0.26 | 0.94 | 2005, 2007, 2009 |
| PRR18 | NM_175922 | 1082 | proline rich 18 | hsa-miR-4500 | −0.13 | 0.72 | |
| CXorf36 | NM_176819 | 1083 | chromosome X open reading frame 36 | hsa-let-7e | −0.02 | 0.81 | |
| PDE12 | NM_177966 | 1084 | phosphodiesterase 12 | hsa-let-7a | −0.25 | 0.98 | 2007, 2009 |
| SESTD1 | NM_178123 | 1085 | SEC14 and spectrin domains 1 | hsa-miR-4500 | −0.19 | 0.92 | |
| SNAI3 | NM_178310 | 1086 | snail homolog 3 (Drosophila) | hsa-let-7i | −0.18 | 0.56 | 2007 |
| TMEM26 | NM_178505 | 1087 | transmembrane protein 26 | hsa-miR-4458 | −0.1 | 0.93 | 2009 |
| NAT8L | NM_178557 | 1088 | N-acetyltransferase 8-like (GCN5-related, putative) | hsa-miR-98 | −0.05 | 0.94 | |
| RSPO2 | NM_178565 | 1089 | R-sporadin 2 | hsa-let-7d | −0.3 | 0.88 | 2007, 2009 |
| MTDH | NM_178812 | 1090 | metadherin | hsa-miR-98 | −0.1 | 0.95 | |
| AGPAT6 | NM_178819 | 1091 | 1-acylglycerol-3-phosphate O-acyltransferase 6 (lysophosphatidic acid acyltransferase, zeta) | hsa-let-7d | −0.24 | 0.98 | |
| MFSD4 | NM_181644 | 1092 | major facilitator superfamily domain containing 4 | hsa-let-7a | −0.31 | 0.98 | |
| TMTC3 | NM_181783 | 1093 | transmembrane and tetratricopeptide repeat containing 3 | hsa-miR-4500 | −0.01 | 0.79 | |
| SLC46A3 | NM_181785 | 1094 | solute carrier family 46, member 3 | hsa-miR-4500 | −0.13 | 0.74 | |
| USP12 | NM_182488 | 1095 | ubiquitin specific peptidase 12 | hsa-let-7f | −0.37 | 0.9 | |
| DDX26B | NM_182540 | 1096 | DEAD/H (Asp-Glu-Ala-Asp/His) box polypeptide 26B | hsa-let-7f | −0.25 | 0.94 | 2009 |

TABLE S2-continued

Let-7a/c predicted targets.

| Target gene | Representative transcript | SEQ ID NO: | Gene name | Representative miRNA | Total context + score | Aggregate PCT | Publication (s) |
|---|---|---|---|---|---|---|---|
| GDPD1 | NM_182569 | 1097 | glycerophosphodiester phosphodiesterase domain containing 1 | hsa-miR-4458 | −0.19 | 0.94 | 2005, 2007, 2009 |
| SP8 | NM_182700 | 1098 | Sp8 transcription factor | hsa-miR-4458 | −0.16 | 0.92 | 2007, 2009 |
| ARRDC4 | NM_183376 | 1099 | arrestin domain containing 4 | hsa-miR-4458 | −0.15 | 0.94 | 2005, 2007, 2009 |
| KIF1B | NM_183416 | 1100 | kinesin family member 1B | hsa-miR-4458 | −0.07 | 0.88 | |
| TMEM65 | NM_194291 | 1101 | transmembrane protein 65 | hsa-miR-4500 | −0.2 | 0.94 | 2007, 2009 |
| SLC16A9 | NM_194298 | 1102 | solute carrier family 16, member 9 (monocarboxylic acid transporter 9) | hsa-miR-4458 | −0.25 | 0.9 | 2009 |
| E2F6 | NM_198256 | 1103 | E2F transcription factor 6 | hsa-let-7c | −0.21 | 0.98 | 2007, 2009 |
| ANKRD46 | NM_198401 | 1104 | ankyrin repeat domain 46 | hsa-miR-4458 | −0.19 | 0.87 | 2009 |
| NRK | NM_198465 | 1105 | Nik related kinase | hsa-let-7i | −0.07 | 0.94 | 2005, 2007, 2009 |
| NHLRC2 | NM_198514 | 1106 | NHL repeat containing 2 | hsa-let-7d | −0.08 | 0.83 | |
| ZNF710 | NM_198526 | 1107 | zinc finger protein 710 | hsa-let-7d | −0.24 | >0.99 | 2003, 2007, 2009 |
| TMEM110 | NM_198563 | 1108 | transmembrane protein 110 | hsa-miR-4458 | −0.24 | 0.94 | 2007, 2009 |
| RAB15 | NM_198686 | 1109 | RAB15, member RAS onocogene family | hsa-miR-4458 | −0.16 | 0.94 | 2005, 2007, 2009 |
| DHX57 | NM_198963 | 1110 | DEAH (Asp-Glu-Ala-Asp/His) box polypeptide 57 | hsa-miR-4500 | −0.25 | 0.88 | 2005, 2007, 2009 |
| MED8 | NM_201542 | 1111 | mediator complex subunit 8 | hsa-let-7f | −0.42 | 0.92 | |
| ZNF784 | NM_203374 | 1112 | zinc finger protein 784 | hsa-miR-4458 | −0.21 | 0.83 | 2009 |
| PPAPDC2 | NM_203453 | 1113 | phosphatidic acid phosphatase type 2 domain containing 2 | hsa-miR-4500 | −0.2 | 0.94 | 2007, 2009 |
| SPRYD4 | NM_207344 | 1114 | SPRY domain containing 4 | hsa-miR-4458 | −0.2 | 0.94 | 2007, 2009 |
| FREM2 | NM_207361 | 1115 | FRAS1 related extracellular matrix protein 2 | hsa-miR-4458 | −0.07 | 0.94 | 2009 |
| C10orf140 | NM_207371 | 1116 | chromosome 10 open reading frame 140 | hsa-let-7d | −0.13 | 0.85 | 2005, 2007, 2009 |

TABLE S3

3' UTR sequences.

Human FNTB
5'AGGACCTGGGTCCCGGCAGCTCTTTGCTCACCCATCTCCCCAGTCAGA
CAAGGTTTATACGTTTCAATACATACTGCATTCTGTGCTACACAAGCCTT
AGCCTCAGTGGAGCTGTGGTTCTCTTGGTACTTTCTTGTCAAACAAAACC
AATGGCTCTGGGTTTGGAGAACACAGTGGCTGGTTTTAAAAATTCTTTCC
ACACCTGTCAAACCAAAATCTATCAGCCCACGTGGTGTGGTTGGTGAAC
AGTGCATGCCAGGAGGAAGCAGTCCCTCCTCACCAGCTCTCCAGCCAGGA
CGATCACACAGAGATGAATGGCATCTGAGTATTACGGCATCCAGAGCCAC
TGCTGACTCCCACTTGCACGCCACCATTCAGTCACCAGCTGGGTGCCCT
CCGATGGGTGGAATAAGTCTGCTTCATGCCAAGGCTGGGCTTTGGGTCCC
ACCAAGATGAGTTCTCTGTAAGACTGTGGTGGAGTTGCACCAGGAGGTGC
CTCTGCCTCTCGACTTGCACCCTGGTCATTTGTAAGGGAAAAGAGCTGGA
GGTGGGGAGAGAAAGATCTCCTTCAGTTGGGAGTCCTTCCACTTCAACAC
TGGAGAACTGAGCCTTGCATCTCTCCAGGGTCCAAGGCCACGCTTGGTGC
ACAGGCAAGACTTGCTTCAGCCCCAGGTGTGGTGACTTAGACCTAGGAAA TABLE S3-continued 3' UTR sequences.

CCAATTATGAGTGGAAAGTGACCCTCTAGTTCAACTGTGCCAGAGGAAAC
AGCCCTCCAGTGCCCACCTGCCTCACTCCTCCCTATCATGTACCGTGAAA
ACCCCCTCTGATGGCCTCAAGGCAGTGCCTGCAGGCCGAGGCCCTTCTGG
GGGTTTCTATCTTTCTTCCACCAGACTCCAAGCCCACTCTCCTCCAAGAC
TGTGTTGTCTTTTCTCACCAAGAGTATTAACACTACTAAGTCTTTCACCT
TAACTTATGACTCAGGATTTATTCACGTCCTGCCCACTCTAGGCTCACAG
GAATAAAATCAAGTGCTAGACACACTGGCTGCTACTAAGGCACTAGCCTC
TGTAGCTGGTGGTGGCAGCGTGGGTGCCGCCCAGCGTGCTGGGTCCTGG
CAGTGCCTCTGCTGTGCTGCACATTGAGCCCTTTCTCAGTCAGTGGAGTA
TCAAGTTGGGCCATCTGTCTACTGACCTGGCCTTCATGTAAGCAGCTGTG
GGCTGCGGGCAGACAGGAGCTCAGAGATGCAGCATGAGGCGCTTAGAAAA
ACCTGGCCATTTGCTGCCTCTAATTCCCTTTTGCTTTG-3'
(SEQ ID NO: 1117)

TABLE S3-continued

3' UTR sequences.

Zebrafish Fntb
5'ACTATCTATTTTTCAACTGTAAACATATTGGGGGATTTGGGCTAGCTT
GAACTGTGCAGAGGAATCTTCTGTAAATGCTGTAGCCAAATGTCCTTTGC
TGGTGTGTACAGCGTCTACAGATGGAGAAACACTCTGAGGCCTGATCTGC
TGCTGCTTCAGCATGAGGTTATGGGTTTTAGCCAGGATAAACAGTAGAGA
CTGACTAGGTAAGGTGTTTTTTCATGCACCAGTCATTGATTGATATTTTA
TTGCACATGCCAGCTTATTTTGGGCAAAATGTTCCCAGAGTGTACGTGGC
AGTGGGTTCTGGACAGAAATAAAGACTTGGATGGAAA-3'
(SEQ ID NO: 1118)

Zebrafish Smarca5
5'GCAGGCAGGCATTTCACACACCTCACTCGGCGAGGAGCTTCAGTACAG
CAATACTGCATTGATTGTTACGGGTCCCACTCATGTACTGTATGGATTTG
CAGCACTGATCCTCGCCTCTCAAGTAGCTTGGCCTTCTTAACAAGGTGTA
GAGTTGTAAATTAGGTCTCTTTTAGTTATATAATGTAACTACGGCTGTGC
TGTCGGATGTGTTTTGTATTTATGGCTACTTCAAATTTTTTTTGTACCA
CATTCCATTTGCTTGTATCAGTTTAATTTGCAGTCTTTACCCCCTCATTA
TTAGTGTCTTCAGTATTGTATTGTCTCTGTATCCGCCATTGGAAAGTGAC
TAATAAATGTGGTTTTTATAAATGCTGCTCTGTATGTTTCCTACAAATAA
ATGTAATGTCTTTTGCCTTGTA-3' (SEQ ID NO: 1119)

TABLE S4

MiR mimics and antagomiR sequences.

| miRs used | Sequence |
|---|---|
| Dre-miR-100 mimic | 5'-AACCCGUAGAUCCGAACUUGUG-3' (SEQ ID NO: 1120) 5'-CAAGCUUGUAUCUAUAGGUAUC-3' (SEQ ID NO: 1121) |
| Dre-miR-99 mimic | 5'-AACCCGUAGAUCCGAUCUUGUG-3' (SEQ ID NO: 1122) 5'-CAAGCUCGAUUCUAUGGGUCUC-3' (SEQ ID NO: 1123) |
| Dre-miR-99 inhibitor | 5'-ACAAGTTCGGATCTACGGGT-3' (SEQ ID NO: 1124) |
| Dre-miR-100 inhibitor | 5'-ACAAGATCGGATCTACGGGT-3' (SEQ ID NO: 1125) |
| GFP siRNA (delivery control) | 5'-GGCUACGUCCAGGAGCGCACC-3' (SEQ ID NO: 1126) 5'-GGUGCGCUCCUGGACGUAGCC-3'-Cy5 (SEQ ID NO: 1127) |
| Fntb morpholino (translation-blocking) | 5'-GCGCCTCTTCCATGATGAGCTCTCA-3' (SEQ ID NO: 1128) |
| Smarca5 morpholino (translation-blocking) | 5'-CTTCTTCCCGCTGCTGCTCCATGCT-3' (SEQ ID NO: 1129) |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09220721B2). An electronic copy of the "Sequence Listing" will also be available from the USPTO upon request and payment of the fee set forth in 37 CFR 1.19(b)(3).

What is claimed is:

1. A method of modulating proliferation of a cardiomyocyte, comprising:
(i) introducing into a cardiomyocyte a nucleic acid encoding an antagonist of a micro RNA (miR) 99 micro RNA, a nucleic acid encoding an antagonist of a miR 100 micro RNA, and a nucleic acid encoding an antagonist of a let-7a micro RNA, and a nucleic acid encoding an antagonist of a let-7c micro RNA, thereby forming a transfected cardiomyocyte; and
(ii) allowing the transfected cardiomyocyte to divide, thereby modulating proliferation of the cardiomyocyte.

2. The method of claim 1, wherein the introducing comprises transfecting the cardiomyocyte with a) a lentiviral vector or an adeno-associated viral (AAV) vector comprising the nucleic acid encoding the antagonist of the miR 99 micro RNA and the nucleic acid encoding the antagonist of the miR 100 micro RNA, and b) a lentiviral vector or an AAV vector encoding the nucleic acid encoding the antagonist of the let-7a micro RNA and the antagonist of the let-7c micro RNA.

3. The method of claim 1, wherein the proliferation of the cardiomyocyte is increased compared to a control cardiomyocyte lacking the nucleic acid encoding the antagonist of the miR 99 micro RNA, the nucleic acid encoding the antagonist of the miR 100 micro RNA, the nucleic acid encoding the antagonist of the let-7a micro RNA, and the, and a nucleic acid encoding the antagonist of a let-7 c micro RNA.

4. A method of modulating proliferation of a cardiomyocyte, said method comprising:
(i) contacting a cardiomyocyte with a small molecule that modulates expression or activity of a miR 99 micro RNA-regulated protein, a small molecule that modulates expression or activity of a miR 100 micro RNA-regulated protein, a small molecule that modulates expression or activity of a let-7a micro RNA -regulated protein, and small molecule that modulates expression or activity of a let-7c micro RNA regulated protein, thereby forming a treated cardiomyocyte; and
(ii) allowing said treated cardiomyocyte to divide, thereby modulating proliferation of said cardiomyocyte.

5. The method of claim 4, wherein said proliferation of said cardiomyocyte is increased compared to a control cardiomyocyte lacking said small molecule.

6. The method of claim 4, wherein the small molecule that modulates expression or activity of the miR 99 mirco RNA-regulated protein, the small molecule that modulates expression or activity of the miR 100 micro RNA-regulated protein, the small molecule that modulates expression or activity of the let-7a micro RNA -regulated protein, and/or the small molecule that modulates expression or activity of the let-7c micro RNA regulated protein is a synthetic micro RNA molecule.

7. The method of claim 4, comprising contacting the cardiomyocyte with a nucleic acid molecule comprising the nucleic acid sequence as set forth in SEQ ID NO:1124 or SEQ ID NO:1125.

8. The method of claim 1, further comprising measuring the proliferation of the cardiomyocyte.

9. The method of claim 4, wherein the proliferation of the cardiomyocyte is increased.

10. The method of claim 1, wherein the cardiomyocyte is in vivo.

11. The method of claim 1, wherein the cardiomyocyte is in vitro.

12. The method of claim 2, wherein a) the lentiviral vector or the AAV vector comprising the nucleic acid encoding the antagonist of the mir 99 micro RNA and the antagonist of the mir 100 micro RNA, and b) the lentiviral vector or the AAV vector encoding the nucleic acid encoding the antagonist of the let-7a micro RNA and the antagonist of the let-7c micro RNA are the same vector.

13. The method of claim 2, wherein a) the lentiviral vector or the AAV vector comprising the nucleic acid encoding the antagonist of the mir 99 micro RNA and the antagonist of the mir 100 micro RNA, and b) the lentiviral vector or the AAV vector encoding the nucleic acid encoding the antagonist of the let-7a are different vectors.

14. The method of claim 1, comprising transfecting the cardiomycocyte with a nucleic acid comprising the nucleic acid sequence set forth as SEQ ID NO: 1124.

15. The method of claim 1, comprising transfecting the cardiomycocyte with a nucleic acid comprising the nucleic acid sequence set forth as SEQ ID NO: 1125.

* * * * *